United States Patent [19]
Hastings et al.

[11] Patent Number: 6,008,020
[45] Date of Patent: Dec. 28, 1999

[54] BRAIN-ASSOCIATED INHIBITOR OF TISSUE-TYPE PLASMINOGEN ACTIVATOR

[75] Inventors: Gregg A. Hastings, Thousand Oaks, Calif.; Timothy A. Coleman, Gaithersburg; Daniel A. Lawrence, Derwood, both of Md.; Patrick J. Dillon, Carlsbad, Calif.

[73] Assignees: Human Genome Sciences, Rockville, Md.; The American Red Cross, Falls Church, Va.

[21] Appl. No.: 08/948,997

[22] Filed: Oct. 10, 1997

Related U.S. Application Data

[60] Provisional application No. 60/028,117, Oct. 11, 1996.
[51] Int. Cl.⁶ .......................... C12P 21/06; C12N 15/00; C12N 5/00; C07H 21/04
[52] U.S. Cl. .................. 435/69.2; 435/69.7; 435/252.3; 435/320.1; 435/325; 536/23.1; 536/23.5
[58] Field of Search .......................... 435/69.2, 320.1, 435/440, 325, 252.3, 69.7; 536/23.1, 23.5

[56] References Cited

U.S. PATENT DOCUMENTS 5,700,924  12/1997  Braxton .................................. 536/23.1

FOREIGN PATENT DOCUMENTS 9640922  12/1996  WIPO .

OTHER PUBLICATIONS

Osterwalder et al., (1996) EMBO Journal 15:2944–2953.

*Primary Examiner*—Ponnathapura Achutamurthy
*Assistant Examiner*—Elizabeth Slobodyansky
*Attorney, Agent, or Firm*—Michele M. Wales

[57] ABSTRACT

The present invention relates to a novel BAIT protein which is a member of serpin superfamily which is expressed primarily in brain tissue. In particular, isolated nucleic acid molecules are provided encoding the human BAIT protein. BAIT polypeptides are also provided as are vectors, host cells and recombinant methods for producing the same. The invention further relates to screening methods for identifying agonists and antagonists of BAIT activity. Also provided are diagnostic methods for detecting nervous system-related disorders and therapeutic methods for treating nervous system-related disorders.

43 Claims, 10 Drawing Sheets

```
              P17                                              P1 P1'
              |                                                |  |
       401                                                                                    484
BAIT     NKEIFLSKAI HKSFLEVNEE GSEAAAVSGM IAISR.MAVL YPQVIVDHPF FFLIRNRRTG TILFMGRVMH PETMNTSGHD FEEL
ChkNSP   NKELYLAKAF HKAFLEVNEE GSEAAAVSGM IAISR.MAVL YPQVIVDHPF FFLIRNRRTG TVLFMGRVMH PEAMNTSGHD FEEL
BovPAII  QEFLYVSQAL QKVKIEVNES GTLASSSTAL VVSAR.MAP. .EEIIMDRPF LFVVRHNPTG TVLFMGQVME P.........  ....
RatGDNI  SESLHVSHIL QKAKIEVSED GTKAAVVTTA ILIAR.SSP. .PWFIVDRPF LFCIRHNPTG AILFLGQVNK P.........  ....
MusATIII RDDLYVSDAF HKAFLEVMEE GSEAAASTSV VITGRSLNPN RVTFKANRPF LVLIREVALM TIIFMGRVAN PCVN......  ....
                                                    ⇐=======================================

BAIT     Human brain-associated inhibitor of tPA
ChkNSP   Chicken neuroserpin
BovPAII  Bovine plasminogen activator inhibitor-1
RatGDNI  Rat glial-derived nexin-1
MusATIII Mouse antithrombin III
```

FIG. 2B

```
                          1                                                    50
       HPBCT06R.gcg    GGAAGTTCCT CTTGCTACTC TGGAGCCATT AGTCAAAGCA CAGCTGGTTG
       HPBDG64R.gcg    AGACAGGAAG TTCCTCTTGC TACTCTGGAG CCATTAGTCA AAGCACAGCT
       HPBCR79R.gcg    GGAAGTTCCT CTTGCTACTC TGGAGCCATT AGTCAAAGCA CAGCTGGTTG
      HSDFB55S01X.gcg  GAGCGGAGCG GAGCACAGTC CGCCGAGCAC AAGCTCCAGC ATCCCGTCAG 51                                                  100
       HPBCT06R.gcg    AAGAATGGGC AAACTCTGTG AAGAAGCAAA AAGTAGAAGT ATACCTGCCC
       HPBDG64R.gcg    GGTTGAAGAN TGGGCAAACT CTGTNAAGAA GCAAAAAGTA GAAGTATACC
       HPBCR79R.gcg    AAGAATGGGC AAACTCTGTG AAGAAGCAAA AAGTAGAAGT ATACCTGCCC
      HSDFB55S01X.gcg  GGGTTGCAGG TGTGTGGGAG GCTTGAAACT GTTACAATAT GGCTTTCCTT 101                                                 150
       HPBCT06R.gcg    AGGTTCACAG TGGAACAGGA AATTGATTTA AAAGATGTTT TGAAGGCTCT
       HPBDG64R.gcg    TGCCCAGGTT CACAGTGGAA CAGGAAATTN ATTTAAAAGA TGTTTTGAAG
       HPBCR79R.gcg    AGGTTCACAG TGGAACAGGA AATTGATTTA AAAGATGTTT TGAAGGCTCT
      HSDFB55S01X.gcg  GGACTCTTCT CTTTGCTGGT TCTGCAAAGT ATGGCTACAG GGGCCACTTT 151                                                 200
       HPBCT06R.gcg    TGGAATAACT GAAATTTTCA TCAAAGATGC AAATTTGACA GGCCTCTCTG
       HPBDG64R.gcg    GCTCTTGGAA TAACTGAAAT TTTCATCAAA GATGCAAATT TGACAGGCCT
       HPBCR79R.gcg    TGGAATAACT GAAATTTTCA TCAAAGATGC AAATTTGACA GGCCTCTCTG
      HSDFB55S01X.gcg  CCCTGAGGAA GCCATTGCTG ACTTGTCAGT GAATATGTAT AATCGTCTTA 201                                                 250
       HPBCT06R.gcg    ATAATAAGGA GATTTTTCTT TCCAAAGCAA TTCACAAGTC CTTCCTAGAG
       HPBDG64R.gcg    CTCTGATAAT AAGGAGATTT TCNTTTCCAA AGCAATTCAC AAGTCCTTCC
       HPBCR79R.gcg    ATAATAAGGA GATTTTTCTT TCCAAAGCAA TTCACAAGTC CTTCCTAGAG
      HSDFB55S01X.gcg  GAGCCACTGG TGAAGATGAA ATATTCTCT TCTCTCCATT GAGTATTGCT 251                                                 300
       HPBCT06R.gcg    GTTAAATGAA GGAAGGCTCC AGAAGCTGCT GCTGGTCTTC AGGAATGATT
       HPBDG64R.gcg    TAGAGGTTAA TGNAGGAGGC TCCAGAAGCT GCTGCTGTCT CAGGGATGAT
       HPBCR79R.gcg    GTTAATGAAG AAGGCTCAGA AGCTGCTGCT TGTCTCAGGA ATGATTGCAA
      HSDFB55S01X.gcg  CTTGCAATGG GAATGATGGA ACTTGGGGCC CAAGGATCTA CCCAGAAAGA 301                                                 350
       HPBCT06R.gcg    TGCAATTAGT AGGGTTGGCT GTNCTGTATC CCTCAAGGTT ATTGTCGGCC
       HPBDG64R.gcg    TTGCAATTTA NGTAGGNTGG GCTGTGCTGG TATCCNCAAG GTTATTTTTC
       HPBCR79R.gcg    TTAGTAGGAT GGCTGTGCTG TATCCTCAAG GTTATTGTCG ACCATCCATT
      HSDFB55S01X.gcg  AATCCGCCAC TCAATGGGAT ATGACAGCCT AAAAAATGGT GAAGAATTTT
```

FIG. 4A

```
                    351                                                400
    HPBCT06R.gcg    ATCC...... .......... .......... .......... ..........
    HPBDG64R.gcg    GG........ .......... .......... .......... ..........
    HPBCR79R.gcg    TTTCCTTTCT TATCAGAACC AGGGGACCTG GTACAATTCT ATTCATGGG.
    HSDFB55S01X.gcg CTTTCTTGAA GGAGTTTTCA AACATGGTAA CTGCTAAAGA GAGCCAATAT 401                                                450
    HPBCT06R.gcg    .......... .......... .......... .......... ..........
    HPBDG64R.gcg    .......... .......... .......... .......... ..........
    HPBCR79R.gcg    .......... .......... .......... .......... ..........
    HSDFB55S01X.gcg GTGATGAAAA TTGCCAATTC CTTGTTTGTG CAAAATGGAT TTCATGTCAA 451                                                500
    HPBCT06R.gcg    .......... .......... .......... .......... ..........
    HPBDG64R.gcg    .......... .......... .......... .......... ..........
    HPBCR79R.gcg    .......... .......... .......... .......... ..........
    HSDFB55S01X.gcg TGAGGAGTTT TTGCAAATGA TGAAAAAATA TTTTAATGCA GCAGTAAATC 501                                                550
    HPBCT06R.gcg    .......... .......... .......... .......... ..........
    HPBDG64R.gcg    .......... .......... .......... .......... ..........
    HPBCR79R.gcg    .......... .......... .......... .......... ..........
    HSDFB55S01X.gcg ATGTGGACTT CAGTCAAAAT GTAGCCGTGG CCAACTACAT CAATAAGTGG 551                                                600
    HPBCT06R.gcg    .......... .......... .......... .......... ..........
    HPBDG64R.gcg    .......... .......... .......... .......... ..........
    HPBCR79R.gcg    .......... .......... .......... .......... ..........
    HSDFB55S01X.gcg GTGGAGAATA ACACAAACAA TCTGGTGAAA GATTTGGTAT CCCCAAGGGA 601                                                650
    HPBCT06R.gcg    .......... .......... .......... .......... ..........
    HPBDG64R.gcg    .......... .......... .......... .......... ..........
    HPBCR79R.gcg    .......... .......... .......... .......... ..........
    HSDFB55S01X.gcg TTTTGATGCT GCCACTTATC TGGCCCTCAT TAATGCTGTC TATTTCAAGG 651                                                700
    HPBCT06R.gcg    .......... .......... .......... .......... ..........
    HPBDG64R.gcg    .......... .......... .......... .......... ..........
    HPBCR79R.gcg    .......... .......... .......... .......... ..........
    HSDFB55S01X.gcg GGAACTGGAA GTCGCAGTTT AGGCCTGAAA ATACTAGAAC CTTTTCTTTC
```

FIG. 4B

```
                        701                                                      750
      HPBCT06R.gcg      ..........  ..........  ..........  ..........  ..........
      HPBDG64R.gcg      ..........  ..........  ..........  ..........  ..........
      HPBCR79R.gcg      ..........  ..........  ..........  ..........  ..........
    HSDFB55S01X.gcg     ACTAAAGATG  ATGAAAGTGA  AGTCCAAATT  CCAATGATGT  ATCAGCAAGG 751                                                      800
      HPBCT06R.gcg      ..........  ..........  ..........  ..........  ..........
      HPBDG64R.gcg      ..........  ..........  ..........  ..........  ..........
      HPBCR79R.gcg      ..........  ..........  ..........  ..........  ..........
    HSDFB55S01X.gcg     AGAATTTTAT  TATGGGGAAT  TTAGTGATGG  CTCCAATGAA  GCTGGTGGTA 801                                                      850
      HPBCT06R.gcg      ..........  ..........  ..........  ..........  ..........
      HPBDG64R.gcg      ..........  ..........  ..........  ..........  ..........
      HPBCR79R.gcg      ..........  ..........  ..........  ..........  ..........
    HSDFB55S01X.gcg     TCTACCAAGT  CCTAGAAATA  CCATATGAAG  GAGATGAAAT  AAGCATGATG 851                                                      900
      HPBCT06R.gcg      ..........  ..........  ..........  ..........  ..........
      HPBDG64R.gcg      ..........  ..........  ..........  ..........  ..........
      HPBCR79R.gcg      ..........  ..........  ..........  ..........  ..........
    HSDFB55S01X.gcg     CTGGTGCTGT  CCAGACAGGA  AGTTCCTCTT  GCTACTCTGG  AGCCATTAGT 901                                                      950
      HPBCT06R.gcg      ..........  ..........  ..........  ..........  ..........
      HPBDG64R.gcg      ..........  ..........  ..........  ..........  ..........
      HPBCR79R.gcg      ..........  ..........  ..........  ..........  ..........
    HSDFB55S01X.gcg     CAAAGCACAG  CTGGTTGAAG  AATGGGCAAA  CTCTGTGAAG  AAGCAAAAAG 951                                                     1000
      HPBCT06R.gcg      ..........  ..........  ..........  ..........  ..........
      HPBDG64R.gcg      ..........  ..........  ..........  ..........  ..........
      HPBCR79R.gcg      ..........  ..........  ..........  ..........  ..........
    HSDFB55S01X.gcg     TAGAAGTATA  CCTGCCCAGG  TTCACAGTGG  AACAGGAAAT  TGATTTAAAA 1001                                                    1050
      HPBCT06R.gcg      ..........  ..........  ..........  ..........  ..........
      HPBDG64R.gcg      ..........  ..........  ..........  ..........  ..........
      HPBCR79R.gcg      ..........  ..........  ..........  ..........  ..........
    HSDFB55S01X.gcg     GATGTTTTGA  AGGCTCTTGG  AATAACTGAA  ATTTTCATCA  AAGATGCAAA
```

FIG. 4C

```
              1051                                             1100
HPBCT06R.gcg  .......... .......... .......... .......... ..........
HPBDG64R.gcg  .......... .......... .......... .......... ..........
HPBCR79R.gcg  .......... .......... .......... .......... ..........
HSDFB55S01X.gcg TTTGACAGGC CTCTCTGATA ATAAGGAGAT TTTTCTTTCC AAAGCAATTC 1101                                             1150
HPBCT06R.gcg  .......... .......... .......... .......... ..........
HPBDG64R.gcg  .......... .......... .......... .......... ..........
HPBCR79R.gcg  .......... .......... .......... .......... ..........
HSDFB55S01X.gcg ACAAGTCCTT CCTAGAGGTT AATGAAGAAG GCTCAGAAGC TGCTGCTGTC 1151                                             1200
HPBCT06R.gcg  .......... .......... .......... .......... ..........
HPBDG64R.gcg  .......... .......... .......... .......... ..........
HPBCR79R.gcg  .......... .......... .......... .......... ..........
HSDFB55S01X.gcg TCAGGAATGA TTGCAATTAG TAGGATGGCT GTGCTGTATC CTCAAGTTAT 1201                                             1250
HPBCT06R.gcg  .......... .......... .......... .......... ..........
HPBDG64R.gcg  .......... .......... .......... .......... ..........
HPBCR79R.gcg  .......... .......... .......... .......... ..........
HSDFB55S01X.gcg TGTCGACCAT CCATTTTTCT TTCTTATCAG AAACAGGAGA ACTGGTACAA 1251                                             1300
HPBCT06R.gcg  .......... .......... .......... .......... ..........
HPBDG64R.gcg  .......... .......... .......... .......... ..........
HPBCR79R.gcg  .......... .......... .......... .......... ..........
HSDFB55S01X.gcg TTCTATTCAT GGGACGAGTC ATGCATCCTG AAACAATGAA CACAAGTGGA 1301                                             1350
HPBCT06R.gcg  .......... .......... .......... .......... ..........
HPBDG64R.gcg  .......... .......... .......... .......... ..........
HPBCR79R.gcg  .......... .......... .......... .......... ..........
HSDFB55S01X.gcg CATGATTTCG AAGAACTTTA AGTTACTTTA TTTGAATAAC AAGGAAAACA 1351                                             1400
HPBCT06R.gcg  .......... .......... .......... .......... ..........
HPBDG64R.gcg  .......... .......... .......... .......... ..........
HPBCR79R.gcg  .......... .......... .......... .......... ..........
HSDFB55S01X.gcg GTAACTAAGC ACATTATGTT TGCAACTGGT ATATATTTAG GATTTGTGTT
```

FIG. 4D

```
                       1401                                                    1450
         HPBCT06R.gcg  ..........  ..........  ..........  ..........  ..........
         HPBDG64R.gcg  ..........  ..........  ..........  ..........  ..........
         HPBCR79R.gcg  ..........  ..........  ..........  ..........  ..........
      HSDFB55S01X.gcg  TTACAGTATA  TCTTAAGATA  ATATTTAAAA  TAGTTCCAGA  TAAAAACAAT 1451                                                    1500
         HPBCT06R.gcg  ..........  ..........  ..........  ..........  ..........
         HPBDG64R.gcg  ..........  ..........  ..........  ..........  ..........
         HPBCR79R.gcg  ..........  ..........  ..........  ..........  ..........
      HSDFB55S01X.gcg  ATATGTAAAT  TATAAGTAAC  TTGTCAAGGA  ATGTTATCAG  TATTAAGCTA 1501                                                    1550
         HPBCT06R.gcg  ..........  ..........  ..........  ..........  ..........
         HPBDG64R.gcg  ..........  ..........  ..........  ..........  ..........
         HPBCR79R.gcg  ..........  ..........  ..........  ..........  ..........
      HSDFB55S01X.gcg  ATGGTCCTGT  TATGTCATTG  TGTTTGTGTG  CTGTTGTTTA  AAATAAAAGT 1551        1564
         HPBCT06R.gcg  ..........  ....
         HPBDG64R.gcg  ..........  ....
         HPBCR79R.gcg  ..........  ....
      HSDFB55S01X.gcg  ACCTATTGAA  CATG
```

FIG. 4E

BRAIN-ASSOCIATED INHIBITOR OF TISSUE-TYPE PLASMINOGEN ACTIVATOR

This application claims benefit of 35U.S.C. Section 120 based on copending U.S. provisional application Serial No. 60/028,117, filed Oct. 11, 1996.

FIELD OF THE INVENTION

The present invention relates to a novel human gene encoding a polypeptide expressed in human brain tissue which is a member of the serine protease inhibitor ("serpin") superfamily and appears to be a human homolog of "neuroserpin," a serpin recently identified in the chicken. More specifically, isolated nucleic acid molecules are provided encoding a human polypeptide named Brain-Associated Inhibitor of Tissue-Type Plasminogen Activator, hereinafter referred to as "BAIT." BAIT polypeptides are also provided, as are vectors, host cells and recombinant methods for producing the same. The invention further relates to screening methods for identifying agonists and antagonists of BAIT activity. Also provided are diagnostic methods for detecting disorders related to the central and peripheral nervous system and the circulatory system, and therapeutic methods for treating such disorders.

BACKGROUND OF THE INVENTION

Localized proteolytic activity through the action of proteases plays a critical regulatory role in a variety of important biological processes. For instance, the enzyme plasmin plays such a role in hemostasis, angiogenesis, tumor metastisis, cellular migration and ovulation. Plasmin is generated from its precursor zymogen plasminogen by the action of plasminogen activators (PAs) such as tissue-type PA (t-PA) and urokinase-type (u-PA), both of which are serine proteases. The activity of the PA system is precisely regulated by several mechanisms, one of which involves the interaction of t-PA and u-PA with specific plasminogen activator inhibitors. Among these serine protease inhibitors (i.e., serpins), plasminogen activator inhibitor type 1 (PAI-1) is unique in its ability to efficiently inhibit u-PA as well as the single and two-chain forms of t-PA. High PAI-1 levels are associated with an increased risk of thromboembolic disease, while PAI-1 deficiency may represent an inherited autosomal recessive bleeding disorder. See, for instance, Reilly, T. M., et al., Recombinant plasminogen activator inhibitor type 1: a review of structural, functional, and biological aspects, *Blood Coag. And Fibrinolysis* 5:73–81 (1994).

Serpin Mechanism

The serpins are a gene family that encompasses a wide variety of protein products, including many of the proteinase inhibitors in plasma (Huber & Carrell, 1989; full citations of references cited in this section on Serpin Mechanism are listed at the end of this section). However, in spite of their name, not all serpins are proteinase inhibitors. They include steroid binding globulins, the prohormone angiotensinogen, the egg white protein ovalbumin, and barley protein Z, a major constituent of beer. The serpins are thought to share a common tertiary structure (Doolittle. 1983) and to have evolved from a common ancestor (Hunt & Dayhoff. 1980). Proteins with recognizable sequence homology have been identified in vertebrates, plants, insects and viruses but not, thus far, in prokaryotes (Huber & Carrell. 1989; Sasaki. 1991; Komiyama, Ray, Pickup, et al. 1994). Current models of serpin structure are based largely on seminal X-ray crystallographic studies of one member of the family, α-1-antitrypsin (Δ1AT), also called α-1-proteinase inhibitor (Huber & Carrell. 1989).

The structure of a modified form of α1AT, cleaved in its reactive center, was solved by Loebermann and coworkers in 1984 (Loebermann, Tokuoka, Deisenhofer, & Huber. 1984). An interesting feature of this structure was that the two residues normally comprising the reactive center (Met-Ser), were found on opposite ends of the molecule, separated by almost 70 Å. Loebermann and coworkers proposed that a relaxation of a strained configuration takes place upon cleavage of the reactive center peptide bond, rather than a major rearrangement of the inhibitor structure. In this model, the native reactive center is part of an exposed loop, also called the strained loop (Loebermann, Tokuoka, Deisenhofer, & Huber. 1984; Carrell & Boswell. 1986; Sprang. 1992). Upon cleavage, this loop moves or "snaps back", becoming one of the central strands in a major β-sheet structure (β-sheet A). This transformation is accompanied by a large increase in thermal stability (Carrell & Owen. 1985; Gettins & Harten. 1988; Bruch, Weiss, & Engel. 1988; Lawrence, Olson, Palaniappan, & Ginsburg. 1994b).

Recent crystallographic structures of several native serpins, with intact reactive center loops, have confirmed Loebermann's hypothesis that the overall native serpin structure is very similar to cleaved α1AT, but that the reactive center loop is exposed above the plane of the molecule (Schreuder, de Boer, Dijkema, et al. 1994; Carrell, Stein, Fermi, & Wardell. 1994; Stein, Leslie, Finch, Turnell, McLaughlin, & Carrell. 1990; Wei, Rubin, Cooperman, & Christianson. 1994). Additional evidence for this model has come from studies where synthetic peptides, homologous to the reactive center loops of α1AT, antithrombin III (ATIII), or PAI-1 when added in trans, incorporate into their respective molecules, presumably as a central strand of β-sheet A (Björk, Ylinenjarvi, Olson, & Bock. 1992; Björk, Nordling, Larsson, & Olson. 1992; Schulze, Baumann, Knof, Jaeger, Huber, & Laurell. 1990; Carrell, Evans, & Stein. 1991; Kvassman, Lawrence, & Shore. 1995). This leads to an increase in thermal stability similar to that observed following cleavage of a serpin at its reactive center, and converts the serpin from an inhibitor to a substrate for its target proteinase. A third serpin structural form has also been identified, the so-called latent conformation. In this structure the reactive center loop is intact, but instead of being exposed, the entire amino-terminal side of the reactive center loop is inserted as the central strand into β-sheet A (Mottonen, Strand, Symersky, et al. 1992). This accounts for the increased stability of latent PAI-1 (Lawrence, Olson, Palaniappan, & Ginsburg. 1994a) as well as its lack of inhibitory activity (Hekman & Loskutoff. 1985). The ability to adopt this conformation is not unique to PAI-1, but has also now been shown for ATIII and Δ1AT (Carrell, Stein, Fermi, & Wardell. 1994; Lomas, Elliot, Chang, Wardell, & Carrell. 1995). Together, these data have led to the hypothesis that active serpins have mobile reactive center loops, and that this mobility is essential for inhibitor function (Lawrence, Strandberg, Ericson, & Ny. 1990; Carrell, Evans, & Stein. 1991; Carrell & Evans. 1992; Lawrence, Olson, Palaniappan, & Ginsburg. 1994b; Shore, Day, Francis-Chmura, et al. 1994; Lawrence, Ginsburg, Day, et al. 1995; Fa, Karolin, Aleshkov, Strandberg, Johansson, & Ny. 1995; Olson, Bock, Kvassman, et al. 1995). The large increase in thermal stability observed with loop insertion, is presumably due to reorganization of the five stranded β-sheet A from a mixed parallel-antiparallel arrangement to a six stranded, predominantly antiparallel β-sheet (Carrell &

Owen. 1985; Gettins & Harten. 1988; Bruch, Weiss, & Engel. 1988; Lawrence, Olson, Palaniappan, & Ginsburg. 1994a). This dramatic stabilization has led to the suggestion that native inhibitory serpins may be metastable structures, kinetically trapped in a state of higher free energy than their most stable thermodynamic state (Lawrence, Ginsburg, Day, et al. 1995; Lee, Park, & Yu. 1996). Such an energetically unfavorable structure would almost certainly be subject to negative selection, and thus its retention in all inhibitory serpins implies that it has been conserved for functional reasons.

The serpins act as "suicide inhibitors" that react only once with a target proteinase forming an SDS-stable complex. They interact by presenting a "bait" amino acid residue, in their reactive center, to the enzyme. This bait residue is thought to mimic the normal substrate of the enzyme and to associate with the specificity crevice, or S1 site, of the enzyme (Carrell & Boswell. 1986; Huber & Carrell. 1989; Bode & Huber. 1994). The bait amino acid is called the P1 residue, with the amino acids toward the N-terminal side of the scissile reactive center bond labeled in order P1 P2 P3 etc. and the amino acids on the carboxyl side labeled P1' P2' etc. (Carrell & Boswell. 1986). The reactive center P1'-P1' residues, appear to play a major role in determining target specificity. This point was dramatically illustrated by the identification of a unique human mutation, α1AT "Pittsburgh", in which a single amino acid substitution of Arg for Met at the P1 residue converted α1AT from an inhibitor of elastase to an efficient inhibitor of thrombin, resulting in a unique and ultimately fatal bleeding disorder (Owen, Brennan, Lewis, & Carrell. 1983). Numerous mutant serpins have been constructed, demonstrating a wide range of changes in target specificity, particularly with substitutions at P1 (York, Li, & Gardell. 1991; Strandberg, Lawrence, Johansson, & Ny. 1991; Shubeita, Cottey, Franke, & Gerard. 1990; Lawrence, Strandberg, Ericson, & Ny. 1990; Sherman, Lawrence, Yang, et al. 1992).

The exact structure of the complex between serpins and their target proteinases has been controversial. Originally it was thought that the complex was covalently linked via an ester bond between the active site serine residue of the proteinase and the new carboxyl-terminal end of the P1 residue, forming an acyl-enzyme complex (Moroi & Yamasaki, 1974; Owen, 1975; Cohen, Gruenke, Craig, & Geczy. 1977; Nilsson & Wiman. 1982). However, in the late 1980s and early 1990s it was suggested that this interpretation was incorrect, and that the serpin-proteinase complex is instead trapped in a tight non-covalent association similar to the so called standard mechanism inhibitors of the Kazal and Kunitz family (Longstaff & Gaffney, J. 1991; Shieh, Potempa, & Travis. 1989; Potempa, Korzus, & Travis. 1994). Alternatively, one study suggested a hybrid of these two models where the complex was frozen in a covalent but un-cleaved tetrahedral transition state configuration (Matheson, van Halbeek, & Travis. 1991). Recently however, new data by several groups have suggested that the debate has come full circle, with various studies using independent methods indicating that the inhibitor is indeed cleaved in its reactive-center and that the complex is most likely trapped as a covalent acyl-enzyme complex (Lawrence, Ginsburg, Day, et al. 1995; Olson, Bock, Kvassman, et al. 1995; Fa, Karolin, Aleshkov, Strandberg, Johansson, & Ny. 1995; Wilczynska, Fa, Ohlsson, & Ny. 1995; Lawrence, Olson, Palaniappan, & Ginsburg. 1994b; Shore, Day, Francis-Chmura, et al. 1994; Plotnick, Mayne, Schechter, & Rubin. 1996).

Recently, three groups have almost simultaneously proposed similar mechanisms for serpin inhibition (Lawrence, Ginsburg, Day, et al. 1995; Wilczynska, Fa, Ohlsson, & Ny. 1995; Wright & Scarsdale. 1995). This model suggests that upon encountering a target proteinase, a serpin binds to the enzyme forming a reversible complex that is similar to a Michaelis complex between an enzyme and substrate. Next, the proteinase cleaves the P1-P1' peptide bond resulting in formation of a covalent acyl-enzyme intermediate. This cleavage is coupled to a rapid insertion of the reactive center loop (RCL) into β-sheet A at least up to the P9 position. Since the RCL is covalently linked to the enzyme via the active-site Ser, this transition should also affect the proteinase, significantly changing its position relative to the inhibitor. If, during this transition, the RCL is prevented from attaining full insertion because of its association with the enzyme, and the complex becomes locked, with the RCL only partially inserted, then the resulting stress might be sufficient to distort the active site of the enzyme. This distortion would then prevent efficient deacylation of the acyl-enzyme intermediate, thus trapping the complex. However, if RCL insertion is prevented, or if deacylation occurs before RCL insertion then the cleaved serpin is turned over as a substrate and the active enzyme released. This means that what determines whether a serpin is an inhibitor or a substrate is the ratio of $k_{diss}$ to $k_{stab}$. If deacylation ($k_{diss}$) is faster than RCL insertion ($k_{stab}$) then the substrate reaction predominates. However, if RCL insertion and distortion of the active site can occur before deacylation then the complex is frozen as a covalent acyl-enzyme. A similar model was first proposed in 1990 (Lawrence, Strandberg, Ericson, & Ny. 1990) and is consistent with studies demonstrating that RCL insertion is not required for proteinase binding but is necessary for stable inhibition (Lawrence, Olson, Palaniappan, & Ginsburg. 1994b) as well as the observation that only an active enzyme can induce RCL insertion (Olson, Bock, Kvassman, et al. 1995). Very recently, direct evidence for this model was provided by Plotnick et al., who by NMR observed an apparent distortion of an enzyme's catalytic site in a serpin-enzyme complex (Plotnick, Mayne, Schechter, & Rubin. 1996). In conclusion, these data suggest that serpins act as molecular springs where the native structure is kinetically trapped in a high energy state. Upon association with an enzyme some of the energy liberated by RCL insertion is used to distort the active site of the enzyme, preventing deacylation and trapping the complex.

REFERENCES CITED IN SERPIN MECHANISM SECTION

Bjork, I., Nordling, K., Larsson, I., & Olson, S. T. (1992). Kinetic characterization of the substrate reaction between a complex of antithrombin with a synthetic reactive-bond loop tetradecapeptide and four target proteinases of the inhibitor. The Journal of Biological Chemistry, 267, 19047–19050.

Björk, I., Ylinenjärvi, K., Olson, S. T., & Bock, P. E. (1992). Conversion of antithrombin from an inhibitor of thrombin to a substrate with reduced heparin affinity and enhanced conformational stability by binding of a tetradecapeptide corresponding to the P1 to P14 region of the putative reactive bond loop of the inhibitor. The Journal of Biological Chemistry, 267, 1976–1982.

Bode, W., & Huber, R. (1994). Proteinase-Protein Inhibitor Interactions. Fibrinolysis, 8, 161–171.

Bruch, M., Weiss, V., & Engel, J. (1988). Plasma serine proteinase inhibitors (serpins) exhibit major conformational changes and a large increase in conformational stability upon cleavage at their reactive sites. The Journal of Biological Chemistry, 263, 16626–16630.

Carrell, R. W., & Boswell, D. R. (1986). Serpins: the superfamily of plasma serine proteinase inhibitors. In A. J. Barrett & G. Salvesen (Eds.), Proteinase Inhibitors. (pp. 403–420). Amsterdam: Elsevier Science Publishers (Biomedical Division).

Carrell, R. W., Evans, D. L., & Stein, P. E. (1991). Mobile reactive centre of serpins and the control of thrombosis. Nature, 353, 576–578.

Carrell, R. W., & Evans, D. L. I. (1992). Serpins: mobile conformations in a family of proteinase inhibitors. Curr Opin Struct Biol, 2, 438–446.

Carrell, R. W., & Owen, M. C. (1985). Plakalbumin, alpha-1-antitrypsin, antithrombin and the mechanism of inflammatory thrombosis. Nature, 317, 730–732.

Carrell, R. W., Stein, P. E., Fermi, G., & Wardell, M. R. (1994). Biological implications of a 3 Å structure of dimeric antithrombin. Structure, 2, 257–270.

Cohen, A. B., Gruenke, L. D., Craig, J. C., & Geczy, D. (1977). Specific lysine labeling by 18OH— during alkaline cleavage of the a-1-antitrypsin-trypsin complex. Proceedings of the National Academy of Sciences, U.S.A., 74, 4311–4314.

Doolittle, R. F. (1983). Angiotensinogen is related to the antitrypsin-antithrombin-ovalbumin family. Science, 222, 417–419.

Fa, M., Karolin, J., Aleshkov, S., Strandberg, L., Johansson, L. B.-Å., & Ny, T. (1995). Time-Resolved Polarized Fluorescence Spectroscopy Studies of Plasminogen Activator Inhibitor Type 1: Conformational Changes of the Reactive Center upon Interactions with Target proteases, Vitronectin and Heparin. Biochemistry, 34, 13833–13840.

Gettins, P., & Harten, B. (1988). Properties of thrombin- and elastase-modified human antithrombin III. Biochemistry, 27, 3634–3639.

Hekman, C. M., & Loskutoff, D. J. (1985). Endothelial cells produce a latent inhibitor of plasminogen activators that can be activated by denaturants. The Journal of Biological Chemistry, 260, 11581–11587.

Huber, R., & Carrell, R. W. (1989). Implications of the three-dimensional structure of alpha 1 -antitrypsin for structure and function of serpins. Biochemistry, 28, 8951–8966.

Hunt, L. T., & Dayhoff, M. O. (1980). A surprising new protein superfamily containing ovalbumin, antithrombin III, and alpha 1-proteinase inhibitor. Biochemical and Biophysical Research Communications, 95, 864–871.

Komiyama, T., Ray, C. A., Pickup, D. J., Howard, A.D., Thornberry, N. A., Peterson, E. P., & Salvesen, G. (1994). Inhibition of interleukin-1b converting enzyme by the cowpox virus serpin CrmA. An example of cross-class inhibition. The Journal of Biological Chemistry, 269, 19331–19337.

Kvassman, J., Lawrence, D., & Shore, J. (1995). The acid stabilization of plasminogen activator inhibitor-1 depends on protonation of a single group that affects loop insertion into b-sheet A. J Biol Chem, 270, 27942–27947.

Lawrence, D. A., Ginsburg, D., Day, D. E., Berkenpas, M. B., Verhamme, I. M., Kvassman, J.-O., & Shore, J. D. (1995). Serpin-Protease Complexes are Trapped as Stable Acyl-Enzyme Intermediates. J Biol Chem, 270, 25309–25312.

Lawrence, D. A., Olson, S. T., Palaniappan, S., & Ginsburg, D. (1994a). Engineering plasminogen activator inhibitor-1 (PAI-1) mutants with increased functional stability. Biochemistry, 33, 3643–3648.

Lawrence, D. A., Olson, S. T., Palaniappan, S., & Ginsburg, D. (1994b). Serpin reactive-center loop mobility is required for inhibitor function but not for enzyme recognition. The Journal of Biological Chemistry, 269, 27657–27662.

Lawrence, D. A., Strandberg, L., Ericson, J., & Ny, T. (1990). Structure-function studies of the SERPIN plasminogen activator inhibitor type 1: analysis of chimeric strained loop mutants. The Journal of Biological Chemistry, 265, 20293–20301.

Lee, K. N., Park, S. D., & Yu, M.-H. (1996). Probing the native strain in a1-proteinase. Nature Structural Biology, 3, 497–500.

Loebermann, H., Tokuoka, R., Deisenhofer, J., & Huber, R. (1984). Human a1-proteinase inhibitor. Crystal structure analysis of two crystal modifications, molecular model and preliminary analysis of the implications for function. J Mol Biol, 177, 531–557.

Lomas, D. A., Elliot, P. R., Chang, W.-S. W., Wardell, M. R., & Carrell, R. W. (1995). Preparation and characterization of latent a1-antitrypsin. J Biol Chem, 270, 5282–5288.

Longstaff, C., & Gaffney, P., J. (1991). Serpin-serine protease binding kinetics: alpha-2-antiplasmin as a model inhibitor. Biochemistry, 30, 979–986.

Matheson, N. R., van Halbeek, H., & Travis, J. (1991). Evidence for a tetrahedral intermediate complex during serpin-proteinase interactions. The Journal of Biological Chemistry, 266, 13489–13491.

Moroi, M., & Yamasaki, M. (1974). Mechanism of the interaction of bovine trypsin with human a1-antitrypsin. Biochim Biophys Acta, 359, 130–141.

Mottonen, J., Strand, A., Symersky, J., Sweet, R. M., Danley, D. E., Geoghegan, K. F., Gerard, R. D., & Goldsmith, E. J. (1992). Structural basis of latency in plasminogen activator inhibitor-1. Nature, 355, 270–273.

Nilsson, T., & Wiman, B. (1982). On the structure of the stable complex between plasmin and a2-antiplasmin. FEBS Lett, 142, 111–114.

Olson, S. T., Bock, P. E., Kvassman, J., Shore, J. D., Lawrence, D. A., Ginsburg, D., & Björl, I. (1995). Role of the catalytic serine in the interactions of serine proteinases with protein inhibitors of the serpin family. J Biol Chem, 270, 30007–30017.

Owen, M. C., Brennan, S. O., Lewis, J. H., & Carrell, R. W. (1983). Mutation of antitrypsin to antithrombin: alpha1-antitrypsin Pittsburgh (358 Met-Arg), a fatal bleeding disorder. N Engl J Med, 309, 694–698.

Owen, W. G. (1975). Evidence for the formation of an ester between thrombin and heparin cofactor. Biochim Biophys Acta, 405, 380–387.

Plotnick, M. I., Mayne, L., Schechter, N. M., & Rubin, H. (1996). Distortion of the active site of chymotrypsin complexed with a serpin. Biochemistry, 35, 7586–7590.

Potempa, J., Korzus, E., & Travis, J. (1994). The serpin superfamily of proteinase inhibitors: structure, function, and regulation. The Journal of Biological Chemistry, 269, 15957–15960.

Sasaki, T. (1991). Patchwork-structure serpins from silkworm (Bombyx mori) larval hemolymph. Eur J Biochem, 202, 255–261.

Schreuder, H. A., de Boer, B., Dijkema, R., Mulders, J., Theunissen, H. J. M., Grootenhuis, P. D. J., & Hol, W. G. J. (1994). The intact and cleaved human antithrombin III complex as a model for serpin-proteinase interactions. Nature Structural Biology, 1, 48–54.

Schulze, A. J., Baumann, U., Knof, S., Jaeger, E., Huber, R., & Laurell, C. (1990). Structural transition of a1-antitrypsin by a peptide sequentially similar to b-strand s4A. Eur J Biochem, 194, 51–56.

Sherman, P. M., Lawrence, D. A., Yang, A. Y., Vandenberg, E. T., Paielli, D., Olson, S. T., Shore, J. D., & Ginsburg, D. (1992). Saturation mutagenesis of the plasminogen activator inhibitor-1 reactive center. The Journal of Biological Chemistry, 267, 7588–7595.

Shieh, B. H., Potempa, J., & Travis, J. (1989). The use of alpha 2-antiplasmin as a model for the demonstration of complex reversibility in serpins. J Biol Chem, 264, 13420–13423.

Shore, J. D., Day, D. E., Francis-Chmura, A. M., Verhamme, I., Kvassman, J., Lawrence, D. A., & Ginsburg, D. (1994). A fluorescent probe study of plasminogen activator inhibitor-1: Evidence for reactive center loop insertion and its role in the inhibitory mechanism. The Journal of Biological Chemistry, 270, 5395–5398.

Shubeita, H. E., Cottey, T. L., Franke, A. E., & Gerard, R. D. (1990). Mutational and immunochemical analysis of plasminogen activator inhibitor 1. The Journal of Biological Chemistry, 265, 18379–18385.

Sprang, S. R. (1992). The latent tendencies of PAI-1. Trends Biochem Sci, 17, 49–50.

Stein, P. E., Leslie, A. G. W., Finch, J. T., Turnell, W. G., McLaughlin, P. J., & Carrell, R. W. (1990). Crystal structure of ovalbumin as a model for the reactive centre of serpins. Nature, 347, 99–102.

Strandberg, L., Lawrence, D. A., Johansson, L. B., & Ny, T. (1991). The oxidative inactivation of plasminogen activator inhibitor type 1 results from a conformational change in the molecule and does not require the involvement of the P1' methionine. The Journal of Biological Chemistry, 266, 13852–13858.

Wei, A., Rubin, H., Cooperman, B. S., & Christianson, D. W. (1994). Crystal structure of an uncleaved serpin reveals the conformation of an inhibitory reactive loop. Nature Structural Biology, 1, 251–258.

Wilczynska, M., Fa, M., Ohlsson, P.-I., & Ny, T. (1995). The Inhibition Mechanism of Serpins: Evidence that the mobile reactive center loop is cleaved in the native protease-inhibitor complex. The Journal of Biological Chemistry, 270, 29652–29655.

Wright, H. T., & Scarsdale, J. N. (1995). Structural basis for serpin inhibitor activity. Proteins, 22, 210–225.

York, J. D., Li, P., & Gardell, S. J. (1991). Combinatorial mutagenesis of the reactive site region in plasminogen activator inhibitor I. The Journal of Biological Chemistry, 266, 8495–8500.

A related serpin (CAPE) derived from human hypothalamus is described in W096/40922 published Dec. 19, 1996. This published CAPE serpin differs from the BAIT of the present invention by having 17 of its CAPE amino acids replaced by 23 different BAIT amino acids. Specifically when numbering from the first methionine, HGS Alanine (27) is replaced by CAPE Valine; HGS Aspartic Acid (173) replaces an unknown CAPE amino acid; the six HGS aminoacids 319–324 are replaced in CAPE by 5 different amino acids, and the 15 HGS amino acids 351–365 are replaced by only 10 CAPE amino acids. Thus the BAIT of the present invention contains 23 amino acids in 4 locations that are not found in the CAPE polypeptide.

During the development of the nervous system, neurons form axons which extend along a prespecified path into the target area, where they engage in the formation and refinement of synaptic connections. These stages depend critically on the capability of the axonal growth cones to interact with a variety of structures which they encounter along their way and at their destination. These structures include cell surfaces of neuronal and non-neuronal origin and the extracellular matrix. Along their trajectory and at their target sites, growth cones not only receive and respond to signals from their local environment, but also actively secrete macromolecules. In particular, secreted proteases have been implicated in supporting the growth cone advancement through the tissue. More than a decade ago, it was demonstrated that plasminogen activators are axonally secreted by neurons in culture. Recently, their occurrence in the developing rat nervous system during the period of axon outgrowth has been revealed. Moreover, several pieces of evidence were presented which indicated that serine proteases, such as plasminogen activators or thrombin, are involved in restructuring of the synaptic connectivity during development and regeneration. Such processes include elimination during development and synaptic plasticity associated with learning and memory in the adult. See, for instance, Osterwalder, T., et al., "Neuroserpin, an axonally secreted serine protease inhibitor," *EMBO J.* 15:2944–2953 (1996).

During normal development of the nervous system, about 50% of postmitotic lumbosacral motoneurons undergo naturally occurring (programmed) cell death during a period when these cells are forming synaptic connections with their target muscles. Naturally occurring motoneuron death has been described in many vertebrate species, including chicken, mouse, rat, and human embryos or fetuses. For example, programmed motoneuron death occurs between embryonic day (E)6 and E10 in the chicken. This system has been used as a biological model for testing different neurotrophic agents on motoneuron survival in vivo. See, for instance, Houenou, L. J., et al., "A serine protease inhibitor, protease nexin I, rescues motoneurons from naturally occurring and axotomy-induced cell death," *Proc. Natl. Acad. Sci. USA* 92:895–899 (1995).

Although programmed cell death is completed before birth in mammals, the maintenance of motoneurons continues to be dependent on support from the target for some time after birth. Thus, if transection of motor axons is performed in neonatal mammals and reinnervation is prevented, a large number of motoneurons degenerate and die. Axotomy-induced death of motoneurons has also been extensively used as a model for testing the survival effects of various agents, including neurotrophic and growth factors on motoneurons.

Protease nexin I (PNI), also known as glia-derived nexin, is a 43–47-kDa protein that was first found secreted by cultured fibroblasts but is also produced by glial (glioma and primary) and skeletal muscle cells. PNI has been shown to promote neurite outgrowth from different neuronal cell types. These include neuroblastoma cells, as well as primary hippocampal and sympathetic neurons. The neurite-promoting activity of PNI in vitro is mediated by inhibition of thrombin, a potent serine protease. PNI (mRNA and protein) is transiently up-regulated in rat sciatic nerve after axotomy, and PNI-producing cells are localized distal to the lesion site. This up-regulation of PNI occurs 2–3 days after a similar up-regulation of prothrombin and thrombin in the distal stump. Free PNI protein is significantly decreased, while endogenous PNI-thrombin complexes are increased, in various anatomical brain regions, including hippocampus of patients with Alzheimer disease. When considered together with the recent demonstration that PNI can promote the in vitro survival of mixed mouse spinal chord neurons and that PNI is released from glia cells by neuropeptides such as vasoactive intestinal polypeptide, these observations suggest that PNI may play a physiological role in neuronal survival, differentiation, and/or axonal regeneration in vivo.

Recently, it has been reported that PNI rescues spinal motoneuron death in the neonatal mouse. Houenou, L. J. et al., 1995, supra. The survival effect of PNI on motoneurons during the period of programmed cell death was not associated with increased intramuscular nerve branching. PNI also significantly increased the nuclear size of motoneurons during the period of programmed cell death and prevented axotomy-induced atrophy of surviving motoneurons. These results indicate a possible role of PNI as a neurotrophic agent. They also support the idea that serine proteases or, more precisely, the balance of proteases and serpins may be involved in regulating the fate of neuronal cells during development.

More recently, a cDNA encoding an axonally secreted glycoprotein of central nervous system (CNS) and peripheral nervous system (PNS) neurons of the chicken has been cloned and sequenced. Osterwalder, T., et al., 1996) supra. Analysis of the primary structural features characterized this protein as a novel member of the serpin superfamily which was therefore called "neuroserpin." No demonstration of inhibition of any protease was included in this report, however. In situ hybridization revealed a predominately neuronal expression during the late stages of neurogenesis and in the adult brain in regions which exhibit synaptic plasticity. Thus, it has been suggested that neuroserpin may function as an axonally secreted regulator of the local extracellular proteolysis involved in the reorganization of the synaptic connectivity during development and synapse plasticity in the adult. A role for serine proteases and serpins in neuronal remodeling is further supported by the finding that elevated tPA mRNA and protein levels are found in cerebellar Purkinje neurons of rats undergoing motor learning (Seeds NW; Williams BL; Bickford P. C., "Tissue plasminogen activator induction in Purkinje neurons after cerebellar motor learning." *Science* 270:1992–4 (1995)).

The amplification of a human cDNA fragment of about 450 bp corresponding to the region of the chicken cDNA encoding the putative reactive site loop of the so-called neuroserpin, using a polymerase chain reaction with two pairs of nested primers flanking that region, has also been reported. Osterwalder, T., et al., 1996, supra, page 2946. The authors also reported that the deduced amino acid sequences of the human and corresponding mouse cDNA exhibited a sequence identity of 88% and 87% respectively, with chicken neuroserpin. However, the human DNA sequence in a related serpin derived from human hypothalamus is described in WO96/40922 published Dec. 19, 1996 is about 99% the same as the present invention.

Thus, there is a need for human polypeptides that function as serpins in the regulation of various serine proteases, particularly in the nervous system, since disturbances of such regulation may be involved in disorders relating to hemostasis, angiogenesis, tumor metastisis, cellular migration and ovulation, as well as neurogenesis; and, therefore, there is a need for identification and characterization of such human polypeptides which can play a role in preventing, ameliorating or correcting such disorders.

SUMMARY OF THE INVENTION

The present invention provides isolated nucleic acid molecules comprising a polynucleotide encoding the human BAIT polypeptide having the amino acid sequence shown in FIG. 1 (SEQ ID NO:2) or the amino acid sequence encoded by the cDNA clone deposited in a bacterial host as ATCC Deposit Number 97722 on Sep. 18, 1996. The nucleotide sequence determined by sequencing the deposited BAIT clone, which is shown in FIG. 1 (SEQ ID NO:1), contains an open reading frame encoding a complete polypeptide of 410 amino acid residues, including an initiation codon at positions 89–91, and a predicted molecular weight of about 46.4 kDa. The encoded polypeptide has a leader sequence of 18 amino acids, underlined in FIG. 1; and the amino acid sequence of the expressed mature BAIT protein is also shown in FIG. 1, as amino acid residues 19–410 (SEQ ID NO:2).

The human BAIT protein of the present invention has been shown to exhibit selective inhibition of tissue-type plasminogen activator (t-PA) with relatively little inhibition of trypsin, thrombin or urokinase-type plasminogen activator (u-PA). The human BAIT polypeptide also shares extensive sequence homology with the translation product of the mRNA for a serpin-related protein isolated from brain cDNA library which has been named "neuroserpin" (SEQ ID NO:3) (see FIG. 2). As noted above, neuroserpin in the chicken is thought to play an important an important role in regulation of local extracellular proteolysis involved in the reorganization of the synaptic connectivity during development and synapse plasticity in the adult. The homology between neuroserpin and BAIT (90% amino acid similarity) indicates that BAIT also may play a similar role in neurogenesis in humans.

Thus, one aspect of the invention provides an isolated nucleic acid molecule comprising a polynucleotide having a nucleotide sequence selected from the group consisting of: (a) a nucleotide sequence encoding the BAIT polypeptide having the complete amino acid sequence in FIG. 1 (SEQ ID NO:2); (b) a nucleotide sequence encoding the expressed mature BAIT polypeptide having the amino acid sequence at positions 19–410 in FIG. 1 (SEQ ID NO:2); (c) a nucleotide sequence encoding the BAIT polypeptide having the complete amino acid sequence encoded by the cDNA clone contained in ATCC Deposit No. DEPOSIT; (d) a nucleotide sequence encoding the mature BAIT polypeptide having the amino acid sequence encoded by the cDNA clone contained in ATCC Deposit No. DEPOSIT; and (e) a nucleotide sequence complementary to any of the nucleotide sequences in (a), (b), (c) or (d) above.

Further embodiments of the invention include isolated nucleic acid molecules that comprise a polynucleotide having a nucleotide sequence at least 99.1% identical, and more preferably at least 99.2%, 99.3%, 99.4%, 99.5%, 99.6.%, 99.7%, 99.8% or 99.9% identical, to any of the nucleotide sequences in (a), (b), (c), (d) or (e), above, or a polynucleotide which hybridizes under stringent hybridization conditions to a polynucleotide in (a), (b), (c), (d) or (e), above. This polynucleotide which hybridizes does not hybridize under stringent hybridization conditions to a polynucleotide having a nucleotide sequence consisting of only A residues or of only T residues. An additional nucleic acid embodiment of the invention relates to an isolated nucleic acid molecule comprising a polynucleotide which encodes the amino acid sequence of an epitope-bearing portion of a BAIT polypeptide having an amino acid sequence in (a), (b), (c) or (d), above.

The present invention also relates to recombinant vectors, which include the isolated nucleic acid molecules of the present invention, and to host cells containing the recombinant vectors, as well as to methods of making such vectors and host cells and for using them for production of BAIT polypeptides or peptides by recombinant techniques.

The invention further provides an isolated BAIT polypeptide having an amino acid sequence selected from the group consisting of: (a) the amino acid sequence of the BAIT polypeptide having the complete amino acid sequence including the leader sequence shown in FIG. 1 (SEQ ID NO:2); (b) the amino acid sequence of the mature BAIT polypeptide (without the leader) having the amino acid sequence at positions 19–410 in FIG. 1 (SEQ ID NO:2); (c) the amino acid sequence of the BAIT polypeptide having the complete amino acid sequence, including the leader, encoded by the cDNA clone contained in ATCC Deposit No. 97722; and (d) the amino acid sequence of the mature BAIT polypeptide having the amino acid sequence encoded by the cDNA clone contained in ATCC Deposit No. 97722 The polypeptides of the present invention also include polypeptides having an amino acid sequence at least 95% identical, more preferably at least 96% identical, and still more preferably 97%, 98% or 99% identical to those described in (a), (b), (c) or (d) above, as well as polypeptides having an amino acid sequence with at least 96% similarity, and more preferably at least 97%, 98% or 99% similarity, to those above.

An additional embodiment of this aspect of the invention relates to a peptide or polypeptide which has the amino acid sequence of an epitope-bearing portion of a BAIT polypeptide having an amino acid sequence described in (a), (b), (c) or (d), above. Peptides or polypeptides having the amino acid sequence of an epitope-bearing portion of a BAIT polypeptide of the invention include portions of such polypeptides with at least six or seven, preferably at least nine, and more preferably at least about 30 amino acids to about 50 amino acids, although epitope-bearing polypeptides of any length up to and including the complete amino acid sequence of a polypeptide of the invention described above also are included in the invention.

In another embodiment, the invention provides an isolated antibody that binds specifically to a BAIT polypeptide having an amino acid sequence described in (a), (b), (c) or (d) above. The invention further provides methods for isolating antibodies that bind specifically to a BAIT polypeptide having an amino acid sequence as described herein. Such antibodies are useful diagnostically or therapeutically as described below.

The present invention also provides a screening method for identifying compounds capable of enhancing or inhibiting a biological activity of the BAIT polypeptide, which involves contacting a protease which is inhibited by the BAIT polypeptide with the candidate compound in the presence of a partially inhibitory amount of BAIT polypeptide, assaying proteolytic activity of the protease on a susceptible substrate in the presence of the candidate compound and partially inhibitory amount of BAIT polypeptide, and comparing the proteolytic activity to a standard level of activity, the standard being assayed when contact is made between the protease and its substrate in the presence of the partially inhibitory amount of BAIT polypeptide and the absence of the candidate compound. In this assay, an increase in inhibition of proteolytic activity over the standard indicates that the candidate compound is an agonist of BAIT inhibitory activity and a decrease in inhibition of proteolytic activity compared to the standard indicates that the compound is an antagonist of BAIT inhibitory activity.

In another aspect, a screening assay for agonists and antagonists is provided which involves determining the effect a candidate compound has on BAIT binding to the active site of a susceptible protease. In particular, the method involves contacting the BAIT-susceptible protease with a BAIT polypeptide and a candidate compound and determining whether BAIT polypeptide binding to the BAIT-susceptible protease is increased or decreased due to the presence of the candidate compound.

The present inventor has discovered that BAIT is expressed in whole human brain, and to a much lesser extent in adult pancreas and adult heart. For a number of disorders of the central or peripheral nervous system, significantly higher or lower levels of BAIT gene expression may be detected in certain tissues (e.g., adult brain, embryonic retina, cerebellum and spinal chord) or bodily fluids (e.g., serum, plasma, urine, synovial fluid or spinal fluid) taken from an individual having such a disorder, relative to a "standard" BAIT gene expression level, i.e., the BAIT expression level in healthy tissue from an individual not having the nervous system disorder. Thus, the invention provides a diagnostic method useful during diagnosis of nervous system disorders, which involves: (a) assaying BAIT gene expression level in cells or body fluid of an individual; (b) comparing the BAIT gene expression level with a standard BAIT gene expression level, whereby an increase or decrease in the assayed BAIT gene expression level compared to the standard expression level is indicative of disorder in the nervous system.

An additional aspect of the invention is related to a method for treating an individual in need of an increased level of BAIT activity in the body (i.e., insufficient protease inhibitory activity of BAIT and/or excessive protease activity of a protease inhabited by BAIT, particularly t-PA), which method comprises administering to such an individual a composition comprising a therapeutically effective amount of an isolated BAIT polypeptide of the invention or an agonist thereof.

A still further aspect of the invention is related to a method for treating an individual in need of a decreased level of BAIT activity in the body (i.e., less inhibition of a protease susceptible to BAIT) comprising, administering to such an individual a composition comprising a therapeutically effective amount of a BAIT antagonist. Preferred antagonists for use in the present invention are BAIT-specific antibodies.

BRIEF DESCRIPTION OF THE FIGURES

FIG. 1 shows the nucleotide sequence (SEQ ID NO:1) and deduced amino acid sequence (SEQ ID NO:2) of the human BAIT polypeptide. The leader sequence of 18 amino acids is underlined.

FIG. 2 shows the regions of identity between the amino acid sequences of the human BAIT protein and other indicated serpins with which the human BAIT polypeptide shares significant homology, as follows: bovine plasminogen activator inhibitor-1 (BovPAI1; SEQ ID NO:4); rat glial-derived nexin I (RatGDNI; SEQ ID NO:5); mouse antithrombin III (MusATIII; SEQ ID NO:6); chicken neuroserpin (ChkNSP;SEQ ID NO:3). The sequence alignment was generated with the Pileup module of the Genetics Computer Group (Wisconsin Package, Version 8, using the parameters GapWeight=3.000, GapLengthWeight=0.100). The reactive site loops (from positions 415–452 in FIG. 2 (corresponding to BAIT residues 342–378 in FIG. 1; SEQ ID NO:2) are double-underlined, and critical positions in this sequence are labeled $P_{17}$ to $P_1$ and $P_1'$ according to Schechter and Berger, Biochem. Biopys. Res. Commun. 27:157–162 (1967). The putative reactive site (cleaved by a target protease), between Arg at BAIT position 362 and Met at BAIT position 363, is marked with an arrow ().

FIG. 4 shows the relationship between the deposited cDNA clone (identified as clone HSDFB5501X; SEQ ID NO:1) and three related cDNA clones of the invention, designated HPBCT06R (SEQ ID NO:7), HPBDG64R (SEQ ID NO:8), and HPBCR79R (SEQ ID NO:9).

DETAILED DESCRIPTION

Figure 1:
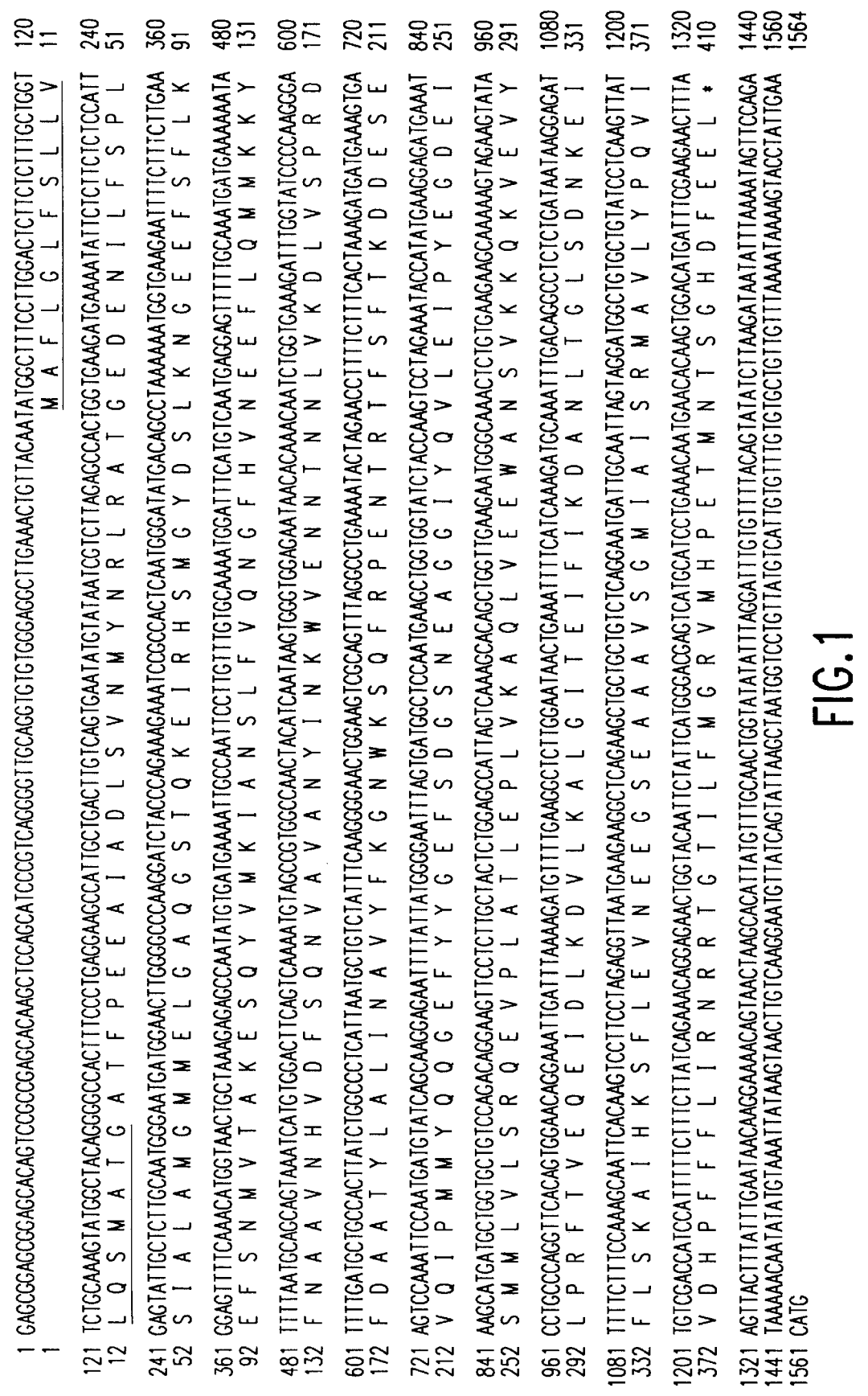
Figure 3:
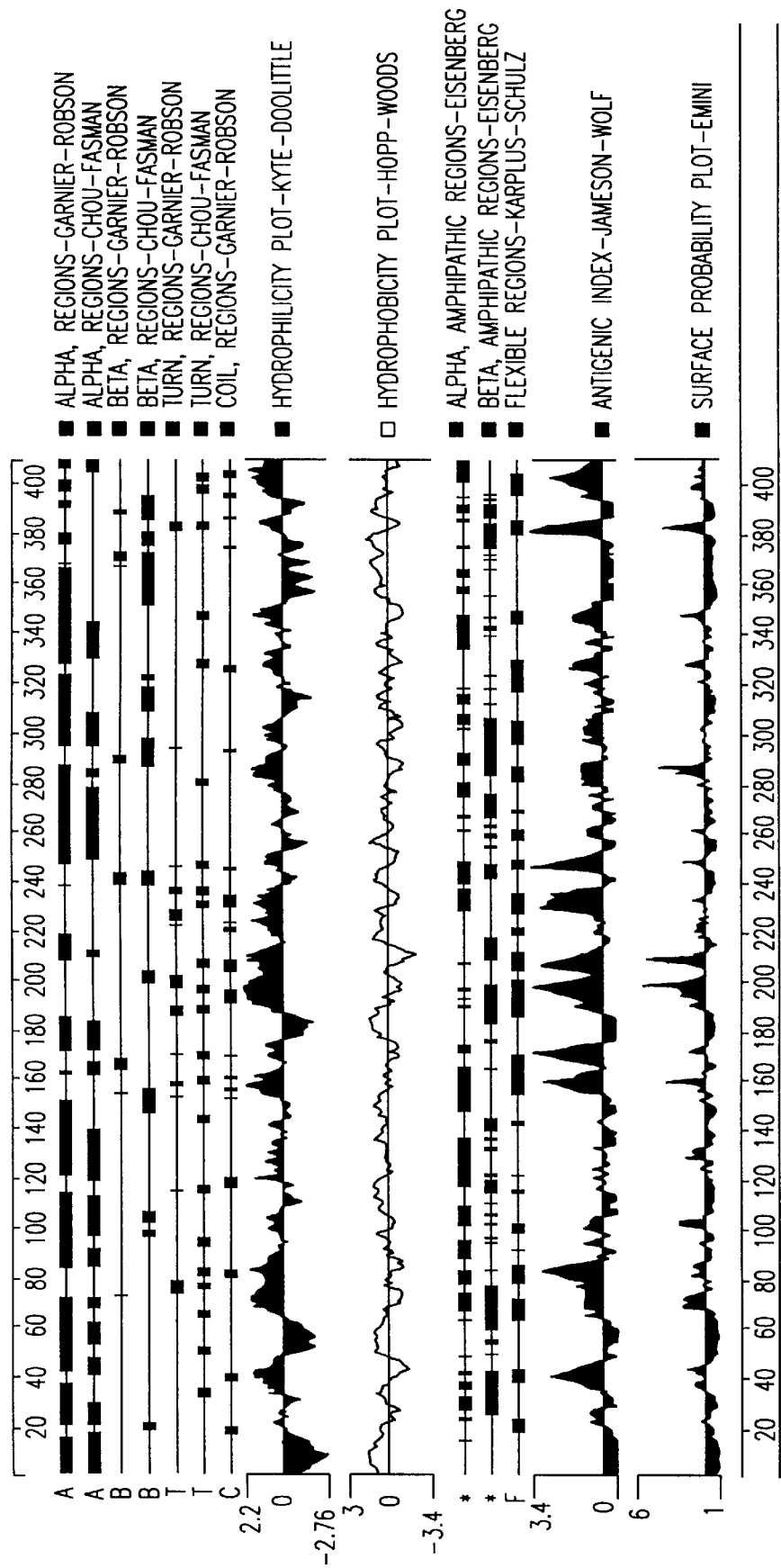
FIG. 3 shows an analysis of the BAIT amino acid sequence. Alpha, beta, turn and coil regions; hydrophilicity and hydrophobicity; amphipathic regions; flexible regions; antigenic index and surface probability are shown. In the "Antigenic Index-Jameson-Wolf" graph, the location of the highly antigenic regions of the BAIT protein, i.e., regions from which epitope-bearing peptides of the invention may be obtained.

The present invention provides isolated nucleic acid molecules comprising a polynucleotide encoding a human BAIT polypeptide having the amino acid sequence shown in FIG. 1 (SEQ ID NO:2), which was determined by sequencing a cloned cDNA. The nucleotide sequence shown in FIG. 1 (SEQ ID NO:1) was obtained by sequencing the HSDFB55SO1 clone, which was deposited on Sep. 18, 1996 at the American Type Culture Collection, 10801 University Boulevard, Manassas, Va. 20110-2209, and given accession number ATCC 97722. The strain is maintained under the terms of the Budapest Treaty and will be made available to a patent office signatory to the Budapest Treaty. The deposited clone is contained in the pBluescript SK(−) plasmid (Stratagene, La Jolla, Calif.).

Nucleic Acid Molecules

Unless otherwise indicated, all nucleotide sequences determined by sequencing a DNA molecule herein were determined using an automated DNA sequencer (such as the Model 373 from Applied Biosystems, Inc., Foster City, Calif.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 99% identical, more typically at least about 99.1% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Unless otherwise indicated, each "nucleotide sequence" set forth herein is presented as a sequence of deoxyribonucleotides (abbreviated A, G, C and T). However, by "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U). For instance, reference to an RNA molecule having the sequence of SEQ ID NO:1 set forth using deoxyribonucleotide abbreviations is intended to indicate an RNA molecule having a sequence in which each deoxyribonucleotide A, G or C of SEQ ID NO:1 has been replaced by the corresponding ribonucleotide A, G or C, and each deoxyribonucleotide T has been replaced by a ribonucleotide U. Using the information provided herein, such as the nucleotide sequence in FIG. 1, a nucleic acid molecule of the present invention encoding a BAIT polypeptide may be obtained using standard cloning and screening procedures, such as those for cloning cDNAs using mRNA as starting material. Illustrative of the invention, the nucleic acid molecule described in FIG. 1 (SEQ ID NO:1) was discovered in a cDNA library derived from whole human brain. Additional cDNA clones of the BAIT gene were also identified in cDNA libraries from the following tissues: spinal cord, pineal gland and adrenal gland tumor.

Figure 2A:
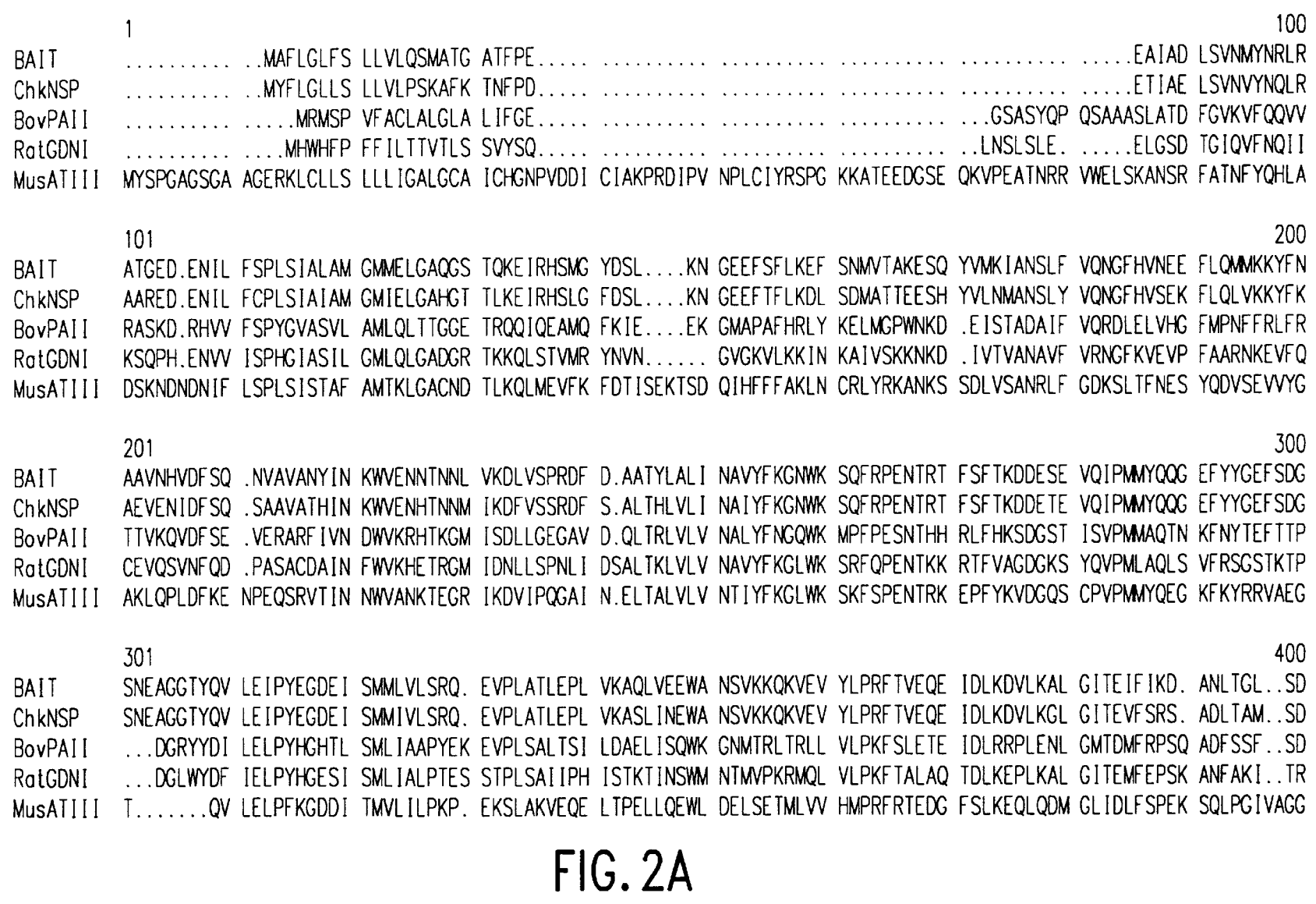

The determined nucleotide sequence of the BAIT cDNA of FIG. 1 (SEQ ID NO:1) contains an open reading frame encoding a protein of 410 amino acid residues, with an initiation codon at positions 89–91, and a predicted molecular weight of about 46.4 kDa. The encoded polypeptide has a leader sequence of 18 amino acids, underlined in FIG. 1; and the amino acid sequence of the expressed mature BAIT protein is also shown in FIG. 1, as amino acid residues 19–410 (SEQ ID NO:2). The amino acid sequence of the BAIT protein shown in FIG. 1 (SEQ ID NO:2) is about 80% identical to the published mRNA for chicken neuroserpin (Osterwalder, T., et al., 1996, supra) as shown in FIG. 2. FIG. 2 shows the regions of identity between the amino acid sequences of the human BAIT protein and other indicated serpins with which the human BAIT polypeptide shares significant homology, as follows: bovine plasminogen activator inhibitor-1 (BovPAI1; SEQ ID NO:4); rat glial-derived nexin I.(RatGDNI; SEQ ID NO:5); mouse antithrombin III (MusATIII; SEQ ID NO:6); chicken neuroserpin (ChkNSP;SEQ ID NO:3).

Sequence comparisons suggest that the chicken neuroserpin and BAIT are orthologs of one another and are distantly related to the better characterized mammalian serpins seen in FIG. 2. There is 77% homology at the DNA level between BAIT and neuroserpin which translates into 90% and 80% amino acid similarity and identity, respectively. Amino acid identities between the non-human mammalian serpins and BAIT drop to about 30%. Moreover, within the functionally important reactive site loop, there is only one conservative amino acid change between BAIT and neuroserpin. There are 7 non-conservative changes between BAIT and PAI-1 in the same 38 amino acid region. The active site P1-P1' residues, however, are perfectly conserved between BAIT, neuroserpin, and PAI-1. The BAIT region corresponding to the ATIII heparin-binding site has 4 acidic amino acids which implies that heparin is not a co-factor as it is with ATIII. One potentially significant difference between BAIT and neuroserpin is the presence of 3 consensus N-linked glycosylation sites in the former versus 2 in the latter. Thus, BAIT and neuroserpin are likely to have similar enzymatic properties which may not overlap those of the related serpins.

Leader and Mature Sequences

The amino acid sequence of the complete BAIT protein includes a leader sequence and a mature protein, as shown in FIG. 1 (SEQ ID NO:2). More in particular, the present invention provides nucleic acid molecules encoding one or more mature form(s) of the BAIT protein. Thus, according to the signal hypothesis, proteins secreted by mammalian cells have a signal or secretory leader sequence which is cleaved from the mature protein once export of the growing protein chain across the rough endoplasmic reticulum has been initiated. Most mammalian cells and even insect cells cleave secreted proteins with the same specificity. However, in some cases, cleavage of a secreted protein is not entirely uniform, which results in two or more mature species of the protein. Further, it has long been known that the cleavage specificity of a secreted protein is ultimately determined by the primary structure of the complete protein, that is, it is inherent in the amino acid sequence of the polypeptide. Therefore, the present invention provides a nucleotide sequence encoding the mature BAIT polypeptide having the amino acid sequence encoded by the cDNA clone contained in the host identified as ATCC Deposit No. 97722. By the "mature BAIT polypeptide having the amino acid sequence encoded by the cDNA clone in ATCC Deposit No. 97722" is meant the mature form(s) of the BAIT protein produced by expression in a mammalian cell (e.g., COS cells, as described below) of the complete open reading frame encoded by the human DNA sequence of the clone contained in the vector in the deposited host.

In the present case, the deposited cDNA has been expressed in insect cells using a baculovirus expression vector, as described hereinbelow; and amino acid sequencing of the amino terminus of the secreted species indicated that the N-terminus of the mature BAIT protein comprises the amino acid sequence beginning at amino acid 19 of FIG. 1 (SEQ ID NO:2). Thus, the leader sequence of the BAIT protein in the amino acid sequence of FIG. 1 is 18 amino acids, from position 1 to 18 in FIG. 1 (SEQ ID NO:2).

The predicted 410 amino acids of the complete BAIT (prepro) polypeptide is expected to yield a 46.4 kDa band. The observed doublet band of 45 and 46 kDa upon expression in the baculovirus system was within the expected size range when the putative 18 amino acid signal peptide is removed. The approximate 1 kDa difference in the observed doublet bands may be explained by differential glycosylation. Evidence to support this includes the three consensus N-linked glycosylation site present in the nucleotide sequence (FIG. 1) and the presence of oligosaccharide moieties on the purified protein determined experimentally.

N-Terminal and C-terminal Deletion Mutants

In addition to the mature form of a protein being biologically active, it is known in the art for many proteins, including the mature form(s) of a secreted protein, that one or more amino acids may be deleted from the N-terminus without substantial loss of biological function. In the present case, deletions of at least up to 30 N-terminal amino acids from the end of the mature (secreted) polypeptide may retain some biological activity such as binding to the active site of at least one protease. However, even if deletion of one or more amino acids from the N-terminus of a protein results in modification of loss of one or more biological functions of the protein, other biological activities may still be retained. Thus, the ability of the shortened protein to induce and/or binding to antibodies which recognize the complete or mature protein generally will be retained when less than the majority of the residues of the complete or mature protein are removed from the N-terminus. Whether a particular polypeptide lacking N-terminal residues of a complete protein retains such immunologic activities can readily be determined by routine methods described herein and otherwise known in the art. Similarly, deletion of one or more amino acids from the C-terminus of a protein also may provide shortened polypeptides which retain some or all biological activities.

In the baculovirus expression system the BAIT polypeptide was processed to produce multiple forms of BAIT. Beginning after the 18 amino acid leader, the next amino acids found on the baculovirus processed BAIT are as follows:

Ala-Thr-Phe-Pro-Glu (residues 1–5 of SEQ ID NO:2)
Thr-Phe-Pro-Glu-Glu (residues 2–6 of SEQ ID NO:2)
Phe-Pro-Glu-Glu-Ala (residues 3–7 of SEQ ID NO:2)

These are found within the first 7 amino acids of the mature BAIT in FIG. 1. Therefor, there are multiple different N-terminal amino acids on the BAIT produced in the Baculovirus system.

Accordingly, the present invention further provides polypeptides having one or more residues from the amino terminus of the amino acid sequence of the complete BAIT polypeptide in SEQ ID NO:2, up to 30 residues from the amino terminus after the leader cleavage site described above, and polynucleotides encoding such polypeptides. In particular, the present invention provides polypeptides having the amino acid sequence of residues n-410 of the amino acid sequence in SEQ ID NO:2, where n is any integer in the range of 2–49 specified range and 49 is the position of the 30th residue from the N-terminus of the mature polypeptide, after the above leader cleavage site, as shown in the amino acid sequence in SEQ ID NO:2. More in particular, the invention provides polypeptides having the amino acid sequence of residues 2–410, 3–410, 4–410, 5–410, 6–410, 7–410, 8–410, 9–410, 10–410, 11–410, 12–410, 13–410, 14–410, 15–410, 16–410, 17–410, 18–410, 19–410, 20–410, 21–410, 22–410, 23–410, 24–410, 25–410, 26–410, 27–410, 28–410, 29–410, 30–410, 31–410, 32–410, 33–410, 34–410, 35–410, 36–410, 37–410, 38–410, 39–410, 40–410, 41–410, 42–410, 43–410, 44–410, 45–410, 46–410, 47–410, 48–410 and 49–410 of SEQ ID NO:2. Polynucleotides encoding these polypeptides also are provided.

Similarly, the present invention further provides polypeptides having one or more residues from the carboxyl terminus of the amino acid sequence of the complete BAIT polypeptide in SEQ ID NO:2, up to 30 residues from the carboxyl terminus, and polynucleotides encoding such polypeptides. In particular, the present invention provides polypeptides having the amino acid sequence of residues 1-m of the amino acid sequence in SEQ ID NO:2, where m is any integer in the range of 381–409, as shown in the amino acid sequence in SEQ ID NO:2. More in particular, the invention provides polypeptides having the amino acid sequence of residues 1–381, 1–382, 1–383, 1–384, 1–385, 1–386, 1–387, etc. up to 1–408 of SEQ ID NO:2. Polynucleotides encoding these polypeptides also are provided. In addition, polypeptides (and polynucleotides encoding these) having both N-terminal and C-terminal deletions together, of the general formula n-m of SEQ ID NO:2 are included, where n and m are integers as defined above.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules, produced synthetically.

Isolated nucleic acid molecules of the present invention include DNA molecules comprising an open reading frame (ORF) with an initiation codon at positions 89–91 of the nucleotide sequence shown in FIG. 1 (SEQ ID NO:1); DNA molecules comprising the coding sequence for the mature BAIT protein shown in FIG. 1 (amino acids 19–410) (SEQ ID NO:2); and DNA molecules which comprise a sequence substantially different from those described above but which, due to the degeneracy of the genetic code, still encode the BAIT protein. Of course, the genetic code is well known in the art. Thus, it would be routine for one skilled in the art to generate the degenerate variants described above.

In another aspect, the invention provides isolated nucleic acid molecules encoding the BAIT polypeptide having an amino acid sequence encoded by the cDNA clone contained in the plasmid deposited as ATCC Deposit No. 97722. Preferably, this nucleic acid molecule will encode the mature polypeptide encoded by the above-described deposited cDNA clone. The invention further provides an isolated nucleic acid molecule having the nucleotide sequence shown in FIG. 1 (SEQ ID NO:1) or the nucleotide sequence of the BAIT cDNA contained in the above-described deposited clone, or a nucleic acid molecule having a sequence complementary to one of the above sequences. Such isolated molecules, particularly DNA molecules, are useful as probes for gene mapping, by in situ hybridization with chromosomes, and for detecting expression of the BAIT gene in human tissue, for instance, by Northern blot analysis.

The present invention is further directed to nucleic acid molecules encoding portions of the nucleotide sequences described herein as well as to fragments of the isolated nucleic acid molecules described herein. In particular, the invention provides a polynucleotide having a nucleotide sequence representing the portion of SEQ ID NO:1 which consists of positions 1–410 of SEQ ID NO:1. In addition, the invention provides nucleic acid molecules having related nucleotide sequences determined from the following related cDNA clones: HPBCT06R (SEQ ID NO:7), HBPDG64R (SEQ ID NO:8), and HPBCR79R (SEQ ID NO:9); see FIG. 4. More generally, by a fragment of an isolated nucleic acid molecule having the nucleotide sequence of the deposited cDNA or the nucleotide sequence shown in FIG. 1 (SEQ ID NO:1) is intended fragments at least about 15 nt, and more preferably at least about 20 nt, still more preferably at about 30 nt, and even more preferably, at least about 40 nt in length which are useful as diagnostic probes and primers as discussed herein. Of course, larger fragments 50–300 nt in length are also useful according to the present invention as are fragments corresponding to most, if not all, of the nucleotide sequence of the deposited cDNA or as shown in FIG. 1 (SEQ ID NO:1). By a fragment at least 20 nt in length, for example, is intended fragments which include 20 or more contiguous bases from the nucleotide sequence of the deposited cDNA or the nucleotide sequence as shown in FIG. 1 (SEQ ID NO:1). Since the gene has been deposited and the nucleotide sequence shown in FIG. 1 (SEQ ID NO:1) is provided, generating such DNA fragments would be routine to the skilled artisan. For example, restriction endonuclease cleavage or shearing by sonication could easily be used to generate fragments of various sizes. Alternatively, such fragments could be generated synthetically.

Preferred nucleic acid fragments of the present invention include nucleic acid molecules encoding epitope-bearing portions of the BAIT polypeptide as identified in FIG. 3 and described in more detail below.

In another aspect, the invention provides an isolated nucleic acid molecule comprising a polynucleotide which hybridizes under stringent hybridization conditions to a portion of the polynucleotide in a nucleic acid molecule of the invention described above, for instance, the cDNA clone contained in ATCC Deposit 97722. By "stringent hybridization conditions" is intended overnight incubation at 42 C. in a solution comprising: 50% formamide, 5× SSC (150 mM NaCl, 15 mM trisodium citrate), 50 mM sodium phosphate (pH 7.6), 5× Denhardt's solution, 10% dextran sulfate, and 20 g/ml denatured, sheared salmon sperm DNA, followed by washing the filters in 0.1× SSC at about 65 C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 50–70 nt of the reference polynucleotide. These are useful as diagnostic probes and primers as discussed above and in more detail below.

Of course, polynucleotides hybridizing to a larger portion of the reference polynucleotide (e.g., the deposited cDNA clone), for instance, a portion 50–300 nt in length, or even to the entire length of the reference polynucleotide, are also useful as probes according to the present invention, as are polynucleotides corresponding to most, if not all, of the nucleotide sequence of the deposited cDNA or the nucleotide sequence as shown in FIG. 1 (SEQ ID NO:1). By a portion of a polynucleotide of "at least 20 nt in length," for example, is intended 20 or more contiguous nucleotides from the nucleotide sequence of the reference polynucleotide (e.g., the deposited cDNA or the nucleotide sequence as shown in FIG. 1 (SEQ ID NO:1)). As indicated, such portions are useful diagnostically either as a probe according to conventional DNA hybridization techniques or as primers for amplification of a target sequence by the polymerase chain reaction (PCR), as described, for instance, in *Molecular Cloning, A Laboratory Manual,* 2nd. edition, Sambrook, J., Fritsch, E. F. and Maniatis, T., eds., Cold Spring Harbor Laboratory Press, Cold Spring Harbor, N.Y. (1989), the entire disclosure of which is hereby incorporated herein by reference.

Since a BAIT cDNA clone has been deposited and its determined nucleotide sequence is provided in FIG. 1 (SEQ ID NO:1), generating polynucleotides which hybridize to a portion of the BAIT cDNA molecule would be routine to the skilled artisan. For example, restriction endonuclease cleavage or shearing by sonication of the BAIT cDNA clone could easily be used to generate DNA portions of various sizes which are polynucleotides that hybridize to a portion of the BAIT cDNA molecule. Alternatively, the hybridizing polynucleotides of the present invention could be generated synthetically according to known techniques. Of course, a polynucleotide which hybridizes only to a poly A sequence (such as the 3 terminal poly(A) tract of the BAIT cDNA shown in FIG. 1 (SEQ ID NO:1)), or to a complementary stretch of T (or U) residues, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

As indicated, nucleic acid molecules of the present invention which encode a BAIT polypeptide may include, but are not limited to those encoding the amino acid sequence of the mature polypeptide, by itself; the coding sequence for the mature polypeptide and additional sequences, such as those encoding the about 18 amino acid leader or secretory sequence, such as a pre-, or pro- or prepro- protein sequence; the coding sequence of the mature polypeptide, with or without the aforementioned additional coding sequences, together with additional, non-coding sequences, including for example, but not limited to introns and non-coding, 5' and 3' sequences, such as the transcribed, non-translated sequences that play a role in transcription, mRNA processing, including splicing and polyadenylation signals, for example—ribosome binding and stability of mRNA; an additional coding sequence which codes for additional amino acids, such as those which provide additional functionalities.

Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (QIAGEN, Inc.), among others, many of which are commercially available. As described in Gentz et al., *Proc. Natl. Acad. Sci. LISA* 86:821–824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37:767 (1984). As discussed below, other such fusion proteins include the BAIT fused to Fc at the N- or C-terminus.

The present invention further relates to variants of the nucleic acid molecules of the present invention, which encode portions, analogs or derivatives of the BAIT protein. Variants may occur naturally, such as a natural allelic variant. By an "allelic variant" is intended one of several alternate forms of a gene occupying a given locus on a chromosome of an organism. *Genes II*, Lewin, B., ed., John Wiley & Sons, New York (1985). Non-naturally occurring variants may be produced using art-known mutagenesis techniques.

Such variants include those produced by nucleotide substitutions, deletions or additions. The substitutions, deletions or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the BAIT protein or portions thereof. Also especially preferred in this regard are conservative substitutions. Most highly preferred are nucleic acid molecules encoding the mature protein having the amino acid sequence shown in FIG. 1 (SEQ ID NO:2) or the mature BAIT amino acid sequence encoded by the deposited cDNA clone.

Further embodiments of the invention include isolated nucleic acid molecules comprising a polynucleotide having a nucleotide sequence at least 99% identical, and more preferably at least 99.1% identical to (a) a nucleotide sequence encoding the full-length BAIT polypeptide having the complete amino acid sequence in FIG. 1 (SEQ ID NO:2), including the leader sequence; (b) a nucleotide sequence encoding the mature BAIT polypeptide (full-length polypeptide with the leader removed) having the amino acid sequence at positions 19–94 in FIG. 1 (SEQ ID NO:2); (c) a nucleotide sequence encoding the full-length BAIT polypeptide having the complete amino acid sequence including the leader encoded by the cDNA clone contained in ATCC Deposit No. 97722; (d) a nucleotide sequence encoding the mature BAIT polypeptide having the amino acid sequence encoded by the cDNA clone contained in ATCC Deposit No. 97722; or (e) a nucleotide sequence complementary to any of the nucleotide sequences in (a), (b), (c) or (d).

By a polynucleotide having a nucleotide sequence at least, for example, 99% "identical" to a reference nucleotide sequence encoding a BAIT polypeptide is intended that the nucleotide sequence of the polynucleotide is identical to the reference sequence except that the polynucleotide sequence may include up to one point mutations per each 100 nucleotides of the reference nucleotide sequence encoding the BAIT polypeptide. In other words, to obtain a polynucleotide having a nucleotide sequence at least 99% identical to a reference nucleotide sequence, up to 1% of the nucleotides in the reference sequence may be deleted or substituted with another nucleotide, or a number of nucleotides up to 1% of the total nucleotides in the reference sequence may be inserted into the reference sequence. These mutations of the reference sequence may occur at the 5 or 3 terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 99.1%, to 99.9% identical to, for instance, the nucleotide sequence shown in FIG. 1 or to the nucleotides sequence of the deposited cDNA clone can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2:482–489 (1981), to find the best segment of homology between two sequences. When using Bestfit or any other sequence alignment program to determine whether a particular sequence is, for instance, 99% identical to a reference sequence according to the present invention, the parameters are set, of course, such that the percentage of identity is calculated over the full length of the reference nucleotide sequence and that gaps in homology of up to 1% of the total number of nucleotides in the reference sequence are allowed.

The present application is directed to nucleic acid molecules at least 96%, 96.1%, 96.2%, 96.3% to 99.9% identical to the nucleic acid sequence shown in FIG. 1 (SEQ ID NO:1) or to the nucleic acid sequence of the deposited cDNA, irrespective of whether they encode a polypeptide having BAIT activity. This is because even where a particular nucleic acid molecule does not encode a polypeptide having BAIT activity one of skill in the art would still know how to use the nucleic acid molecule, for instance, as a hybridization probe or a polymerase chain reaction (PCR) primer. Uses of the nucleic acid molecules of the present invention that do not encode a polypeptide having BAIT activity include, inter alia, (1) isolating the BAIT gene or allelic variants thereof in a cDNA library; (2) in situ hybridization (e.g., "FISH") to metaphase chromosomal spreads to provide precise chromosomal location of the BAIT gene, as described in Verma et al., Human Chromosomes: A Manual of Basic Techniques, Pergamon Press, New York (1988); and Northern Blot analysis for detecting BAIT mRNA expression in specific tissues.

Preferred, however, are nucleic acid molecules having sequences at least 99%, to 99.9% identical to the nucleic acid sequence shown in FIG. 1 (SEQ ID NO:1) or to the nucleic acid sequence of the deposited cDNA which do, in fact, encode a polypeptide having BAIT protein activity. By "a polypeptide having BAIT activity" is intended polypeptides exhibiting activity similar, but not necessarily identical, to an activity of the BAIT protein of the invention (either the full-length protein or, preferably, the mature protein), as measured in a particular biological assay. For example, the BAIT protein of the present invention inhibits the proteolytic activity of tissue-type plasminogen activator (t-PA). Briefly, the assay involves measuring the inhibitory activity against various proteases, particularly tPA, using a single step chromogenic assay essentially as described (Lawrence, Strandberg, Ericson, & Ny, "Structure-function studies of the SERPIN plasminogen activator inhibitor type 1: analysis of chimeric strained loop mutants." J. Biol. Chem. 265: 20293–20301).

BAIT protein inhibits proteolytic activity of t-PA in a dose-dependent manner in the above-described assay. Thus, "a polypeptide having BAIT protein activity" includes polypeptides that also exhibit any of the same t-PA-inhibiting activities in the above-described assay in a dose-dependent manner. Although the degree of dose-dependent activity need not be identical to that of the BAIT protein, preferably, "a polypeptide having BAIT protein activity" will exhibit substantially similar dose-dependence in a given activity as compared to the BAIT protein (i.e., the candidate polypeptide will exhibit greater activity or not more than about 25-fold less and, preferably, not more than about tenfold less activity relative to the reference BAIT protein).

Of course, due to the degeneracy of the genetic code, one of ordinary skill in the art will immediately recognize that a large number of the nucleic acid molecules having a sequence at least 99% identical to the nucleic acid sequence of the deposited cDNA or the nucleic acid sequence shown in FIG. 1 (SEQ ID NO:1) will encode a polypeptide "having BAIT protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having BAIT protein activity. This is because the skilled artisan is fully aware of amino acid substitutions that are either less likely or not likely to significantly effect protein function (e.g., replacing one aliphatic amino acid with a second aliphatic amino acid), as further described below.

Vectors and Host Cells

The present invention also relates to vectors which include the isolated DNA molecules of the present invention, host cells which are genetically engineered with the recombinant vectors, and the production of BAIT polypeptides or fragments thereof by recombinant techniques. The vector may be, for example, a phage, plasmid, viral or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

Preferred are vectors comprising cis-acting control regions to the polynucleotide of interest. Appropriate trans-acting factors may be supplied by the host, supplied by a complementing vector or supplied by the vector itself upon introduction into the host.

In certain preferred embodiments in this regard, the vectors provide for specific expression, which may be inducible and/or cell type-specific. Particularly preferred among such vectors are those inducible by environmental factors that are easy to manipulate, such as temperature and nutrient additives.

Expression vectors useful in the present invention include chromosomal-, episomal- and virus-derived vectors, e.g., vectors derived from bacterial plasmids, bacteriophage, yeast episomes, yeast chromosomal elements, viruses such as baculoviruses, papova viruses, vaccinia viruses, adenoviruses, fowl pox viruses, pseudorabies viruses and retroviruses, and vectors derived from combinations thereof, such as cosmids and phagemids.

The DNA insert should be operatively linked to an appropriate. Among known bacterial promoters suitable for use in the present invention include the E. coli lacI and lacZ promoters, the T3 and T7 promoters, the gpt promoter, the phage lambda PR and PL promoters, the phoA promoter and the trp promoter. Suitable eukaryotic promoters include the CMV immediate early promoter, the HSV thymidine kinase promoter, the early and late SV40 promoters, the promoters of retroviral LTRs, such as those of the Rous sarcoma virus (RSV), and metallothionein promoters, such as the mouse metallothionein-I promoter. Other suitable promoters will be known to the skilled artisan.

The expression constructs will further contain sites for transcription initiation, termination and, in the transcribed region, a ribosome binding site for translation. The coding portion of the mature transcripts expressed by the constructs will preferably include a translation initiating at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in E. coli and other bacteria. Representative examples of appropriate hosts include, but are not limited to, bacterial cells, such as E. coli, Streptomyces and Salmonella typhimurium cells; fungal cells, such as yeast cells; insect cells such as Drosophila S2 and Spodoptera Sf9 cells; animal cells such as CHO, COS, 293 and Bowes melanoma cells; and plant cells. Appropriate culture mediums and conditions for the above-described host cells are known in the art.

Among vectors preferred for use in bacteria include pQE70, pQE60 and pQE-9, available from QIAGEN; pBS vectors, Phagescript vectors, Bluescript vectors, pNH8A, pNH16a, pNH18A, pNH46A, available from Stratagene; and ptrc99a, pKK223–3, pKK233–3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Recombinant constructs may be introduced into host cells using well known techniques such as infection, transduction, transfection, transvection, electroporation and transformation. For instance, introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods In Molecular Biology* (1986).

Transcription of the DNA encoding the polypeptides of the present invention by higher eukaryotes may be increased by inserting an enhancer sequence into the vector. Enhancers are cis-acting elements of DNA, usually about from 10 to 300 bp in length that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, immunoglobulin enhancer and adenovirus enhancers.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to stabilize and purify proteins. For example, EP-A-O 464 533 (Canadian counterpart 2045869) discloses fusion proteins comprising various portions of constant region of immunoglobulin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as hIL-5 has been fused with Fc portions for the purpose of high-throughput screening assays to identify antagonists of hIL-5. See, D. Bennett et al., *Journal of Molecular Recognition* 8:52–58 (1995) and K. Johanson et al., *The Journal of Biological Chemistry* 270:9459–9471 (1995).

Peptides and polypeptides of the present invention can be produced by chemical synthetic procedures known to those of ordinary skill in the art. For example, polypeptides up to about 80–90 amino acid residues in length may be produced on a commercially available peptide synthesizer model 433A (Applied Biosystems, Inc., Foster City, Calif.). Thus, as will be readily appreciated, the full-length mature BAIT polypeptide can be produced synthetically.

The BAIT protein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

BAIT Polypeptides and Fragments

The invention further provides an isolated BAIT polypeptide having the amino acid sequence encoded by the deposited cDNA, or the amino acid sequence in FIG. 1 (SEQ ID NO:2), or a peptide or polypeptide comprising a portion of the above polypeptides. The terms "peptide" and "oligopeptide" are considered synonymous (as is commonly recognized) and each term can be used interchangeably as the context requires to indicate a chain of at least two amino acids coupled by peptidyl linkages. The word "polypeptide" is used herein for chains containing more than ten amino acid residues. All oligopeptide and polypeptide formulas or sequences herein are written from left to right and in the direction from amino terminus to carboxy terminus.

In addition to mature and N-terminal deletion forms of the protein discussed above, it will be recognized by one of ordinary skill in the art that some amino acid sequences of the BAIT polypeptide can be varied without significant effect of the structure or function of the protein. If such differences in sequence are contemplated, it should be remembered that there will be critical areas on the protein which determine activity. In general, it is possible to replace residues which form the tertiary structure, provided that residues performing a similar function are used. In other instances, the type of residue may be completely unimportant if the alteration occurs at a non-critical region of the protein.

Thus, the invention further includes variations of the BAIT polypeptide which show substantial BAIT polypeptide activity or which include regions of BAIT protein such as the protein portions discussed below. Such mutants include deletions, insertions, inversions, repeats, and type substitutions selected according to general rules known in the art so as have little effect on activity. For example, guidance concerning how to make phenotypically silent amino acid substitutions is provided in Bowie, J. U. et al., "Deciphering the Message in Protein Sequences: Tolerance to Amino Acid Substitutions," *Science* 247:1306–1310 (1990), wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections or screens to identify sequences that maintain functionality.

As the authors state, these studies have revealed that proteins are surprisingly tolerant of amino acid substitutions. The authors further indicate which amino acid changes are likely to be permissive at a certain position of the protein. For example, most buried amino acid residues require nonpolar side chains, whereas few features of surface side chains are generally conserved. Other such phenotypically silent substitutions are described in Bowie, J. U. et al., supra, and the references cited therein. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

As described above, the BAIT polypeptide includes a reactive center loop (RCL) which interacts with its target proteinase. Short peptides (e.g., 8–30 residues) containing this loop sequence will bind to BAIT and convert it to a substrate for the target proteinase. Such peptides are therefore antagonists of BAIT and also form part of the present invention. Further, mutants of BAIT with enhanced function are also provided by the invention, including: RCL replacements to increase inhibitory activity with tPA, trypsin or thrombin; mutations that increase structural stability or clearance half-life ; and mutations which enhance or block association with cofactors. One of ordinary skill would appreciate that such mutants can be designed and tested using, for instance, the methods described for other serpins in the references cited in the section above on "Serpin Mechanism."

The polypeptides of the present invention are preferably provided in an isolated form, and preferably are substantially purified. A recombinantly produced version of the BAIT polypeptide can be substantially purified by the method described in Osterwalder et al., 1996, supra The polypeptides of the present invention include the polypeptide encoded by the deposited cDNA including the leader, the mature polypeptide encoded by the deposited cDNA minus the leader (i.e., the mature protein), the polypeptide of FIG. 1 (SEQ ID NO:2) including the leader, the polypeptide of FIG. 1 (SEQ ID NO:2) minus the leader, as well as polypeptides which have at least 90% similarity, more preferably at least 95% similarity, and still more preferably at least 96%, 97%, 98% or 99% similarity to those described above. Further polypeptides of the present invention include polypeptides at least 80% identical, more preferably at least 90% or 95% identical, still more preferably at least 96%, 97%, 98% or 99% identical to the polypeptide encoded by the deposited cDNA, to the polypeptide of FIG. 1 (SEQ ID NO:2), and also include portions of such polypeptides with at least 30 amino acids and more preferably at least 50 amino acids.

By "% similarity" for two polypeptides is intended a similarity score produced by comparing the amino acid sequences of the two polypeptides using the Bestfit program (Wisconsin Sequence Analysis Package, Version 8 for Unix, Genetics Computer Group, University Research Park, 575 Science Drive, Madison, Wis. 53711) and the default settings for determining similarity. Bestfit uses the local homology algorithm of Smith and Waterman (Advances in Applied Mathematics 2:482–489, 1981) to find the best segment of similarity between two sequences.

By a polypeptide having an amino acid sequence at least, for example, 95% "identical" to a reference amino acid sequence of a BAIT polypeptide is intended that the amino acid sequence of the polypeptide is identical to the reference sequence except that the polypeptide sequence may include up to five amino acid alterations per each 100 amino acids of the reference amino acid of the BAIT polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequence shown in FIG. 1 (SEQ ID NO:2) or to the amino acid sequence encoded by deposited cDNA clone can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

The polypeptide of the present invention could be used as a molecular weight marker on SDS-PAGE gels or on molecular sieve gel filtration columns using methods well known to those of skill in the art. As described in detail below, the polypeptides of the present invention can also be used to raise polyclonal and monoclonal antibodies, which are useful in assays for detecting BAIT protein expression as described below or as antagonists capable of enhancing or inhibiting BAIT protein function. Further, such polypeptides can be used in the yeast two-hybrid system to "capture" BAIT protein binding proteins which are candidate target proteins for BAIT inhibition, according to the present invention. The yeast two hybrid system is described in Fields and Song, *Nature* 340:245–246 (1989).

Epitope-bearing portions of BAIT Polypeptides

In another aspect, the invention provides a peptide or polypeptide comprising an epitope-bearing portion of a polypeptide of the invention. The epitope of this polypeptide portion is an immunogenic or antigenic epitope of a polypeptide of the invention. An "immunogenic epitope" is defined as a part of a protein that elicits an antibody response when the whole protein is the immunogen. These immunogenic epitopes are believed to be confined to a few loci on the molecule. On the other hand, a region of a protein molecule to which an antibody can bind is defined as an "antigenic epitope." The number of immunogenic epitopes of a protein generally is less than the number of antigenic epitopes. See, for instance, Geysen et al., Proc. Natl. Acad. Sci. U.S.A. 81:3998–4002 (1983).

Non-limiting examples of antigenic polypeptides or peptides that can be used to generate BAIT-specific antibodies include amino acid sequences shown in FIG. 1, as follows: a polypeptide comprising amino acid residues from about Val 31 to about Leu 47 (SEQ ID NO:2); a polypeptide comprising amino acid residues from about Leu 62 to about Ser 88 (SEQ ID NO:2); a polypeptide comprising amino acid residues from about Val 155 to about Ala 175 (SEQ ID NO:2); a polypeptide comprising amino acid residues from about Phe 186 to about Pro 215 (SEQ ID NO:2); a polypeptide comprising amino acid residues from about Tyr 225 to about Ile 239 (SEQ ID NO:2); a polypeptide comprising amino acid residues from about Leu 243 to about Leu 255 (SEQ ID NO:2); a polypeptide comprising amino acid residues from about Arg 380 to about Gly 386 (SEQ ID NO:2); and a polypeptide comprising amino acid residues from about Met 395 to about Leu 410. (SEQ ID NO:2). As indicated above, the inventor has determined that the above polypeptide fragments are antigenic regions of the BAIT protein based on an analysis of the BAIT amino acid sequence using the Jameson-Wolf "Antigenic Index" (FIG. 3). Methods for determining other such epitope-bearing portions of the BAIT protein are described in detail below.

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A. (1983) "Antibodies that react with predetermined sites on proteins", *Science*, 219:660–666. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Peptides that are extremely hydrophobic and those of six or fewer residues generally are ineffective at inducing antibodies that bind to the mimicked protein; longer, peptides, especially those containing proline residues, usually are effective. Sutcliffe et al., supra, at 661. For instance, 18 of 20 peptides designed according to these guidelines, containing 8–39 residues covering 75% of the sequence of the influenza virus hemagglutinin HA1 polypeptide chain, induced antibodies that reacted with the HA1 protein or intact virus; and 12/12 peptides from the MuLV polymerase and 18/18 from the rabies glycoprotein induced antibodies that precipitated the respective proteins.

Antigenic epitope-bearing peptides and polypeptides of the invention are therefore useful to raise antibodies, including monoclonal antibodies, that bind specifically to a polypeptide of the invention. Thus, a high proportion of hybridomas obtained by fusion of spleen cells from donors immunized with an antigen epitope-bearing peptide generally secrete antibody reactive with the native protein. Sutcliffe et al., supra, at 663. The antibodies raised by antigenic epitope-bearing peptides or polypeptides are useful to detect the mimicked protein, and antibodies to different peptides may be used for tracking the fate of various regions of a protein precursor which undergoes post-translational processing. The peptides and anti-peptide antibodies may be used in a variety of qualitative or quantitative assays for the mimicked protein, for instance in competition assays since it has been shown that even short peptides (e.g., about 9 amino acids) can bind and displace the larger peptides in immunoprecipitation assays. See, for instance, Wilson et al., *Cell* 37:767–778 (1984) at 777. The anti- peptide antibodies of the invention also are useful for purification of the mimicked protein, for instance, by adsorption chromatography using methods well known in the art.

Antigenic epitope-bearing peptides and polypeptides of the invention designed according to the above guidelines preferably contain a sequence of at least seven, more preferably at least nine and most preferably between about 15 to about 30 amino acids contained within the amino acid sequence of a polypeptide of the invention. However, peptides or polypeptides comprising a larger portion of an amino acid sequence of a polypeptide of the invention, containing about 30 to about 50 amino acids, or any length up to and including the entire amino acid sequence of a polypeptide of the invention, also are considered epitope-bearing peptides or polypeptides of the invention and also are useful for inducing antibodies that react with the mimicked protein. Preferably, the amino acid sequence of the epitope-bearing peptide is selected to provide substantial solubility in aqueous solvents (i.e., the sequence includes relatively hydrophilic residues and highly hydrophobic sequences are preferably avoided); and sequences containing proline residues are particularly preferred.

The epitope-bearing peptides and polypeptides of the invention may be produced by any conventional means for making peptides or polypeptides including recombinant means using nucleic acid molecules of the invention. For instance, a short epitope-bearing amino acid sequence may be fused to a larger polypeptide which acts as a carrier during recombinant production and purification, as well as during immunization to produce anti-peptide antibodies. Epitope-bearing peptides also may be synthesized using known methods of chemical synthesis. For instance, Houghten has described a simple method for synthesis of large numbers of peptides, such as 10–20 mg of 248 different 13 residue peptides representing single amino acid variants of a segment of the HA1 polypeptide which were prepared and characterized (by ELISA-type binding studies) in less than four weeks. Houghten, R. A. (1985) "General method for the rapid solid-phase synthesis of large numbers of peptides: specificity of antigen-antibody interaction at the level of individual amino acids." *Proc. Natl. Acad. Sci. USA* 82:5131–5135. This "Simultaneous Multiple Peptide Synthesis (SMPS)" process is further described in U.S. Pat. No. 4,631,211 to Houghten et al. (1986). In this procedure the individual resins for the solid-phase synthesis of various peptides are contained in separate solvent-permeable packets, enabling the optimal use of the many identical repetitive steps involved in solid-phase methods. A completely manual procedure allows 500–1000 or more syntheses to be conducted simultaneously. Houghten et al., supra, at 5134.

Epitope-bearing peptides and polypeptides of the invention are used to induce antibodies according to methods well known in the art. See, for instance, Sutcliffe et al., supra; Wilson et al., supra; Chow, M. et al., *Proc. Natl. Acad. Sci. USA* 82:910–914; and Bittle, F. J. et al., *J. Gen. Virol.* 66:2347–2354 (1985). Generally, animals may be immunized with free peptide; however, anti-peptide antibody titer may be boosted by coupling of the peptide to a macromolecular carrier, such as keyhole limpet hemacyanin (KLH) or tetanus toxoid. For instance, peptides containing cysteine may be coupled to a carrier using a linker such as m-maleimidobenzoyl-N-hydroxysuccinimide ester (MBS), while other peptides may be coupled to a carrier using a more general linking agent such as glutaraldehyde. Animals such as rabbits, rats and mice are immunized with either free or carrier-coupled peptides, for instance, by intraperitoneal and/or intradermal injection of emulsions containing about 100 g peptide or carrier protein and Freund's adjuvant. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

Immunogenic epitope-bearing peptides of the invention, i.e., those parts of a protein that elicit an antibody response when the whole protein is the immunogen, are identified according to methods known in the art. For instance, Geysen et al., supra, discloses a procedure for rapid concurrent synthesis on solid supports of hundreds of peptides of sufficient purity to react in an enzyme-linked immunosorbent assay. Interaction of synthesized peptides with antibodies is then easily detected without removing them from the support. In this manner a peptide bearing an immunogenic epitope of a desired protein may be identified routinely by one of ordinary skill in the art. For instance, the immunologically important epitope in the coat protein of foot-and-mouth disease virus was located by Geysen et al. with a resolution of seven amino acids by synthesis of an overlapping set of all 208 possible hexapeptides covering the entire 213 amino acid sequence of the protein. Then, a complete replacement set of peptides in which all 20 amino acids were substituted in turn at every position within the epitope were synthesized, and the particular amino acids conferring specificity for the reaction with antibody were determined. Thus, peptide analogs of the epitope-bearing peptides of the invention can be made routinely by this method. U.S. Pat. No. 4,708,781 to Geysen (1987) further describes this method of identifying a peptide bearing an immunogenic epitope of a desired protein.

Further still, U.S. Pat. No. 5,194,392 to Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092 to Geysen (1989) describes a method of detecting or determining a sequence of monomers which is a topographical equivalent of a ligand which is complementary to the ligand binding site of a particular receptor of interest. Similarly, U.S. Pat. No. 5,480,971 to Houghten, R. A. et al. (1996) on Peralkylated Oligopeptide Mixtures discloses linear C1–C7-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

As one of skill in the art will appreciate, BAIT polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EP A 394,827; Traunecker et al., Nature 331:84–86 (1988)). Fusion proteins that have a disulfide-linked dimeric structure due to the IgG part can also be more efficient in binding and neutralizing other molecules than the monomeric BAIT protein or protein fragment alone (Fountoulakis et al., J. Biochem. 270:3958–3964 (1995)).

Diagnosis of Nervous System-Related Disorders

The present inventors have discovered that BAIT is expressed in whole human brain, and to a much lesser extent in adult pancreas and adult heart. More particularly, by Northern blotting a 2 kb mRNA was expressed mostly in adult brain (at a relative level of ~5x) and to a much lesser extent in adult pancreas (~1x) and adult heart (~0.5x). Adult tissues not expressing significant amounts of mRNA include placenta, lung, liver, skeletal muscle, kidney, spleen, thymus, prostate, testis, ovary, small intestine, colon, and peripheral blood leukocytes. In addition, in the nervous system a 2 kb mRNA was seen in cerebral cortex, medulla, occipital lobe, frontal lobe, temporal lobe, putamen, and spinal cord but not in cerebellum. In the chicken, neuroserpin, the presumptive ortholog of the human BAIT protein, was found to be secreted from axons of both CNS and PNS neurons. Osterwalder et al., supra. The most prominant expression of neuroserpin in adult chickens is found in the hyperstriatum accessorium, the neostriaum and the hippocampus, plastic regions of the adult brain involved in processes of learning and memory where a subtle balance between and anti-proteolytic activities seems to be required for appropriate synaptic function. Id. at 2951. Further, transgenic mice with an enhanced proteolytic activity in the cortex and hippocampus due to overexpression of urokinase-type plasminogen activator (u-PA) have been found to exhibit impaired spatial, olfactory and taste-aversion learning. Id. Further still, elimination of a serpin inhibitor of u-PA, PNI (described above) by homologous recombination leads to reduced long-term potentiation (LTP) of learning, whereas overexpression of PNI results in enhanced LTP of hippocampal neurons. Id. The available observations on temporal-spatial patterns of expression of neuroserpin the chicken and BAIT polypeptide in human tissues implicate BAIT as a regulator for synaptogenesis and the subsequent remodelling processes including synapse elimination rather than neurite outgrowth. Id.

Accordingly, for a number of disorders of the central or peripheral nervous system, significantly higher or lower levels of BAIT gene expression may be detected in certain tissues (e.g., adult brain, embryonic retina, cerebellum and spinal chord) or bodily fluids (e.g., serum, plasma, urine, synovial fluid or spinal fluid) taken from an individual having such a disorder, relative to a "standard" BAIT gene expression level, i.e., the BAIT expression level in healthy tissue from an individual not having the nervous system disorder. Thus, the invention provides a diagnostic method useful during diagnosis of nervous system disorders, which involves: (a) assaying BAIT gene expression level in cells or body fluid of an individual; (b) comparing the BAIT gene expression level with a standard BAIT gene expression level, whereby an increase or decrease in the assayed BAIT gene expression level compared to the standard expression level is indicative of disorder in the nervous system.

By individual is intended mammalian individuals, preferably humans, including adults, children, babies and embryos or fetuses at all stages of development of the nervous system. By "measuring the expression level of the gene encoding the BAIT protein" is intended qualitatively or quantitatively measuring or estimating the level of the BAIT protein or the level of the mRNA encoding the BAIT protein in a first biological sample either directly (e.g., by determining or estimating absolute protein level or mRNA level) or relatively (e.g., by comparing to the BAIT protein level or mRNA level in a second biological sample). Preferably, the BAIT protein level or mRNA level in the first biological sample is measured or estimated and compared to a standard BAIT protein level or mRNA level, the standard being taken from a second biological sample obtained from an individual not having the disorder or being determined by averaging levels from a population of individuals not having a disorder of the immune system. As will be appreciated in the art, once a standard BAIT protein level or mRNA level is known, it can be used repeatedly as a standard for comparison.

By "biological sample" is intended any biological sample obtained from an individual, body fluid, cell line, tissue culture, or other source which contains BAIT protein or mRNA. As indicated, biological samples include body fluids (such as sera, plasma, urine, synovial fluid and spinal fluid) which contain secreted mature BAIT protein, nervous system tissue, and other tissue sources found to express BAIT or a BAIT receptor. Methods for obtaining tissue biopsies and body fluids from mammals are well known in the art. Where the biological sample is to include mRNA, a tissue biopsy is the preferred source.

The present invention is useful for diagnosis of various nervous system-related disorders in mammals, preferably humans. Such disorders include impaired processes of learning and memory, including impaired spatial, olfactory and taste-aversion learning, learning and memory impairments associated with Alzherimer's disease, and the like.

Total cellular RNA can be isolated from a biological sample using any suitable technique such as the single-step guanidinium-thiocyanate-phenol-chloroform method described in Chomczynski and Sacchi, *Anal. Biochem.* 162:156–159 (1987). Levels of mRNA encoding the BAIT protein are then assayed using any appropriate method. These include Northern blot analysis, S1 nuclease mapping, the polymerase chain reaction (PCR), reverse transcription in combination with the polymerase chain reaction (RT-PCR), and reverse transcription in combination with the ligase chain reaction (RT-LCR).

Northern blot analysis can be performed as described in Harada et al., Cell 63:303–312 (1990). Briefly, total RNA is prepared from a biological sample as described above. For the Northern blot, the RNA is denatured in an appropriate buffer (such as glyoxal/dimethyl sulfoxide/sodium phosphate buffer), subjected to agarose gel electrophoresis, and transferred onto a nitrocellulose filter. After the RNAs have been linked to the filter by a UV linker, the filter is prehybridized in a solution containing formamide, SSC, Denhardt's solution, denatured salmon sperm, SDS, and sodium phosphate buffer. BAIT protein cDNA labeled according to any appropriate method (such as the $^{32}$P-multiprimed DNA labeling system (Amersham)) is used as probe. After hybridization overnight, the filter is washed and exposed to x-ray film. cDNA for use as probe according to the present invention is described in the sections above and will preferably be at least 15 bp in length.

S1 mapping can be performed as described in Fujita et al., *Cell* 49:357–367 (1987). To prepare probe DNA for use in S1 mapping, the sense strand of above-described cDNA is used as a template to synthesize labeled antisense DNA. The antisense DNA can then be digested using an appropriate restriction endonuclease to generate further DNA probes of a desired length. Such anti sense probes are useful for visualizing protected bands corresponding to the target mRNA (i.e., mRNA encoding the BAIT protein). Northern blot analysis can be performed as described above.

Preferably, levels of mRNA encoding the BAIT protein are assayed using the RT-PCR method described in Makino et al., *Technique* 2:295–301 (1990). By this method, the radioactivities of the "amplicons" in the polyacrylamide gel bands are linearly related to the initial concentration of the target mRNA. Briefly, this method involves adding total RNA isolated from a biological sample in a reaction mixture containing a RT primer and appropriate buffer. After incubating for primer annealing, the mixture can be supplemented with a RT buffer, dNTPs, DTT, RNase inhibitor and reverse transcriptase. After incubation to achieve reverse transcription of the RNA, the RT products are then subject to PCR using labeled primers. Alternatively, rather than labeling the primers, a labeled dNTP can be included in the PCR reaction mixture. PCR amplification can be performed in a DNA thermal cycler according to conventional techniques. After a suitable number of rounds to achieve amplification, the PCR reaction mixture is electrophoresed on a polyacrylamide gel. After drying the gel, the radioactivity of the appropriate bands (corresponding to the mRNA encoding the BAIT protein)) is quantified using an imaging analyzer. RT and PCR reaction ingredients and conditions, reagent and gel concentrations, and labeling methods are well known in the art. Variations on the RT-PCR method will be apparent to the skilled artisan. Any set of oligonucleotide primers which will amplify reverse transcribed target mRNA can be used and can be designed as described in the sections above.

Assaying BAIT protein levels in a biological sample can occur using any art-known method. Preferred for assaying BAIT protein levels in a biological sample are antibody-based techniques. For example, BAIT protein expression in tissues can be studied with classical immunohistological methods. In these, the specific recognition is provided by the primary antibody (polyclonal or monoclonal) but the secondary detection system can utilize fluorescent, enzyme, or other conjugated secondary antibodies. As a result, an immunohistological staining of tissue section for pathological examination is obtained. Tissues can also be extracted, e.g., with urea and neutral detergent, for the liberation of BAIT protein for Western-blot or dot/slot assay (Jalkanen, M., et al., *J. Cell. Biol.* 101:976–985 (1985); Jalkanen, M., et al., *J. Cell . Biol.* 105:3087–3096 (1987)). In this technique, which is based on the use of cationic solid phases, quantitation of BAIT protein can be accomplished using isolated BAIT protein as a standard. This technique can also be applied to body fluids. With these samples, a molar concentration of BAIT protein will aid to set standard values of BAIT protein content for different body fluids, like serum, plasma, urine, spinal fluid, etc. The normal appearance of BAIT protein amounts can then be set using values from healthy individuals, which can be compared to those obtained from a test subject.

Other antibody-based methods useful for detecting BAIT protein gene expression include immunoassays, such as the enzyme linked immunosorbent assay (ELISA) and the radioimmunoassay (RIA). For example, a BAIT protein-specific monoclonal antibody can be used both as an immunoadsorbent and as an enzyme-labeled probe to detect and quantify the BAIT protein. The amount of BAIT protein present in the sample can be calculated by reference to the amount present in a standard preparation using a linear regression computer algorithm. Such an ELISA for detecting a tumor antigen is described in Iacobelli et al., *Breast Cancer Research and Treatment* 11:19–30 (1988). In another ELISA assay, two distinct specific monoclonal antibodies can be used to detect BAIT protein in a body fluid. In this assay, one of the antibodies is used as the immunoadsorbent and the other as the enzyme-labeled probe.

The above techniques may be conducted essentially as a "one-step" or "two-step" assay. The "one-step" assay involves contacting BAIT protein with immobilized antibody and, without washing, contacting the mixture with the labeled antibody. The "two-step" assay involves washing before contacting the mixture with the labeled antibody. Other conventional methods may also be employed as suitable. It is usually desirable to immobilize one component of the assay system on a support, thereby allowing other components of the system to be brought into contact with the component and readily removed from the sample.

Suitable enzyme labels include, for example, those from the oxidase group, which catalyze the production of hydrogen peroxide by reacting with substrate. Glucose oxidase is particularly preferred as it has good stability and its substrate (glucose) is readily available. Activity of an oxidase label may be assayed by measuring the concentration of hydrogen peroxide formed by the enzyme-labeled antibody/substrate reaction. Besides enzymes, other suitable labels include radioisotopes, such as iodine ($^{125}I$, $^{121}I$), carbon ($^{14}C$), sulfur ($^{35}S$), tritium ($^{3}H$), indium ($^{112}In$), and technetium ($^{99m}Tc$), and fluorescent labels, such as fluorescein and rhodamine, and biotin.

In addition to assaying BAIT protein levels in a biological sample obtained from an individual, BAIT protein can also be detected in vivo by imaging. Antibody labels or markers for in vivo imaging of BAIT protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A BAIT protein-specific antibody or antibody fragment which has been labeled with an appropriate detectable imaging moiety, such as a radioisotope (for example, $^{131}I$, $^{112}In$, $^{99m}Tc$), a radio-opaque substance, or a material detectable by nuclear magnetic resonance, is introduced (for example, parenterally, subcutaneously or intraperitoneally) into the mammal to be examined for immune system disorder. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}Tc$. The labeled antibody or antibody fragment will then preferentially accumulate at the location of cells which contain BAIT protein. In vivo tumor imaging is described in S. W. Burchiel et al., "Immunopharmaco-kinetics of Radiolabeled Antibodies and Their Fragments" (Chapter 13 in *Tumor Imaging: The Radiochemical Detection of Cancer*, S. W. Burchiel and B. A. Rhodes, eds., Masson Publishing Inc. (1982)).

BAIT-protein specific antibodies for use in the present invention can be raised against the intact BAIT protein or an antigenic polypeptide fragment thereof, which may be presented together with a carrier protein, such as an albumin, to an animal system (such as rabbit or mouse) or, if it is long enough (at least about 25 amino acids), without a carrier.

As used herein, the term "antibody" (Ab) or "monoclonal antibody" (Mab) is meant to include intact molecules as well as antibody fragments (such as, for example, Fab and F(ab')$_2$ fragments) which are capable of specifically binding to BAIT protein. Fab and F(ab')$_2$ fragments lack the Fc fragment of intact antibody, clear more rapidly from the circulation, and may have less non-specific tissue binding of an intact antibody (Wahl et al., *J. Nucl. Med.* 24:316–325 (1983)). Thus, these fragments are preferred.

The antibodies of the present invention may be prepared by any of a variety of methods. For example, cells expressing the BAIT protein or an antigenic fragment thereof can be administered to an animal in order to induce the production of sera containing polyclonal antibodies. In a preferred method, a preparation of BAIT protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or BAIT protein binding fragments thereof). Such monoclonal antibodies can be prepared using hybridoma technology (Kohler et al., *Nature* 256:495 (1975); Kohler et al., *Eur. J. Immunol.* 6:511 (1976); Kohler et al., *Eur. J. Immunol.* 6:292 (1976); Hammerling et al., in: *Monoclonal Antibodies and T-Cell Hybridomas*, Elsevier, N.Y., (1981)pp. 563–681). In general, such procedures involve immunizing an animal (preferably a mouse) with a BAIT protein antigen or, more preferably, with a BAIT protein-expressing cell. Suitable cells can be recognized by their capacity to bind anti-BAIT protein antibody. Such cells may be cultured in any suitable tissue culture medium; however, it is preferable to culture cells in Earle's modified Eagle's medium supplemented with 10% fetal bovine serum (inactivated at about 56° C.), and supplemented with about 10 g/l of nonessential amino acids, about 1,000 U/ml of penicillin, and about 100 g/ml of streptomycin. The splenocytes of such mice are extracted and fused with a suitable myeloma cell line. Any suitable myeloma cell line may be employed in accordance with the present invention; however, it is preferable to employ the parent myeloma cell line (SP$_2$O), available from the American Type Culture Collection, Rockville, Md. After fusion, the resulting hybridoma cells are selectively maintained in HAT medium, and then cloned by limiting dilution as described by Wands et al. (*Gastroenterology* 80:225–232 (1981)). The hybridoma cells obtained through such a selection are then assayed to identify clones which secrete antibodies capable of binding the BAIT protein antigen.

Alternatively, additional antibodies capable of binding to the BAIT protein antigen may be produced in a two-step procedure through the use of anti-idiotypic antibodies. Such a method makes use of the fact that antibodies are themselves antigens, and that, therefore, it is possible to obtain an antibody which binds to a second antibody. In accordance with this method, BAIT-protein specific antibodies are used to immunize an animal, preferably a mouse. The splenocytes of such an animal are then used to produce hybridoma cells, and the hybridoma cells are screened to identify clones which produce an antibody whose ability to bind to the BAIT protein-specific antibody can be blocked by the BAIT protein antigen. Such antibodies comprise anti-idiotypic antibodies to the BAIT protein-specific antibody and can be used to immunize an animal to induce formation of further BAIT protein-specific antibodies.

It will be appreciated that Fab and F(ab')$_2$ and other fragments of the antibodies of the present invention may be used according to the methods disclosed herein. Such fragments are typically produced by proteolytic cleavage, using enzymes such as papain (to produce Fab fragments) or pepsin (to produce F(ab')$_2$ fragments). Alternatively, BAIT protein-binding fragments can be produced through the application of recombinant DNA technology or through synthetic chemistry.

Where in vivo imaging is used to detect enhanced levels of BAIT protein for diagnosis in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. See, for review, Morrison, *Science* 229:1202 (1985); Oi et al., *BioTechniques* 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., *Nature* 312:643 (1984); Neuberger et al., *Nature* 314:268 (1985).

Further suitable labels for the BAIT protein-specific antibodies of the present invention are provided below. Examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, and acetylcholine esterase.

Examples of suitable radioisotopic labels include $^{3}$H, $^{111}$In, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc, $^{109}$Pd, etc. $^{111}$In is a preferred isotope where in vivo imaging is used since it avoids the problem of dehalogenation of the $^{125}$I or $^{131}$I-labeled monoclonal antibody by the liver. In addition, this radionucleotide has a more favorable gamma emission energy for imaging (Perkins et al., *Eur. J. Nucl. Med.* 10:296–301 (1985); Carasquillo et al., *J. Nucl. Med.* 28:281–287 (1987)). For example, $^{111}$In coupled to monoclonal antibodies with 1-(P-isothiocyanatobenzyl)-DPTA has shown little uptake in non-tumorous tissues, particularly the liver, and therefore enhances specificity of tumor localization (Esteban et al., *J. Nucl. Med.* 28:861–870 (1987)). Examples of suitable non-radioactive isotopic labels include $^{157}$Gd, $^{55}$Mn, $^{162}$Dy, $^{52}$Tr, and $^{56}$Fe.

Examples of suitable fluorescent labels include an $^{152}$Eu label, a fluorescein label, an isothiocyanate label, a rhodamine label, a phycoerythrin label, a phycocyanin label, an allophycocyanin label, an o-phthaldehyde label, and a fluorescamine label. Examples of suitable toxin labels include diphtheria toxin, ricin, and cholera toxin. Examples of chemiluminescent labels include a luminal label, am isoluminal label, an aromatic acridinium ester label, an imidazole label, an acridinium salt label, an oxalate ester label, a luciferin label, a luciferase label, and an aequorin label. Examples of nuclear magnetic resonance contrasting agents include heavy metal nuclei such as Gd, Mn, and iron.

Typical techniques for binding the above-described labels to antibodies are provided by Kennedy et al., *Clin. Chim. Acta* 70:1–31 (1976), and Schurs et al., *Clin. Chim. Acta* 81:1–40 (1977). Coupling techniques mentioned in the latter are the glutaraldehyde method, the periodate method, the dimaleimide method, the m-maleimidobenzyl-N-hydroxy-succinimide ester method, all of which methods are incorporated by reference herein.

Treatment of Nervous System-Related and Other Disorders

As noted above, BAIT polynucleotides, polypeptides and other aspects of this invention are useful for diagnosis of various nervous system-related disorders in mammals, including impaired processes of learning and memory, including impaired spatial, olfactory and taste-aversion learning, learning and memory impairments associated with Alzherimer's disease, and the like. Given the activities modulated by BAIT, it is readily apparent that a substantially altered (increased or decreased) level of expression of BAIT in an individual compared to the standard or "normal" level produces pathological conditions such as those described above in relation to diagnosis of nervous system-related disorders. It will also be appreciated by one of ordinary skill that, since the BAIT protein of the invention is translated with a leader peptide suitable for secretion of the mature protein from the cells which express BAIT, when BAIT protein (particularly the mature form) is added from an exogenous source to cells, tissues or the body of an individual, the protein will exert its modulating activities on any of its target cells of that individual. Therefore, it will be appreciated that conditions caused by a decrease in the standard or normal level of BAIT activity in an individual, or an increase in a protease susceptible to inhibition by BAIT, particularly disorders of the nervous system, can be treated by administration of BAIT protein.

Figure 5:
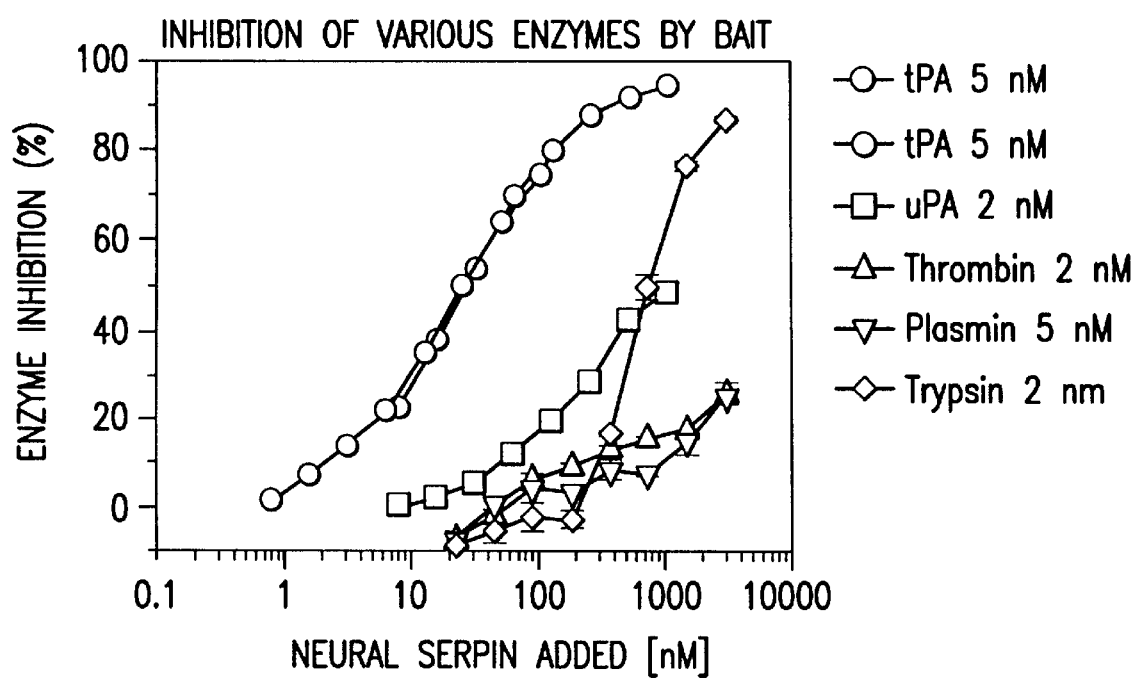
FIG. 5 shows the results of tests for inhibitory activity of purified human BAIT polypeptide on several proteolytic enzymes including thrombin (2 nM; -Δ-); tissue-type plasminogen activator (tPA, 5 nM; -○-), urokinase-type plasminogen activator (uPA, 2 nM; -□-), plasmin (5 nM; -▽-), and trypsin (2 nM; -◇-).

The human BAIT protein of the present invention has been shown to exhibit selective inhibition of tissue-type plasminogen activator (t-PA) with a lesser degree of inhibition of trypsin, thrombin or urokinase-type plasminogen activator (u-PA). More in particular, in vitro enzymatic activity has been demonstrated for the baculovirus-expressed purified protein. FIG. 5 shows the inhibition of t-PA, u-PA, plasmin, trypsin, and thrombin proteolytic activity with increasing amounts of purified protein expressed and purified as described below. t-PA was inhibited with a half-maximal inhibitory concentration ($IC_{50}$) of 200 nM. u-PA and trypsin were inhibited at an $IC_{50}$ of 1 $\mu$M and 0.7 $\mu$M, respectively. No other protease was inhibited to 50% of control. The rate constant for BAIT reaction with tPA is about $7.8 \pm 1.5 \times 10^{4}$ mol/sec.

More in particular, the inhibitory activity against various tPA (Genentech), uPA (Serono), plasmin (a gift of Dr. D. Strickland), thrombin (a gift of Dr. S. T. Olson), and β-trypsin (a gift of Dr. S. T. Olson), was determined in a single step chromogenic assay essentially as described (Lawrence, Strandberg, Ericson, & Ny, 1990, supra). Briefly, BAIT containing samples were serially diluted in microtiter plates into 0.15 M NaCl, 0.05 M Tris-HCl, pH 7.5 containing 100 $\mu$g/ml bovine serum albumin, and 0.01% Tween 80, 100 $\mu$l final volume. Enzyme was added (5 nM for tPA and plasmin, and 2 nM for thrombin, uPA, and trypsin), and the samples incubated for 30 minutes at 23° C. Next, 100 $\mu$l of the same buffer containing 0.5 mM substrate, (Spectrozyme tPA (BioPool) for tPA, S2444 (Chromogenix) for uPA, S2390 (Chromogenix) for plasmin, and chromozym TRY (Boehringer Mannheim) for trypsin and thrombin. The plates were then were incubated at 37° C. in a ThermoMax plate reader and the change in absorbance at 405 nM monitored for 30 minutes. The amount of inhibition was calculated from the residual enzyme activity. These results of these assays are shown in FIG. 5 where the % inhibition of each enzyme is plotted against the concentration of BAIT ("neural serpin").

Thus, the invention also provides a method of treatment of an individual in need of an increased level of BAIT activity (or of decreased proteolytic activity of a BAIT-susceptible protease, particularly t-PA) comprising administering to such an individual a pharmaceutical composition comprising an amount of an isolated BAIT polypeptide of the invention, particularly a mature form of the BAIT protein of the invention, effective to increase the BAIT activity level (and, thereby decrease the BAIT-susceptible protease activity) in such an individual.

As noted above, one member in the serpin family closely related to BAIT is protease nexin I (PNI) or glia-derived nexin (GDN) which has been shown to inhibit thrombin specifically and to promote, in vitro, neurite extension in neuroblastoma cell lines as well as primary hippocampal, and sympathetic neurons. The PNI gene is induced transcriptionally and protein levels are increased following rat sciatic nerve axotomy. Other neurotrophic factors like nerve growth factor, brain-derived neurotrophic factor, and insulin-like growth factor I respond likewise to peripheral nerve damage. Treatment of chick developing motoneurons, i.e. E6-E9 lumbrosacral motoneurons which normally undergo apoptosis, with PNI results in increased survival of motoneurons. Motoneuron death experimentally induced by sciatic nerve lesioning in mouse is also decreased by PNI addition. Alzheimer-diseased brain regions contain higher PNI/thrombin complexes compared with free PNI than do normal brains suggesting that PNI may have a role in CNS pathology.

Thus, due to the similarities in amino acid sequence and tissue localization between BAIT and PNI, BAIT can be used for treating peripheral neuropathies such as ALS or multiple sclerosis. Motoneuron or sensory neuron damage resulting from spinal cord injury also my be prevented by treatment with BAIT. In addition, central nervous system diseases like Alzheimer's disease may be treated with BAIT or, preferably, a small molecule analog capable of crossing the blood-brain barrier, which analog can be identified according to the methods of the present invention.

Aside from the nervous system-related disorders described above, under diagnostic uses of the invention based on detecting BAIT expression, the protease inhibitory activity of BAIT protein of the present invention also indicates that this protein may be used for therapeutic treatment of other conditions where excessive proteolytic activity of a BAIT susceptible protease may be involved, particularly t-PA. Thus, BAIT may be used to modulate the process of clot breakdown, for instance, in combination with Activase (recombinant t-PA) which Genentec is marketing for clot dissolution after stoke. A major problem with the present Activase therapy is that frequently excessive hemorrhaging occurs. BAIT provides a specific inhibitor of t-PA which would fine tune the treatment process and not interact with other serine proteases in the nervous system. Similarly, a product called Trasylol (aprotinin), a protease inhibitor, is being marketed by Bayer for bleeding disorders. The beneficial action of this serine protease inhibitor in limiting blood loss after cardiopulmonary bypass has been widely reported.

PNI has been shown to inhibit breakdown of extracellular matrix in a fibroblast tumor cell line. Such breakdown is thought to enable tumor cells to metastasize by weakening of extracellular matrix which normally prevents penetration of unrelated cells through a tissue. BAIT also may be used to inhibit extracellular matrix destruction associated with tumors secreting a BAIT-susceptible protease, for instance, neural tissue tumors secreting t-PA.

The BAIT polypeptide composition will be formulated and dosed in a fashion consistent with good medical practice, taking into account the clinical condition of the individual patient (especially the side effects of treatment with BAIT polypeptide alone), the site of delivery of the BAIT polypeptide composition, the method of administration, the scheduling of administration, and other factors known to practitioners. The "effective amount" of BAIT polypeptide for purposes herein is thus determined by such considerations.

As a general proposition, the total pharmaceutically effective amount of BAIT polypeptide administered parenterally per dose will be in the range of about 1 µg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the BAIT polypeptide is typically administered at a dose rate of about 1 µg/kg/hour to about 50 µg/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing the BAIT of the invention may be administered orally, rectally, parenterally, intracistemally, intravaginally, intraperitoneally, topically (as by powders, ointments, drops or transdermal patch), bucally, or as an oral or nasal spray. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

The BAIT polypeptide is also suitably administered by sustained-release systems. Suitable examples of sustained-release compositions include semi-permeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (Sidman, U. et al., *Biopolymers* 22:547–556 (1983)), poly (2- hydroxyethyl methacrylate) (R. Langer et al., *J. Biomed. Mater. Res.* 15:167–277 (1981), and R. Langer, *Chem. Tech.* 12:98–105 (1982)), ethylene vinyl acetate (R. Langer et al., Id.) or poly-D-(−)-3-hydroxybutyric acid (EP 133,988). Sustained-release BAIT polypeptide compositions also include liposomally entrapped BAIT polypeptide. Liposomes containing BAIT polypeptide are prepared by methods known per se: DE 3,218,121; Epstein et al., *Proc. Natl. Acad. Sci.* (*USA*) 82:3688–3692 (1985); Hwang et al., *Proc. Natl. Acad. Sci.* (*USA*) 77:4030–4034 (1980); EP 52,322; EP 36,676; EP 88,046; EP 143,949; EP 142,641; Japanese Pat. Appl. 83–118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal BAIT polypeptide therapy.

For parenteral administration, in one embodiment, the BAIT polypeptide is formulated generally by mixing it at the desired degree of purity, in a unit dosage injectable form (solution, suspension, or emulsion), with a pharmaceutically acceptable carrier, i.e., one that is non-toxic to recipients at the, dosages and concentrations employed and is compatible with other ingredients of the formulation. For example, the formulation preferably does not include oxidizing agents and other compounds that are known to be deleterious to polypeptides.

Generally, the formulations are prepared by contacting the BAIT polypeptide (and, optionally, any cofactor which may enhance its activity) uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The BAIT polypeptide is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of BAIT polypeptide salts.

BAIT polypeptide to be used for therapeutic administration must be sterile. Sterility is readily accomplished by filtration through sterile filtration membranes (e.g., 0.2 micron membranes). Therapeutic BAIT polypeptide compositions generally are placed into a container having a sterile access port, for example, an intravenous solution bag or vial having a stopper pierceable by a hypodermic injection needle.

BAIT polypeptide ordinarily will be stored in unit or multi-dose containers, for example, sealed ampoules or vials, as an aqueous solution or is a lyophilized formulation for reconstitution. As an example of a lyophilized formulation, 10-ml vials are filled with 5 ml of sterile-filtered 1% (w/v) aqueous BAIT polypeptide solution, and the resulting mixture is lyophilized. The infusion solution is prepared by reconstituting the lyophilized BAIT polypeptide using bacteriostatic Water-for-Injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

Agonists and Antagonists—Assays and Molecules

The invention also provides a method of screening compounds to identify those which enhance or block the action of BAIT on proteases, such as its interaction with proteases or with protein cofactors such as extracellular matrix proteins. Thus, protease-inhibiting activity of another serpin, plasminogen activator inhibitor-I (PAI-1), is known to be modulated by its protein cofactor, vitronectin, which binds to active PAI-1 and prevents its spontaneous conversion to a latent form. See, for instance, Reilly, T. M., et al., supra. Similarly, heparin is known to enhance the activity of antithrombin III and several other serpins. The present invention provides an assay for identifying such a protein or other cofactor which binds to BAIT and thereby modulates its anti-proteolytic activity. In general, therefore, an agonist in the present context is a compound which increases the natural biological functions of BAIT or which functions in a manner similar to BAIT, while antagonists decrease or eliminate such functions.

For example, a cellular compartment, such as a membrane or a preparation thereof, such as a membrane-preparation, may be prepared from a cell that expresses a molecule that binds BAIT, such as a molecule of a signaling or regulatory pathway modulated by BAIT. The preparation is incubated with labeled BAIT in the absence or the presence of a candidate molecule which may be a BAIT agonist or antagonist. The ability of the candidate molecule to bind the binding molecule is reflected in decreased binding of the labeled ligand. Molecules which bind gratuitously, i.e., without inducing the effects of BAIT on binding the BAIT binding molecule, are most likely to be good antagonists. Molecules that bind well and elicit effects that are the same as or closely related to BAIT are agonists.

BAIT-like effects of potential agonists and antagonists may be measured, for instance, by determining activity of a second messenger system following interaction of the candidate molecule with a cell or appropriate cell preparation, and comparing the effect with that of BAIT or molecules that elicit the same effects as BAIT. Second messenger systems that may be useful in this regard include but are not limited to AMP guanylate cyclase, ion channel or phosphoinositide hydrolysis second messenger systems.

Another example of an assay for BAIT antagonists is a competitive assay that combines BAIT and a potential antagonist BAIT-susceptible protease, particularly t-PA, under appropriate conditions for a competitive inhibition assay. BAIT can be labeled, such as by radioactivity, such that the number of BAIT molecules bound to protease molecules can be determined accurately to assess the effectiveness of the potential antagonist.

Potential antagonists include small organic molecules, peptides, polypeptides and antibodies that bind to a polypeptide of the invention and thereby inhibit or extinguish its activity. Potential antagonists also may be small organic molecules, a peptide, a polypeptide such as a closely related protein or antibody that binds the same sites on a binding molecule, such as BAIT susceptible protease molecule, without inducing BAIT-induced activities, thereby preventing the action of BAIT by excluding BAIT from binding.

Other potential antagonists include antisense molecules. Antisense technology can be used to control gene expression through antisense DNA, or RNA or through triple-helix formation. Antisense techniques are discussed, for example, in Okano, *J. Neurochem.* 56: 560 (1991); "Oligodeoxynucleotides as Antisense Inhibitors of Gene Expression, CRC Press, Boca Raton, Fla. (1988). Triple helix formation is discussed in, for instance Lee et al., *Nucleic Acids Research* 6: 3073 (1979); Cooney et al., *Science* 241: 456 (1988); and Dervan et al., *Science* 251: 136( (1991). The methods are based on binding of a polynucleotide to a complementary DNA or RNA. For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of BAIT. The antisense RNA oligonucleotide hybridizes to the mRNA in vivo and blocks translation of the mRNA molecule into BAIT polypeptide. The oligonucleotides described above can also be delivered to cells such that the antisense RNA or DNA may be expressed in vivo to inhibit production of BAIT.

The agonists and antagonists may be employed in a composition with a pharmaceutically acceptable carrier, e.g., as described above.

The BAIT agonists may be employed in place of a BAIT polypeptide, for instance, for treating peripheral neuropathies such as ALS or multiple sclerosis. Motoneuron or sensory neuron damage resulting from spinal cord injury also may be prevented by treatment with BAIT agonists. In addition, central nervous system diseases like Alzheimer's disease may be treated a small molecule agonist capable of crossing the blood-brain barrier, which analog can be identified according to the methods of the present invention. BAIT agonists also may be used for therapeutic treatment of other conditions where excessive proteolytic activity of a BAIT susceptible protease may be involved, particularly t-PA. Thus, BAIT may be used to modulate the process of clot breakdown, for instance, in combination with Activase (recombinant t-PA) for clot dissolution after stoke. Further, BAIT agonists also may be used to inhibit extracellular matrix destruction associated with tumors secreting a BAIT-susceptible protease, for instance, neural tissue tumors secreting t-PA.

The BAIT antagonists may be used in a method for treating an individual in need of a decreased level of BAIT activity in the body (i.e., less inhibition of a protease susceptible to BAIT) comprising administering to such an individual a composition comprising a therapeutically effective amount of a BAIT antagonist. As noted above, elimination of a serpin inhibitor of u-PA, PNI (described above) by homologous recombination leads to reduced long-term potentiation (LTP) of learning, whereas overexpression of PNI results in enhanced LTP of hippocampal neurons. Id. Similarly, antagonists of BAIT activity capable of passing the blood-brain barrier, by mimicking overexpression of BAIT, can be used to enhance LTP of hippocampal neurons in nervous system conditions characterized by excessive BAIT expression.

Chromosome Assays

Chromosome mapping studies have shown that the BAIT gene maps in the human genome to the location 4q31.2–31.3. Thus, the nucleic acid molecules of the present invention are also valuable for chromosome identification. The sequence is specifically targeted to and can hybridize with the above particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

In certain preferred embodiments in this regard, the cDNA herein disclosed is used to clone genomic DNA of a BAIT protein gene. This can be accomplished using a variety of well known techniques and libraries, which generally are available commercially. The genomic DNA then is used for in situ chromosome mapping using well known techniques for this purpose. Typically, in accordance with routine procedures for chromosome mapping, some trial and error may be necessary to identify a genomic probe that gives a good in situ hybridization signal.

In addition, in some cases, sequences can be mapped to chromosomes by preparing PCR primers (preferably 15–25 bp) from the cDNA. Computer analysis of the 3 untranslated region of the gene is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified portion.

PCR mapping of somatic cell hybrids is a rapid procedure for assigning a particular DNA to a particular chromosome. Using the present invention with the same oligonucleotide primers, sublocalization can be achieved with panels of portions from specific chromosomes or pools of large genomic clones in an analogous manner. Other mapping strategies that can similarly be used to map to its chromosome include in situ hybridization, prescreening with labeled flow- sorted chromosomes and preselection by hybridization to construct chromosome specific-cDNA libraries.

Fluorescence in situ hybridization ("FISH") of a cDNA clone to a metaphase chromosomal spread can be used to provide a precise chromosomal location in one step. This technique can be used with probes from the cDNA as short as 50 or 60 bp. For a review of this technique, see Verma et al., *Human Chromosomes: A Manual Of Basic Techniques*, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance In Man, available on-line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. This assumes 1 megabase mapping resolution and one gene per 20 kb.

Having generally described the invention, the same will be more readily understood by reference to the following examples, which are provided by way of illustration and are not intended as limiting.

EXAMPLES

Example 1

Expression and Purification of BAIT in *E. coli*

The bacterial expression vector pQE9 (pD 10) was used for bacterial expression in this example. (QIAGEN, Inc., 9259 Eton Avenue, Chatsworth, Calif., 91311). pQE9 encodes ampicillin antibiotic resistance ("Ampr") and contains a bacterial origin of replication ("ori"), an IPTG inducible promoter, a ribosome binding site ("RBS"), six codons encoding histidine residues that allow affinity purification using nickel-nitrilo-tri-acetic acid ("Ni-NTA") affinity resin sold by QIAGEN, Inc., supra, and suitable single restriction enzyme cleavage sites. These elements are arranged such that an inserted DNA fragment encoding a polypeptide expresses that polypeptide with the six His residues (i.e., a "6×His tag") covalently linked to the amino terminus of that polypeptide.

The DNA sequence encoding the desired portion BAIT protein lacking the hydrophobic leader sequence was amplified from the deposited cDNA clone using PCR oligonucleotide primers which anneal to the amino terminal sequences of the desired portion of the BAIT protein and to sequences in the deposited construct 3' to the cDNA coding sequence. Additional nucleotides containing restriction sites to facilitate cloning in the pQE9 vector are added to the 5' and 3' primer sequences, respectively.

For cloning the mature protein, the 5' primer has the sequence 5' GAGCAT GGATCCGCCACTTTCCCTGAGGAA 3' (SEQ ID NO:10) containing the underlined BamHI restriction site followed by 18 nucleotides of the amino terminal coding sequence of the mature BAIT sequence in FIG. 1. One of ordinary skill in the art would appreciate, of course, that the point in the protein coding sequence where the 5' primer begins may be varied to amplify a DNA segment encoding any desired portion of the complete BAIT protein shorter or longer than the mature form. The 3' primer has the sequence 5' GCACAT GGATCCTTAAAGTTCTTCGAAATCATG 3' (SEQ ID NO:11) containing the underlined BamHI restriction site followed by 21 nucleotides complementary to the 3' end of the coding sequence of the BAIT DNA sequence in FIG. 1.

The amplified BAIT DNA fragment and the vector pQ]E9 were digested with BamHI and the digested DNAs are then ligated together. Insertion of the BAIT DNA into the restricted pQE9 vector places the BAIT protein coding region downstream from the IPTG-inducible promoter and in-frame with an initiating AUG and the six histidine codons.

The ligation mixture was transformed into competent *E. coli* cells using standard procedures such as those described in Sambrook et al., *Molecular Cloning: a Laboratory Manual, 2nd Ed.*; Cold Spring Harbor Laboratory Press, Cold Spring Harbor, N.Y. (1989). *E. coli* strain M15/rep4, containing multiple copies of the plasmid pREP4, which expresses the lac repressor and confers kanamycin resistance ("Kanr"), is used in carrying out the illustrative example described herein. This strain, which is only one of many that are suitable for expressing BAIT protein, is available commercially from QIAGEN, Inc., supra. Transformants were identified by their ability to grow on LB plates in the presence of ampicillin and kanamycin. Plasmid DNA was isolated from resistant colonies and the identity of the cloned DNA confirmed by restriction analysis, PCR and DNA sequencing.

Clones containing the desired constructs were grown overnight ("O/N") in liquid culture in LB media supplemented with both ampicillin (100 μg/ml) and kanamycin (25 μg/ml). The O/N culture is used to inoculate a large culture, at a dilution of approximately 1:25 to 1:250. The cells were grown to an optical density at 600 nm ("OD600") of between 0.4 and 0.6 isopropyl-b-D-thiogalactopyranoside ("IPTG") was then added to a final concentration of 1 mM to induce transcription from the lac repressor sensitive promoter, by inactivating the lacI repressor. Cells subsequently were incubated further for 3 to 4 hours. Cells then were harvested by centrifugation.

The cells were then stirred for 3–4 hours at 4° C. in 6M guanidine-HCl, pH 8. The cell debris was removed by centrifugation, and the supernatant containing the BAIT was loaded onto a nickel-nitrilo-tri-acetic acid ("Ni-NTA") affinity resin column (available from QIAGEN, Inc., supra). Proteins with a 6×His tag bind to the Ni-NTA resin with high affinity and can be purified in a simple one-step procedure (for details see: The QIAexpressionist, 1995, QIAGEN, Inc., supra). Briefly the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the BAIT is eluted with 6 M guanidine-HCl, pH 5.

The purified protein was then renatured by dialyzing it against phosphate-buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M-1M urea gradient in 500 mM NaCl, 20% glycerol, 20 mM Tris/HCl pH 7.4, containing protease inhibitors. The renaturation should be performed over a period of 1.5 hours or more. After renaturation the proteins can be eluted by the addition of 250 mM immidazole. Immidazole is removed by a final dialyzing step against PBS or 50 mM sodium acetate pH 6 buffer plus 200 mM NaCl. The purified protein is stored at 4° C. or frozen at −80° C.

Example 2

Cloning, Expression and Purification of BAIT Protein in a Baculovirus Expression System In this illustrative example, the plasmid shuttle vector pA2 is used to insert the cloned DNA encoding the complete protein, including its naturally associated secretory signal (leader) sequence, into a baculovirus to express the mature BAIT protein, using standard methods as described in Summers et al., *A Manual of Methods for Baculovirus Vectors and Insect Cell Culture Procedures*, Texas Agricultural Experimental Station Bulletin No. 1555 (1987). This expression vector contains the strong polyhedrin promoter of the *Autographa californica* nuclear polyhedrosis virus (AcMNPV) followed by convenient restriction sites such as BamHI, Xba I and Asp718. The polyadenylation site of the simian virus 40 ("SV40") is used for efficient polyadenylation. For easy selection of recombinant virus, the plasmid contains the beta-galactosidase gene from *E. coli* under control of a weak Drosophila promoter in the same orientation, followed by the polyadenylation signal of the polyhedrin gene. The inserted genes are flanked on both sides by viral sequences for cell-mediated homologous recombination with wild-type viral DNA to generate viable virus that express the cloned polynucleotide.

Many other baculovirus vectors could be used in place of the vector above, such as pAc373, pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., *Virology* 170:31–39 (1989).

The cDNA sequence encoding the full length BAIT protein in the deposited clone, including the AUG initiation codon and the naturally associated leader sequence shown in FIG. 1 (SEQ ID NO:2), is amplified using PCR oligonucleotide primers corresponding to the 5' and 3' sequences of the gene. The 5' primer has the sequence 5' GAGCAT GGATCCGCCATCATGGCTTTCCTTGGACTC 3' (SEQ ID NO:12) containing the underlined BamHI restriction enzyme site, an efficient signal for initiation of translation in eukaryotic cells, as described by Kozak, M., *J. Mol. Biol.* 196:947–950 (1987), followed by 18 nucleotides of the sequence of the complete BAIT protein shown in FIG. 1, beginning with the AUG initiation codon. The 3' primer has the sequence 5'-GAGCATTCTAGAGTTGCAAACATA ATGTGC-3' (SEQ ID NO:13) containing the underlined XbaI restriction site followed by 18 nucleotides complementary to the 3' noncoding sequence in FIG. 1.

The amplified fragment was isolated from a 1% agarose gel using a commercially available kit ("Geneclean," BIO 101 Inc., La Jolla, Calif.). The fragment then is digested with BamHI and XbaI and again was purified on a 1% agarose gel. This fragment is designated herein F1.

The plasmid was digested with the restriction enzymes BamHI and XbaI using routine procedures known in the art. The DNA was then isolated from a 1% agarose gel using a commercially available kit ("Geneclean" BIO 101 Inc., La Jolla, Calif.). This vector DNA is designated herein "V1".

Fragment F1 and the plasmid V1 were ligated together with T4 DNA ligase. Competent *E. coli* cells were transformed with the ligation mixture and spread on culture plates. Bacteria were identified that contain the plasmid with the human BAIT gene by digesting DNA from individual colonies using BamHI and XbaI and then analyzing the digestion product by gel electrophoresis. The sequence of the cloned fragment was confirmed by DNA sequencing. This plasmid is designated herein pA2BAIT.

Five µg of the plasmid pA2BAIT was co-transfected with 1.0 µg of a commercially available linearized baculovirus DNA ("BaculoGold™ baculovirus DNA", Pharmingen, San Diego, Calif.), using the lipofection method described by Feigner et al., *Proc. Natl. Acad. Sci. USA* 84: 7413–7417 (1987). One µg of BaculoGold™ virus DNA and 5 µg of the plasmid pA2BAIT were mixed in a sterile well of a microtiter plate containing 50 µl of serum-free Grace's medium (Life Technologies Inc., Gaithersburg, Md.). Afterwards, 10 µg Lipofectin plus 90 µl Grace's medium were added, mixed and incubated for 15 minutes at room temperature. Then the transfection mixture was added drop-wise to Sf9 insect cells (ATCC CRL 1711) seeded in a 35 mm tissue culture plate with 1 ml Grace's medium without serum. The plate was then incubated for 5 hours at 27° C. After 5 hours the transfection solution was removed from the plate and 1 ml of Grace's insect medium supplemented with 10% fetal calf serum was added. The plate was put back into an incubator and cultivation was continued at 27° C. for four days.

After four days the supernatant was collected and a plaque assay was performed, as described by Summers and Smith, supra. An agarose gel with "Blue Gal" (Life Technologies Inc., Gaithersburg) was used to allow easy identification and isolation of gal-expressing clones, which produce blue-stained. plaques. (A detailed description of a "plaque assay" of this type can also be found in the user's guide for insect cell culture and baculovirology distributed by Life Technologies Inc., Gaithersburg, page 9–10). After appropriate incubation, blue stained plaques were picked with the tip of a micropipettor (e.g., Eppendorf). The agar containing the recombinant viruses were then resuspended in a microcentrifuge tube containing 200 µl of Grace's medium and the suspension containing the recombinant baculovirus was used to infect Sf9 cells seeded in 35 mm dishes. Four days later the supernatants of these culture dishes were harvested and then they were stored at 4° C. The recombinant virus is called V-BAIT.

To verify the expression of the BAIT gene Sf9 cells were grown in Grace's medium supplemented with 10% heat-inactivated FBS. The cells were infected with the recombinant baculovirus V-BAIT at a multiplicity of infection ("MOI") of about 2. Six hours later the medium was removed and replaced with SF900 II medium minus methionine and cysteine (available from Life Technologies Inc., Rockville, Md.). 42 hours later, 5 µCi of $^{35}$S-methionine and 5 µCi $^{35}$S-cysteine (available from Amersham) were added. The cells were further incubated for 16 hours and then harvested by centrifugation. The proteins in the supernatant as well as the intracellular proteins were analyzed by SDS-PAGE followed by autoradiography (if radiolabeled).

For production of unlabeled BAIT polypeptide, Sf9 cells were seeded in serum-free media at a density of $1.5 \times 10^6$ cells/ml in 200 ml spinner flasks. They were infected at an multiplicity of infection (moi) of 1 with the recombinant baculovirus encoding BAIT. At 96 hrs post-infection (pi), the cells were removed by centrifugation, and the conditioned media used as starting material.

Medium was diluted 1:1 (vol:vol) with 50 mM Na-Acetate pH 6.0 (Buffer A). The sample was applied to an HQ-50 column (Poros Resins, Perseptive Biosystems) at a flow rate of 30 mls/min. Bound protein was step-eluted with Buffer A containing 0.15, 0.35, 0.6 and 1.0 M NaCl and the fractions analyzed by SDS-PAGE. BAIT-containing fraction (350 mM step) were pooled, and diluted with Buffer A to a final NaCl concentration of 50 mM. This sample was applied to an HS-50 column (Poros Resins, Perseptive Biosystems) previously equilibrated with Buffer A plus 50 mM NaCl at a flow rate of 10 mls/min. Bound proteins were step eluted with Buffer A containing 1.0 M NaCl and fractions analyzed by SDS-PAGE. Finally, the pooled fractions were applied to an S-200 (Pharmacia) gel filtration column previously equilibrated with 50 mM Na-Acetate pH 6.5; 250 mM NaCl. BAIT-containing fractions eluted as a single peak which were pooled.

Protein concentration was determined using the Bio-Rad Protein Assay with BSA as a standard. Alternatively, the BCA Assay (Pierce) was used. The protein was ~90% pure as judged by SDS-PAGE. The baculovirus produced protein was shown to be glycosylated and the isolectric point (pI) of the protein was determined to be 5.0. This protein was used for in vitro activity assays described hereinabove. Microsequencing of the amino acid sequence of the amino terminus of the purified protein immediately after purification was used to determine the amino terminal sequence of the mature protein and thus the cleavage point and length (18 amino acids) of the secretory signal peptide, as shown in FIG. 1 (SEQ ID NO:2). However, subsequent sequencing of the same preparation in another laboratory following storage at −80° C. for several weeks revealed an approximately equal molar mixture of the original mature species and a second species lacking one additional residue, i.e., with the N terminus ending with Thr at position 19 (and thus comprising amino acids 19410 of SEQ ID NO:2). Both species appeared to be efficiently cleaved upon interaction with tPA.

Example 3

Cloning and Expression in Mammalian Cells

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoter from SV40, the long terminal repeats (LTRs) from Retroviruses, e.g., RSV, HTLVI, HIVI and the early promoter of the cytomegalovirus (CMV). However, cellular elements can also be used (e.g., the human actin promoter). Suitable expression vectors for use in practicing the present invention include, for example, vectors such as pSVL and pMSG (Pharmacia, Uppsala, Sweden), pRSVcat (ATCC 371:52), pSV2dhfr (ATCC 37146) and pBC12MI (ATCC 67109). Mammalian host cells that could be used include, human Hela, 293, H9 and Jurkat cells, mouse NIH3T3 and C127 cells, Cos 1, Cos 7 and CV1, quail QC1–3 cells, mouse L cells and Chinese hamster ovary (CHO) cells.

Alternatively, the gene can be expressed in stable cell lines that contain the gene integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) marker is useful to develop cell lines that carry several hundred or even several thousand copies of the gene of interest. Another useful selection marker is the enzyme glutamine synthase (GS) (Murphy et al., *Biochem J.* 227:277–279 (1991); Bebbington it al., *Bio/Technology* 10:169–175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

The expression vectors pC1 and pC4 contain the strong promoter (LTR) of the Rous Sarcoma Virus (Cullen et al., Molecular and Cellular Biology, 438–447 (March, 1985)) plus a fragment of the CMV-enhancer (Boshart et al., Cell 41:521–530 (1985)). Multiple cloning sites, e.g., with the restriction enzyme cleavage sites BamHI, XbaI and Asp718, facilitate the cloning of the gene of interest. The vectors contain in addition the 3' intron, the polyadenylation and termination signal of the rat preproinsulin gene.

Example 3(a)
Cloning and Expression in COS Cells

The expression plasmid, pBAIT HA, is made by cloning a cDNA encoding BAIT into the expression vector pcDNAI/Amp or pcDNAIII (which can be obtained from Invitrogen, Inc.).

The expression vector pcDNAI/amp contains: (1) an *E. coli* origin of replication effective for propagation in *E. coli* and other prokaryotic cells; (2) an ampicillin resistance gene for selection of plasmid-containing prokaryotic cells; (3) an SV40 origin of replication for propagation in eukaryotic cells; (4) a CMV promoter, a polylinker, an SV40 intron; (5) several codons encoding a hemagglutinin fragment (i.e., an "HA" tag to facilitate purification) followed by a termination codon and polyadenylation signal arranged so that a cDNA can be conveniently placed under expression control of the CMV promoter and operably linked to the SV40 intron and the polyadenylation signal by means of restriction sites in the polylinker. The HA tag corresponds to an epitope derived from the influenza hemagglutinin protein described by Wilson et al., *Cell* 37: 767 (1984). The fusion of the HA tag to the target protein allows easy detection and recovery of the recombinant protein with an antibody that recognizes the HA epitope. pcDNAIII contains, in addition, the selectable neomycin marker.

A DNA fragment encoding the BAIT is cloned into the polylinker region of the vector so that recombinant protein expression is directed by the CMV promoter. The plasmid construction strategy is as follows. The BAIT cDNA of the deposited clone is amplified using primers that contain convenient restriction sites, much as described above for construction of vectors for expression of BAIT in *E. coli*. Suitable primers include the following, which are used in this example. The 5' primer, containing the underlined BamHI site, a Kozak sequence, an AUG start codon and 18 nucleotides of the 5' coding region of the complete BAIT has the following sequence: 5' GAGCAT GGATCCGCCATCATGGCTTTCCTTGGCTC 3' (SEQ ID NO:14). The 3' primer, containing the underlined BamHI site and 15 nucleotides complementary to the 3' coding sequence, has the following sequence: 5' GCACAT GGATCCAAGTTCTTCGAAATCATG 3' (SEQ ID NO:15).

The PCR amplified DNA fragment and the vector, pcDNAI/Amp, are digested with BamHI, the vector is dephosphorylated and then the vector and amplified DNA are ligated. The ligation mixture is transformed into *E. coli* strain SURE (available from Stratagene Cloning Systems, 11099 North Torrey Pines Road, La Jolla, Calif. 92037), and the transformed culture is plated on ampicillin media plates which then are incubated to allow growth of ampicillin resistant colonies. Plasmid DNA is isolated from resistant colonies and examined by restriction analysis or other means for the presence of the BAIT-encoding fragment.

For expression of recombinant BAIT, COS cells are transfected with an expression vector, as described above, using DEAE-DEXTRAN, as described, for instance, in Sambrook et al., *Molecular Cloning: a Laboratory Manual*, Cold Spring Laboratory Press, Cold Spring Harbor, N.Y. (1989). Cells are incubated under conditions for expression of BAIT by the vector.

Expression of the BAIT-HA fusion protein is detected by radiolabeling and immunoprecipitation, using methods described in, for example Harlow et al., *Antibodies: A Laboratory Manual, 2nd Ed.;* Cold Spring Harbor Laboratory Press, Cold Spring Harbor, N.Y. (1988). To this end, two days after transfection, the cells are labeled by incubation in media containing $^{35}$S-cysteine for 8 hours. The cells and the media are collected, and the cells are washed and the lysed with detergent-containing RIPA buffer: 150 mM NaCl, 1% NP-40, 0.1% SDS, 1% NP-40, 0.5% DOC, 50 mM TRIS, pH 7.5, as described by Wilson et al. cited above. Proteins are precipitated from the cell lysate and from the culture media using an HA-specific monoclonal antibody. The precipitated proteins then are analyzed by SDS-PAGE and autoradiography. An expression product of the expected size is seen in the cell lysate, which is not seen in negative controls.

Example 3(b)
Cloning and Expression in CHO Cells

The vector pC4 is used for the expression of BAIT protein. Plasmid pC4 is a derivative of the plasmid pSV2-dhfr (ATCC Accession No. 37146) The plasmid contains the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., 1978, *J. Biol. Chem.* 253:1357–1370, Hamlin, J. L. and Ma, C. 1990, *Biochem. et Biophys. Acta,* 1097:107–143, Page, M. J. and Sydenham, M. A. 1991, *Biotechnology* 9:64–68). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach may be used to develop cell lines carrying more than 1,000 copies of the amplified gene(s). Subsequently, when the methotrexate is withdrawn, cell lines are obtained which contain the amplified gene integrated into one or more chromosome(s) of the host cell.

Plasmid pC4 contains for expressing the gene of interest the strong promoter of the long terminal repeat (LTR) of the Rouse Sarcoma Virus (Cullen, et al., *Molecular and Cellular Biology*, March 1985:438–447) plus a fragment isolated from the enhancer of the immediate early gene of human cytomegalovirus (CMV) (Boshart et al., *Cell* 41:521–530 (1985)). Downstream of the promoter are the following single restriction enzyme cleavage sites that allow the integration of the genes: BamHI, Xba I, and Asp718. Behind these cloning sites the plasmid contains the 3' intron and polyadenylation site of the rat preproinsulin gene. Other high efficiency promoters can also be used for the expression, e.g., the human β-actin promoter, the SV40 early or late promoters or the long terminal repeats from other retroviruses, e.g., HIV and HTLVI. Clontech's Tet-Off and Tet-On gene expression systems and similar systems can be used to express the BAIT in a regulated way in mammalian cells (Gossen, M., & Bujard, H. 1992, *Proc. Natl. Acad. Sci. USA* 89: 5547–5551). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with the restriction enzymes BamHI and XbaI and then dephosphorylated using calf intestinal phosphates by procedures known in the art. The vector is then isolated from a 1% agarose gel.

The DNA sequence encoding the complete BAIT protein including its leader sequence is amplified using PCR oligonucleotide primers corresponding to the 5' and 3' sequences of the gene. The 5' primer has the sequence 5' GAGCAT <u>GGATCC</u>GCCATCATGGCTTTCCTTGGACTC 3' (SEQ ID NO:16) containing the underlined BamHI restriction enzyme site followed by an efficient signal for initiation of translation in eukaryotes, as described by Kozak, M., *J. MoL Biol.* 196:947–950 (1987), and 24 bases of the coding sequence of BAIT shown in FIG. 1 (SEQ ID NO:1). The 3' primer has the sequence 5' GAGCAT <u>TCTAGA</u>GTTGCAAACATAATGTGC 3' (SEQ ID NO:17) containing the underlined XbaI restriction site followed by 18 nucleotides complementary to the non-translated region of the BAIT gene shown in FIG. 1 (SEQ ID NO:1).

The amplified fragment is digested with the endonucleases BamHI and XbaI and then purified again on a 1% agarose gel. The isolated fragment and the dephosphorylated vector are then ligated with T4 DNA ligase. *E. coli* HB 101 or XL-1 Blue cells are then transformed and bacteria are identified that contain the fragment inserted into plasmid pC4 using, for instance, restriction enzyme analysis.

Chinese hamster ovary cells lacking an active DHFR gene are used for transfection. Five μg of the expression plasmid pC4 is cotransfected with 0.5 μg of the plasmid pSVneo using lipofectin (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/m G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 μM, 2 μM, 5 μM, 10 mM, 20 mM). The same procedure is repeated until clones are obtained which grow at a concentration of 100–200 μM. Expression of the desired gene product is analyzed, for instance, by SDS-PAGE and Western blot or by reversed phase HPLC analysis.

Example 4
Tissue Distribution of BAIT Protein Expression

Northern blot analysis is carried out to examine BAIT gene expression in human tissues, using methods described by, among others, Sambrook et al., cited above. A cDNA probe containing the entire nucleotide sequence of the BAIT protein (SEQ ID NO:1) is labeled with $^{32}P$ using the rediprime™ DNA labeling system (Amersham Life Science), according to manufacturer's instructions. After labeling, the probe is purified using a CHROMA SPIN-100™ column (Clontech Laboratories, Inc.), according to manufacturer's protocol number PT1200-1. The purified labeled probe is then used to examine various human tissues for BAIT mRNA.

Multiple Tissue Northern (MTN) blots containing various human tissues (H) or human immune system tissues (IM) are obtained from Clontech and are examined with the labeled probe using ExpressHyb™ hybridization solution (Clontech) according to manufacturer's protocol number PT1190-1. Following hybridization and washing, the blots are mounted and exposed to film at −70 C. overnight, and films developed according to standard procedures.

Example 5
Immunohistochemical Analysis of BAIT

To more precisely examine the expression of BAIT protein, immunohistochemical staining of adult mouse tissue sections was performed. Consistent with the mRNA distribution only brain and spinal cord tissues demonstrated significant reactivity. BAIT is widely distributed throughout the brain, but is primarily localized to neurons. The major exceptions to this pattern are expression in the ependymal cells of the choroid plexus, and the brush border of the cells lining the ventricles. These cells are thought to be of microglial origin are important for maintaining the cerebrospinal and ventricular fluid. Other regions of the brain with high BAIT immunoreactivity are the Purkinji cells of the cerebellum which show strongly positive staining of the cell body as well as the axons. Most neurons of the spinal cord are also strongly positive, as are the axons in and the myelinated tracts of the commissura. Another region of strong staining is the hypothalamus where most of the neurons appear to show significant amounts of BAIT immunoreactivity within the cell body. Finally, BAIT was present in the large motor neurons of the medulla oblongata and in scattered neurons throughout the cortex.

Example 6
Comparison of BAIT Inhibitory Activity

A comparison of BAIT inhibitory activity and expression with that of PAI-1 and PN-1, suggests that BAIT has a biological role distinct from these other serpins. While BAIT reacts about 30-fold slower with tPA than does PAI-1, its rate of $6.2 \times 10^5$ $M^{-1}$ $s^{-1}$ it is about 20-fold faster than that of PN-1. In addition, BAIT's primary target enzyme appears to be tPA, since its rate of inhibition of tPA is approximately 25-fold faster than is its rate of inhibition of uPA (Table 1). in contrast, PAI-1 inhibits uPA and tPA with essentially the same rate while PN-1 reacts with uPA about 5-fold faster than it does with tPA. Finally, unlike PAI-1 and PN-1, BAIT's inhibition of thrombin is not stimulated by heparin. Table 1 describes the kinetic constants for the interaction of BAIT with various proteinases.

TABLE I

| Enzyme  | k (s$^{-1}$) | K ($\mu$M) | k$_i$ (M$^{-1}$s$^{-1}$) |
|---------|--------------|------------|--------------------------|
| tctPA   | 0.078        | 0.12       | 6.2 × 10$^5$             |
| sctPA   | 0.17         | 2.1        | 8.0 × 10$^4$             |
| Trypsin | 0.0096       | 0.16       | 5.9 × 10$^4$             |
| uPA-H   | 0.0050       | 0.20       | 2.5 × 10$^4$             |
| uPA-L   | 0.013        | 1.4        | 9.2 × 10$^3$             |

TABLE I-continued

| Enzyme   | k (s$^{-1}$) | K ($\mu$M) | k$_i$ (M$^{-1}$s$^{-1}$) |
|----------|--------------|------------|--------------------------|
| NGF-$\gamma$ | 0.0086   | 1.3        | 6.5 × 10$^3$             |
| Plasmin  | 0.000052     | 0.15       | 3.6 × 10$^2$             |
| Thrombin | 0.00013      | 0.64       | 2.1 × 10$^2$             |

The abbreviations are tctPA, human two-chain tPA: sctPA, human single-chain tPA, uPA-H, human high molecular weight uPA; uPA-L, human low molecular weight uPA; trypsin, bovine beta trypsin; and NGF-gamma, rat nerve growth factor gamma.

What is claimed is:

1. An isolated polynucleotide comprising a nucleic acid sequence selected from the group consisting of:
   (a) a nucleic acid sequence encoding amino acids −18 to +392 of SEQ ID NO:2;
   (b) a nucleic acid sequence encoding a mature portion of the protein of SEQ ID NO:2;
   (c) a nucleic acid sequence encoding the complete amino acid sequence encoded by the cDNA contained in ATCC Deposit No. 97722;
   (d) a nucleic acid sequence encoding a mature protein encoded by the cDNA contained in ATCC Deposit No. 97722; and
   (e) the complement of (a), (b), (c), or (d).

2. The isolated polynucleotide of claim 1, wherein said nucleic acid sequence is (a).

3. The isolated polynucleotide of claim 2, wherein said nucleic acid sequence comprises nucleotides +89 to +1318 of SEQ ID NO:1.

4. The isolated polynucleotide of claim 1, wherein said nucleic acid sequence is (b).

5. The isolated polynucleotide of claim 4, wherein said mature portion comprises amino acids +1 to +392 of SEQ ID NO:2.

6. The isolated polynucleotide of claim 5, wherein said nucleic acid sequence comprises nucleotides +143 to +1318 of SEQ ID NO:1.

7. The isolated polynucleotide of claim 4, wherein said mature portion comprises amino acids +2 to +392 of SEQ ID NO:2.

8. The isolated polynucleotide of claim 7, wherein said nucleic acid sequence comprises nucleotides +146 to +1318 of SEQ ID NO:1.

9. The isolated polynucleotide of claim 4, wherein said mature portion comprises amino acids +4 to +392 of SEQ ID NO:2.

10. The isolated polynucleotide of claim 9, wherein said nucleic acid sequence comprises nucleotides +152 to +1318 of SEQ ID NO:1.

11. The isolated-polynucleotide of claim 1, wherein said nucleic acid sequence is (c).

12. The isolated polynucleotide of claim 1, wherein said nucleic acid sequence is (d).

13. The isolated polynucleotide of claim 1, wherein said nucleic acid sequence is (e).

14. The isolated polynucleotide of claim 2 further comprising a heterologous polynucleotide.

15. The isolated polynucleotide of claim 4 further comprising a heterologous polynucleotide.

16. The isolated polynucleotide of claim 11 further comprising a heterologous polynucleotide.

17. The isolated polynucleotide of claim 12 further comprising a heterologous polynucleotide.

18. The isolated polynucleotide of claim 14, wherein the heterologous polynucleotide encodes a heterologous polypeptide.

19. The isolated polynucleotide of claim 15, wherein the heterologous polynucleotide encodes a heterologous polypeptide.

20. The isolated polynucleotide of claim 16, wherein the heterologous polynucleotide encodes a heterologous polypeptide.

21. The isolated polynucleotide of claim 17, wherein the heterologous polynucleotide encodes a heterologous polypeptide.

22. A recombinant vector comprising the polynucleotide of claim 2.

23. A recombinant vector comprising the polynucleotide of claim 4.

24. A recombinant vector comprising the polynucleotide of claim 11.

25. A recombinant vector comprising the polynucleotide of claim 12.

26. A host cell comprising the polynucleotide of claim 2 operably associated with a heterologous regulatory sequence.

27. A host cell comprising the polynucleotide of claim 4 operably associated with a heterologous regulatory sequence.

28. A host cell comprising the polynucleotide of claim 11 operably associated with a heterologous regulatory sequence.

29. A host cell comprising the polynucleotide of claim 12 operably associated with a heterologous regulatory sequence.

30. A method of producing a polypeptide comprising:
(a) culturing the host cell of claim 26 whereby the polypeptide is produced; and
(b) recovering said polypeptide.

31. A method of producing a polypeptide comprising:
(a) culturing the host cell of claim 27 whereby the polypeptide is produced; and
(b) recovering said polypeptide.

32. A method of producing a polypeptide comprising:
(a) culturing the host cell of claim 28 whereby the polypeptide is produced; and
(b) recovering said polypeptide.

33. A method of producing a polypeptide comprising:
(a) culturing the host cell of claim 29 whereby the polypeptide is produced; and
(b) recovering said polypeptide.

34. An isolated polynucleotide comprising a nucleic acid sequence selected from the group consisting of:
(a) a nucleic acid sequence encoding a polypeptide having the amino acid sequence consisting of residues n-392 of SEQ ID NO:2, where n is an integer in the range of −17 to +31;
(b) a nucleic acid sequence encoding a polypeptide having the amino acid sequence consisting of residues −18-m of SEQ ID NO:2, where m is an integer in the range of +363 to +391;
(c) a nucleic acid sequence encoding a polypeptide having the amino acid sequence consisting of residues n–m of SEQ ID NO:2, where n is an integer in the range of −17 to +31 and m is an integer in the range of +363 to +391; and
(d) a nucleic acid sequence encoding a polypeptide consisting of a portion of the complete amino acid sequence encoded by the cDNA clone contained in ATCC Deposit 97722 wherein said portion excludes up to 48 amino acids from the amino terminus and up to 30 amino acids from the C-terminus of said complete amino acid sequence.

35. The isolated polynucleotide of claim 34, wherein said nucleic acid sequence is (a).

36. The isolated polynucleotide of claim 34, wherein said nucleic acid sequence is (b).

37. The isolated polynucleotide of claim 34, wherein said nucleic acid sequence is (c).

38. The isolated polynucleotide of claim 34, wherein said nucleic acid sequence is (d).

39. The isolated polynucleotide of claim 34 further comprising a heterologous polynucleotide.

40. The isolated polynucleotide of claim 39, wherein the heterologous polynucleotide encodes a heterologous polypeptide.

41. A recombinant vector comprising the polynucleotide of claim 34.

42. A host cell comprising the polynucleotide of claim 34 operably associated with a heterologous regulatory sequence.

43. A method of producing a polypeptide comprising:
(a) culturing the host cell of claim 42 whereby the polypeptide is produced; and
(b) recovering said polypeptide.

\* \* \* \* \*

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
      (A) LENGTH: 1564 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 89..1318

(ix) FEATURE:
      (A) NAME/KEY: sig_peptide
      (B) LOCATION: 89..140

(ix) FEATURE:
      (A) NAME/KEY: mat_peptide
      (B) LOCATION: 143..1318

(xi) SEQUENCE DESCRIPTION: SEQ ID NO:1:

```
GAGCGGAGCG GAGCACAGTC CGCCGAGCAC AAGCTCCAGC ATCCCGTCAG GGGTTGCAGG      60

TGTGTGGGAG GCTTGAAACT GTTACAAT ATG GCT TTC CTT GGA CTC TTC TCT        112
                               Met Ala Phe Leu Gly Leu Phe Ser
                               -18                 -15

TTG CTG GTT CTG CAA AGT ATG GCT ACA GGG GCC ACT TTC CCT GAG GAA       160
Leu Leu Val Leu Gln Ser Met Ala Thr Gly Ala Thr Phe Pro Glu Glu
-10                 -5                  1                   5

GCC ATT GCT GAC TTG TCA GTG AAT ATG TAT AAT CGT CTT AGA GCC ACT       208
Ala Ile Ala Asp Leu Ser Val Asn Met Tyr Asn Arg Leu Arg Ala Thr
            10                  15                  20

GGT GAA GAT GAA AAT ATT CTC TTC TCT CCA TTG AGT ATT GCT CTT GCA       256
Gly Glu Asp Glu Asn Ile Leu Phe Ser Pro Leu Ser Ile Ala Leu Ala
        25                  30                  35

ATG GGA ATG ATG GAA CTT GGG GCC CAA GGA TCT ACC CAG AAA GAA ATC       304
Met Gly Met Met Glu Leu Gly Ala Gln Gly Ser Thr Gln Lys Glu Ile
    40                  45                  50

CGC CAC TCA ATG GGA TAT GAC AGC CTA AAA AAT GGT GAA GAA TTT TCT       352
Arg His Ser Met Gly Tyr Asp Ser Leu Lys Asn Gly Glu Glu Phe Ser
55                  60                  65                  70
```

| | |
|---|---|
| TTC TTG AAG GAG TTT TCA AAC ATG GTA ACT GCT AAA GAG AGC CAA TAT<br>Phe Leu Lys Glu Phe Ser Asn Met Val Thr Ala Lys Glu Ser Gln Tyr<br>              75                          80                        85 | 400 |
| GTG ATG AAA ATT GCC AAT TCC TTG TTT GTG CAA AAT GGA TTT CAT GTC<br>Val Met Lys Ile Ala Asn Ser Leu Phe Val Gln Asn Gly Phe His Val<br>              90                          95                        100 | 448 |
| AAT GAG GAG TTT TTG CAA ATG ATG AAA AAA TAT TTT AAT GCA GCA GTA<br>Asn Glu Glu Phe Leu Gln Met Met Lys Lys Tyr Phe Asn Ala Ala Val<br>              105                        110                        115 | 496 |
| AAT CAT GTG GAC TTC AGT CAA AAT GTA GCC GTG GCC AAC TAC ATC AAT<br>Asn His Val Asp Phe Ser Gln Asn Val Ala Val Ala Asn Tyr Ile Asn<br>120                        125                        130 | 544 |
| AAG TGG GTG GAG AAT AAC ACA AAC AAT CTG GTG AAA GAT TTG GTA TCC<br>Lys Trp Val Glu Asn Asn Thr Asn Asn Leu Val Lys Asp Leu Val Ser<br>135                        140                        145                        150 | 592 |
| CCA AGG GAT TTT GAT GCT GCC ACT TAT CTG GCC CTC ATT AAT GCT GTC<br>Pro Arg Asp Phe Asp Ala Ala Thr Tyr Leu Ala Leu Ile Asn Ala Val<br>                          155                        160                        165 | 640 |
| TAT TTC AAG GGG AAC TGG AAG TCG CAG TTT AGG CCT GAA AAT ACT AGA<br>Tyr Phe Lys Gly Asn Trp Lys Ser Gln Phe Arg Pro Glu Asn Thr Arg<br>              170                        175                        180 | 688 |
| ACC TTT TCT TTC ACT AAA GAT GAT GAA AGT GAA GTC CAA ATT CCA ATG<br>Thr Phe Ser Phe Thr Lys Asp Asp Glu Ser Glu Val Gln Ile Pro Met<br>              185                        190                        195 | 736 |
| ATG TAT CAG CAA GGA GAA TTT TAT TAT GGG GAA TTT AGT GAT GGC TCC<br>Met Tyr Gln Gln Gly Glu Phe Tyr Tyr Gly Glu Phe Ser Asp Gly Ser<br>        200                        205                        210 | 784 |
| AAT GAA GCT GGT GGT ATC TAC CAA GTC CTA GAA ATA CCA TAT GAA GGA<br>Asn Glu Ala Gly Gly Ile Tyr Gln Val Leu Glu Ile Pro Tyr Glu Gly<br>215                        220                        225                        230 | 832 |
| GAT GAA ATA AGC ATG ATG CTG GTG CTG TCC AGA CAG GAA GTT CCT CTT<br>Asp Glu Ile Ser Met Met Leu Val Leu Ser Arg Gln Glu Val Pro Leu<br>                          235                        240                        245 | 880 |
| GCT ACT CTG GAG CCA TTA GTC AAA GCA CAG CTG GTT GAA GAA TGG GCA<br>Ala Thr Leu Glu Pro Leu Val Lys Ala Gln Leu Val Glu Glu Trp Ala<br>              250                        255                        260 | 928 |
| AAC TCT GTG AAG AAG CAA AAA GTA GAA GTA TAC CTG CCC AGG TTC ACA<br>Asn Ser Val Lys Lys Gln Lys Val Glu Val Tyr Leu Pro Arg Phe Thr<br>                265                        270                        275 | 976 |
| GTG GAA CAG GAA ATT GAT TTA AAA GAT GTT TTG AAG GCT CTT GGA ATA<br>Val Glu Gln Glu Ile Asp Leu Lys Asp Val Leu Lys Ala Leu Gly Ile<br>        280                        285                        290 | 1024 |
| ACT GAA ATT TTC ATC AAA GAT GCA AAT TTG ACA GGC CTC TCT GAT AAT<br>Thr Glu Ile Phe Ile Lys Asp Ala Asn Leu Thr Gly Leu Ser Asp Asn<br>295                        300                        305                        310 | 1072 |
| AAG GAG ATT TTT CTT TCC AAA GCA ATT CAC AAG TCC TTC CTA GAG GTT<br>Lys Glu Ile Phe Leu Ser Lys Ala Ile His Lys Ser Phe Leu Glu Val<br>                315                        320                        325 | 1120 |
| AAT GAA GAA GGC TCA GAA GCT GCT GCT GTC TCA GGA ATG ATT GCA ATT<br>Asn Glu Glu Gly Ser Glu Ala Ala Ala Val Ser Gly Met Ile Ala Ile<br>                  330                        335                        340 | 1168 |
| AGT AGG ATG GCT GTG CTG TAT CCT CAA GTT ATT GTC GAC CAT CCA TTT<br>Ser Arg Met Ala Val Leu Tyr Pro Gln Val Ile Val Asp His Pro Phe<br>              345                        350                        355 | 1216 |
| TTC TTT CTT ATC AGA AAC AGG AGA ACT GGT ACA ATT CTA TTC ATG GGA<br>Phe Phe Leu Ile Arg Asn Arg Arg Thr Gly Thr Ile Leu Phe Met Gly<br>        360                        365                        370 | 1264 |
| CGA GTC ATG CAT CCT GAA ACA ATG AAC ACA AGT GGA CAT GAT TTC GAA<br>Arg Val Met His Pro Glu Thr Met Asn Thr Ser Gly His Asp Phe Glu<br>375                        380                        385                        390 | 1312 |

-continued

```
GAA CTT TAAGTTACTT TATTTGAATA ACAAGGAAAA CAGTAACTAA GCACATTATG    1368
Glu Leu
TTTGCAACTG GTATATATTT AGGATTTGTG TTTTACAGTA TATCTTAAGA TAATATTTAA    1428

AATAGTTCCA GATAAAAACA ATATATGTAA ATTATAAGTA ACTTGTCAAG GAATGTTATC    1488

AGTATTAAGC TAATGGTCCT GTTATGTCAT TGTGTTTGTG TGCTGTTGTT TAAAATAAAA    1548

GTACCTATTG AACATG                                                    1564
```

(2) INFORMATION FOR SEQ ID NO:2:

(i) SEQUENCE CHARACTERISTICS:
        (A) LENGTH: 410 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ala Phe Leu Gly Leu Phe Ser Leu Leu Val Leu Gln Ser Met Ala
-18         -15              -10              -5
Thr Gly Ala Thr Phe Pro Glu Glu Ala Ile Ala Asp Leu Ser Val Asn
              1               5                  10
Met Tyr Asn Arg Leu Arg Ala Thr Gly Glu Asp Glu Asn Ile Leu Phe
 15               20              25              30
Ser Pro Leu Ser Ile Ala Leu Ala Met Gly Met Glu Leu Gly Ala
                 35              40              45
Gln Gly Ser Thr Gln Lys Glu Ile Arg His Ser Met Gly Tyr Asp Ser
             50              55              60
Leu Lys Asn Gly Glu Glu Phe Ser Phe Leu Lys Glu Phe Ser Asn Met
         65              70              75
Val Thr Ala Lys Glu Ser Gln Tyr Val Met Lys Ile Ala Asn Ser Leu
     80              85              90
Phe Val Gln Asn Gly Phe His Val Asn Glu Glu Phe Leu Gln Met Met
 95              100             105             110
Lys Lys Tyr Phe Asn Ala Ala Val Asn His Val Asp Phe Ser Gln Asn
             115             120             125
Val Ala Val Ala Asn Tyr Ile Asn Lys Trp Val Glu Asn Asn Thr Asn
         130             135             140
Asn Leu Val Lys Asp Leu Val Ser Pro Arg Asp Phe Asp Ala Ala Thr
     145             150             155
Tyr Leu Ala Leu Ile Asn Ala Val Tyr Phe Lys Gly Asn Trp Lys Ser
 160             165             170
Gln Phe Arg Pro Glu Asn Thr Arg Thr Phe Ser Phe Thr Lys Asp Asp
 175             180             185             190
Glu Ser Glu Val Gln Ile Pro Met Met Tyr Gln Gln Gly Glu Phe Tyr
             195             200             205
Tyr Gly Glu Phe Ser Asp Gly Ser Asn Glu Ala Gly Gly Ile Tyr Gln
         210             215             220
Val Leu Glu Ile Pro Tyr Glu Gly Asp Glu Ile Ser Met Met Leu Val
     225             230             235
Leu Ser Arg Gln Glu Val Pro Leu Ala Thr Leu Glu Pro Leu Val Lys
 240             245             250
Ala Gln Leu Val Glu Glu Trp Ala Asn Ser Val Lys Lys Gln Lys Val
255             260             265             270
Glu Val Tyr Leu Pro Arg Phe Thr Val Glu Gln Glu Ile Asp Leu Lys
             275             280             285
Asp Val Leu Lys Ala Leu Gly Ile Thr Glu Ile Phe Ile Lys Asp Ala
```

```
                    290                 295                 300
Asn Leu Thr Gly Leu Ser Asp Asn Lys Glu Ile Phe Leu Ser Lys Ala
            305                 310                 315
Ile His Lys Ser Phe Leu Glu Val Asn Glu Glu Gly Ser Glu Ala Ala
            320                 325                 330
Ala Val Ser Gly Met Ile Ala Ile Ser Arg Met Ala Val Leu Tyr Pro
335                 340                 345                 350
Gln Val Ile Val Asp His Pro Phe Phe Leu Ile Arg Asn Arg Arg
                355                 360                 365
Thr Gly Thr Ile Leu Phe Met Gly Arg Val Met His Pro Glu Thr Met
                370                 375                 380
Asn Thr Ser Gly His Asp Phe Glu Glu Leu
            385                 390
```

(2) INFORMATION FOR SEQ ID NO:3:

(i) SEQUENCE CHARACTERISTICS:
        (A) LENGTH: 407 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

```
Met Tyr Phe Leu Gly Leu Leu Ser Leu Leu Val Leu Pro Ser Lys Ala
1               5                   10                  15
Phe Lys Thr Asn Phe Pro Asp Glu Thr Ile Ala Glu Leu Ser Asn Val
                20                  25                  30
Tyr Asn Leu Arg Ala Ala Arg Glu Asp Glu Asn Ile Leu Phe Cys Pro
            35                  40                  45
Leu Ser Ile Ala Ile Ala Met Gly Met Ile Glu Leu Gly Ala His Gly
    50                  55                  60
Thr Thr Leu Lys Glu Ile Arg His Ser Leu Gly Phe Asp Ser Leu Lys
65                  70                  75                  80
Asn Gly Glu Glu Phe Thr Phe Leu Lys Asp Leu Ser Asp Met Ala Thr
                85                  90                  95
Thr Glu Glu Ser His Tyr Val Leu Asn Met Ala Asn Ser Leu Tyr Val
                100                 105                 110
Gln Asn Gly Phe His Val Ser Glu Lys Phe Leu Gln Leu Val Lys Lys
            115                 120                 125
Tyr Phe Lys Ala Glu Val Glu Asn Ile Asp Phe Ser Gln Ser Ala Ala
    130                 135                 140
Val Ala Thr His Ile Asn Lys Trp Val Glu Asn Thr Asn Asn Met
145                 150                 155                 160
Ile Lys Asp Phe Val Ser Ser Arg Asp Phe Ser Ala Leu Thr His Val
                165                 170                 175
Leu Ile Asn Ala Ile Tyr Phe Lys Gly Asn Trp Lys Ser Gln Phe Arg
            180                 185                 190
Pro Glu Asn Thr Arg Thr Phe Ser Phe Thr Lys Asp Asp Glu Thr Glu
        195                 200                 205
Val Gln Ile Pro Met Met Tyr Gln Gln Gly Glu Pro Tyr Tyr Gly Glu
    210                 215                 220
Phe Ser Asp Gly Ser Asn Glu Ala Gly Gly Ile Tyr Gln Val Leu Glu
225                 230                 235                 240
Ile Pro Tyr Glu Gly Asp Glu Ile Ser Met Met Ile Val Leu Ser Arg
                245                 250                 255
```

```
Gln Glu Val Pro Leu Val Thr Leu Pro Leu Val Lys Ala Ser Leu
            260                 265                 270

Ile Asn Glu Trp Ala Asn Ser Val Lys Lys Gln Lys Val Glu Val Tyr
            275                 280                 285

Leu Pro Arg Phe Thr Val Glu Gln Glu Ile Asp Leu Lys Asp Val Leu
            290                 295                 300

Lys Gly Leu Gly Ile Thr Glu Val Phe Ser Arg Ser Ala Asp Leu Thr
305                 310                 315                 320

Ala Met Ser Asp Asn Lys Glu Leu Tyr Leu Ala Lys Ala Phe His Lys
                325                 330                 335

Ala Phe Leu Glu Val Asn Glu Glu Gly Ser Glu Ala Ala Ala Ala Ser
                340                 345                 350

Gly Met Ile Ala Ile Ser Arg Met Ala Val Leu Tyr Pro Gln Val Ile
                355                 360                 365

Val Asp His Pro Phe Phe Phe Leu Val Arg Asn Arg Arg Thr Gly Thr
                370                 375                 380

Val Leu Phe Met Gly Arg Val Met His Pro Glu Ala Met Asn Thr Ser
385                 390                 395                 400

Gly His Asp Phe Glu Glu Leu
                405

(2) INFORMATION FOR SEQ ID NO:4:

(i) SEQUENCE CHARACTERISTICS:
        (A) LENGTH: 402 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

Met Arg Met Ser Pro Val Phe Ala Cys Leu Ala Leu Gly Leu Ala Leu
1               5                   10                  15

Ile Phe Gly Glu Gly Ser Ala Ser Tyr Gln Pro Gln Ser Ala Ala Ala
                20                  25                  30

Ser Leu Ala Thr Asp Phe Gly Val Lys Val Phe Gln Gln Val Val Arg
            35                  40                  45

Ala Ser Lys Asp Arg Asn Val Val Phe Ser Pro Tyr Gly Val Ala Ser
50                  55                  60

Val Leu Ala Met Leu Gln Leu Thr Thr Gly Gly Glu Thr Arg Gln Gln
65                  70                  75                  80

Ile Gln Glu Ala Met Gln Phe Lys Ile Glu Glu Lys Gly Met Ala Pro
                85                  90                  95

Ala Phe His Arg Leu Tyr Lys Glu Leu Met Gly Pro Trp Asn Lys Asp
                100                 105                 110

Glu Ile Ser Thr Ala Asp Ala Ile Phe Val Gln Arg Asp Leu Glu Leu
            115                 120                 125

Val His Gly Phe Met Pro Asn Phe Phe Arg Leu Phe Arg Thr Thr Val
            130                 135                 140

Lys Gln Val Asp Phe Ser Glu Val Glu Arg Ala Arg Phe Ile Val Asn
145                 150                 155                 160

Asp Trp Val Lys Arg His Thr Lys Gly Met Ile Ser Asp Leu Leu Gly
                165                 170                 175

Glu Gly Ala Val Asp Gln Leu Thr Arg Leu Val Leu Val Asn Ala Leu
                180                 185                 190
```

```
Tyr Phe Asn Gly Gln Trp Lys Met Pro Phe Pro Glu Ser Asn Thr His
        195                 200                 205

His Arg Leu Phe His Lys Ser Asp Gly Ser Thr Ile Ser Val Pro Met
    210                 215                 220

Met Ala Gln Thr Asn Lys Phe Asn Tyr Thr Glu Phe Thr Thr Pro Asp
225                 230                 235                 240

Gly Arg Tyr Tyr Asp Ile Leu Glu Leu Pro Tyr His Gly Asn Thr Leu
                245                 250                 255

Ser Met Leu Ile Ala Ala Pro Tyr Glu Lys Glu Val Pro Leu Ser Ala
                260                 265                 270

Leu Thr Ser Ile Leu Asp Ala Glu Leu Ile Ser Gln Trp Lys Gly Asn
            275                 280                 285

Met Thr Arg Leu Thr Arg Leu Leu Val Leu Pro Lys Phe Ser Leu Glu
        290                 295                 300

Thr Glu Ile Asp Leu Arg Arg Pro Leu Glu Asn Leu Gly Met Thr Asp
305                 310                 315                 320

Met Phe Arg Pro Ser Gln Ala Asp Phe Ser Ser Phe Ser Asp Gln Glu
                325                 330                 335

Phe Leu Tyr Val Ser Gln Ala Leu Gln Lys Val Lys Ile Glu Val Asn
                340                 345                 350

Glu Ser Gly Thr Leu Ala Ser Ser Ser Thr Ala Leu Val Val Ser Ala
            355                 360                 365

Arg Met Ala Pro Glu Glu Ile Ile Met Asp Arg Pro Phe Leu Phe Val
        370                 375                 380

Val Arg His Asn Pro Thr Gly Thr Val Leu Phe Met Gly Gln Val Met
385                 390                 395                 400

Glu Pro (2) INFORMATION FOR SEQ ID NO:5:

(i) SEQUENCE CHARACTERISTICS:
        (A) LENGTH: 397 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

Met Asn Trp His Phe Pro Phe Phe Ile Leu Thr Thr Val Thr Leu Ser
1               5                   10                  15

Ser Val Tyr Ser Gln Leu Asn Ser Leu Ser Leu Glu Glu Leu Gly Ser
                20                  25                  30

Asp Thr Gly Ile Gln Val Phe Asn Gln Ile Ile Lys Ser Gln Pro His
            35                  40                  45

Glu Asn Val Val Ile Ser Pro His Gly Ile Ala Ser Ile Leu Gly Met
    50                  55                  60

Leu Gln Leu Gly Ala Asp Gly Arg Thr Lys Lys Gln Leu Ser Thr Val
65                  70                  75                  80

Met Arg Tyr Asn Val Asn Gly Val Gly Lys Val Leu Lys Lys Ile Asn
                85                  90                  95

Lys Ala Ile Val Ser Lys Asn Lys Asp Ile Val Thr Val Ala Asn
            100                 105                 110

Ala Val Phe Val Arg Asn Gly Phe Lys Val Glu Val Pro Phe Ala Ala
            115                 120                 125

Arg Asn Lys Glu Val Phe Gln Cys Glu Val Gln Ser Val Asn Phe Gln
    130                 135                 140
```

Asp Pro Ala Ser Ala Cys Asp Ala Ile Asn Phe Trp Val Lys Asn Glu
145                 150                 155                 160

Thr Arg Gly Met Ile Asp Asn Leu Leu Ser Pro Asn Leu Ile Asp Ser
            165                 170                 175

Ala Leu Thr Lys Leu Val Leu Val Asn Ala Val Tyr Phe Lys Gly Leu
        180                 185                 190

Trp Lys Ser Arg Phe Gln Pro Glu Asn Thr Lys Lys Arg Thr Phe Val
    195                 200                 205

Ala Gly Asp Gly Lys Ser Tyr Gln Val Pro Met Leu Ala Gln Leu Ser
210                 215                 220

Val Phe Arg Ser Gly Ser Thr Lys Thr Pro Asn Gly Leu Trp Tyr Asn
225                 230                 235                 240

Phe Ile Glu Leu Pro Tyr His Gly Glu Ser Ile Ser Met Leu Ile Ala
                245                 250                 255

Leu Pro Thr Glu Ser Ser Thr Pro Leu Ser Ala Ile Ile Pro His Ile
            260                 265                 270

Ser Thr Lys Thr Ile Asn Ser Trp Met Asn Thr Met Val Pro Lys Arg
        275                 280                 285

Met Gln Leu Val Leu Pro Lys Phe Thr Ala Leu Ala Gln Thr Asp Leu
    290                 295                 300

Lys Glu Pro Leu Lys Ala Leu Gly Ile Thr Glu Met Phe Glu Pro Ser
305                 310                 315                 320

Lys Ala Asn Phe Ala Lys Ile Thr Arg Ser Glu Ser Leu His Val Ser
                325                 330                 335

His Ile Leu Gln Lys Ala Lys Ile Glu Val Ser Glu Asp Gly Thr Lys
            340                 345                 350

Ala Ala Val Val Thr Thr Ala Ile Leu Ile Ala Arg Ser Ser Pro Pro
        355                 360                 365

Trp Phe Ile Val Asp Arg Pro Phe Leu Phe Cys Ile Arg His Asn Pro
    370                 375                 380

Thr Gly Ala Ile Leu Phe Leu Gly Gln Val Asn Lys Pro
385                 390                 395

(2) INFORMATION FOR SEQ ID NO:6:

(i) SEQUENCE CHARACTERISTICS:
        (A) LENGTH: 465 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

Met Tyr Ser Pro Gly Ala Gly Ser Gly Ala Ala Gly Glu Arg Lys Leu
1               5                   10                  15

Cys Leu Leu Ser Leu Leu Ile Gly Ala Leu Gly Cys Ala Ile Cys
            20                  25                  30

His Gly Asn Pro Val Asp Ile Cys Ile Ala Lys Pro Arg Asp Ile
        35                  40                  45

Pro Val Asn Pro Leu Cys Ile Tyr Arg Ser Pro Gly Lys Lys Ala Thr
    50                  55                  60

Glu Glu Asp Gly Ser Glu Gln Lys Val Pro Glu Ala Thr Asn Arg Arg
65                  70                  75                  80

Val Trp Glu Leu Ser Lys Ala Asn Ser Arg Phe Ala Thr Asn Phe Tyr
            85                  90                  95

-continued

```
Gln His Leu Ala Asp Ser Lys Asn Asp Asn Asp Ile Phe Leu Ser
            100                 105                 110

Pro Leu Ser Ile Ser Thr Ala Phe Ala Met Thr Lys Leu Gly Ala Cys
        115                 120                 125

Asn Asp Thr Leu Lys Gln Leu Met Glu Val Phe Lys Phe Asp Thr Ile
    130                 135                 140

Ser Glu Lys Thr Ser Asp Gln Ile His Phe Phe Phe Ala Lys Leu Asn
145                 150                 155                 160

Cys Arg Leu Tyr Arg Lys Ala Asn Lys Ser Ser Asp Leu Val Ser Ala
                165                 170                 175

Asn Arg Leu Phe Gly Asp Lys Ser Leu Thr Phe Asn Glu Ser Tyr Gln
            180                 185                 190

Asp Val Ser Glu Val Val Tyr Gly Ala Lys Leu Gln Pro Leu Asp Phe
        195                 200                 205

Lys Glu Asn Pro Glu Gln Ser Arg Val Thr Ile Asn Asn Trp Val Ala
    210                 215                 220

Asn Lys Thr Glu Gly Arg Ile Lys Asp Val Ile Pro Gln Gly Ala Ile
225                 230                 235                 240

Asn Glu Leu Thr Ala Leu Val Leu Val Asn Thr Ile Tyr Phe Lys Gly
                245                 250                 255

Leu Trp Lys Ser Lys Phe Ser Pro Glu Asn Thr Arg Lys Glu Pro Phe
            260                 265                 270

Tyr Lys Val Asp Gly Gln Ser Cys Pro Val Pro Met Met Tyr Gln Glu
        275                 280                 285

Gly Lys Phe Lys Tyr Arg Arg Val Ala Glu Gly Thr Gln Val Leu Glu
    290                 295                 300

Leu Pro Phe Lys Gly Asp Asp Ile Thr Met Val Leu Ile Leu Pro Lys
305                 310                 315                 320

Pro Glu Lys Ser Leu Ala Lys Val Glu Gln Glu Leu Thr Pro Glu Leu
                325                 330                 335

Leu Gln Glu Trp Leu Asp Glu Leu Ser Glu Thr Met Leu Val Val His
            340                 345                 350

Met Pro Arg Phe Arg Thr Glu Asp Gly Phe Ser Leu Lys Glu Gln Leu
        355                 360                 365

Gln Asp Met Gly Leu Ile Asp Leu Phe Ser Pro Glu Lys Ser Gln Leu
    370                 375                 380

Pro Gly Ile Val Ala Gly Gly Arg Asp Asp Leu Tyr Val Ser Asp Ala
385                 390                 395                 400

Phe His Lys Ala Phe Leu Glu Val Asn Glu Glu Gly Ser Glu Ala Ala
                405                 410                 415

Ala Ser Thr Ser Val Val Ile Thr Gly Arg Ser Leu Asn Pro Asn Arg
            420                 425                 430

Val Thr Phe Lys Ala Asn Arg Pro Phe Leu Val Leu Ile Arg Glu Val
        435                 440                 445

Ala Leu Asn Thr Ile Ile Phe Met Gly Arg Val Ala Asn Pro Cys Val
    450                 455                 460

Asn
465

(2) INFORMATION FOR SEQ ID NO:7:

(i) SEQUENCE CHARACTERISTICS:
        (A) LENGTH: 353 base pairs
        (B) TYPE: nucleic acid
        (C) STRANDEDNESS: single
        (D) TOPOLOGY: linear
```

(ii) MOLECULE TYPE: DNA (genomic)

(xi) SEQUENCE DESCRIPTION: SEQ ID NO:7:

| | | | | | |
|---|---|---|---|---|---|
| GGAAGTTCCT | CTTGCTACTC | TGGAGCCATT | AGTCAAAGCA | CAGCTGGTTG | AAGAATGGGC | 60 |
| AAACTCTGTG | AAGAAGCAAA | AAGTAGAAGT | ATACCTGCCC | AGGTTCACAG | TGGAACAGGA | 120 |
| AATTGATTTA | AAAGATGTTT | TGAAGGCTCT | TGGAATAACT | GAAATTTTCA | TCAAAGATGC | 180 |
| AAATTTGACA | GGCCTCTCTG | ATAATAAGGA | GATTTTTCTT | TCCAAAGCAA | TTCACAAGTC | 240 |
| CTTCCTAGAG | GTTAAATGAA | GGAAGGCTCC | AGAAGCTGCT | GCTGGTCTTC | AGGAATGATT | 300 |
| TGCAATTAGT | AGGGTTGGCT | GTCTGTATCC | CTCAAGGTTA | TTGTCGGCCA | TCC | 353 |

(2) INFORMATION FOR SEQ ID NO:8:

(i) SEQUENCE CHARACTERISTICS:
        (A) LENGTH: 352 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

| | | | | | |
|---|---|---|---|---|---|
| AGACAGGAAG | TTCCTCTTGC | TACTCTGGAG | CCATTAGTCA | AAGCACAGCT | GGTTGAAGAN | 60 |
| TGGGCAAACT | CTGTNAAGAA | GCAAAAAGTA | GAAGTATACC | TGCCCAGGTT | CACAGTGGAA | 120 |
| CAGGAAATTN | ATTTAAAAGA | TGTTTTGAAG | GCTCTTGGAA | TAACTGAAAT | TTTCATCAAA | 180 |
| GATGCAAATT | TGACAGGCCT | CTCTGATAAT | AAGGAGATTT | TCNTTTCCAA | AGCAATTCAC | 240 |
| AAGTCCTTCC | TAGAGGTTAA | TGNAGGAGGC | TCCAGAAGCT | GCTGCTGTCT | CAGGGATGAT | 300 |
| TTGCAATTTA | NGTAGGNTGG | GCTGTGCTGG | TATCCNCAAG | GTTATTTTTC | GG | 352 |

(2) INFORMATION FOR SEQ ID NO:9:

(i) SEQUENCE CHARACTERISTICS:
        (A) LENGTH: 399 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

| | | | | | |
|---|---|---|---|---|---|
| GGAAGTTCCT | CTTGCTACTC | TGGAGCCATT | AGTCAAAGCA | CAGCTGGTTG | AAGAATGGGC | 60 |
| AAACTCTGTG | AAGAAGCAAA | AAGTAGAAGT | ATACCTGCCC | AGGTTCACAG | TGGAACAGGA | 120 |
| AATTGATTTA | AAAGATGTTT | TGAAGGCTCT | TGGAATAACT | GAAATTTTCA | TCAAAGATGC | 180 |
| AAATTTGACA | GGCCTCTCTG | ATAATAAGGA | GATTTTTCTT | TCCAAAGCAA | TTCACAAGTC | 240 |
| CTTCCTAGAG | GTTAATGAAG | AAGGCTCAGA | AGCTGCTGCT | TGTCTCAGGA | ATGATTGCAA | 300 |
| TTAGTAGGAT | GGCTGTGCTG | TATCCTCAAG | GTTATTGTCG | ACCATCCATT | TTTCCTTTCT | 360 |
| TATCAGAACC | AGGGGACCTG | GTACAATTCT | ATTCATGGG | | | 399 |

(2) INFORMATION FOR SEQ ID NO:10:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

GAGCATGGAT CCGCCACTTT CCCTGAGGAA                                   30

(2) INFORMATION FOR SEQ ID NO:11:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

GCACATGGAT CCTTAAAGTT CTTCGAAATC ATG                               33

(2) INFORMATION FOR SEQ ID NO:12:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

GAGCATGGAT CCGCCATCAT GGCTTTCCTT GGACTC                            36

(2) INFORMATION FOR SEQ ID NO:13:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

GAGCATTCTA GAGTTGCAAA CATAATGTGC                                   30

(2) INFORMATION FOR SEQ ID NO:14:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

GAGCATGGAT CCGCCATCAT GGCTTTCCTT GGACTC                            36

(2) INFORMATION FOR SEQ ID NO:15:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

GCACATGGAT CCAAGTTCTT CGAAATCATG                                   30

(2) INFORMATION FOR SEQ ID NO:16:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

```
GAGCATGGAT CCGCCATCAT GGCTTTCCTT GGACTC                                36
```

(2) INFORMATION FOR SEQ ID NO:17:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

```
GAGCATTCTA GAGTTGCAAA CATAATGTGC                                       30
```